(12) United States Patent
Bolyard et al.

(10) Patent No.: US 8,956,275 B2
(45) Date of Patent: Feb. 17, 2015

(54) PORTABLE CONTROLLER WITH INTEGRAL POWER SOURCE FOR MECHANICAL CIRCULATION SUPPORT SYSTEMS

(71) Applicant: Minnetronix, Inc., St. Paul, MN (US)

(72) Inventors: Nathan J. Bolyard, Hudson, WI (US); Don W. E. Evans, Coon Rapids, MN (US); Thomas P. Sutera, Eden Prairie, MN (US)

(73) Assignee: Minnetronix Inc., St. Paul, MN (US)

( * ) Notice: Subject to any disclaimer, the term of this patent is extended or adjusted under 35 U.S.C. 154(b) by 0 days.

(21) Appl. No.: 14/305,917

(22) Filed: Jun. 16, 2014

(65) Prior Publication Data

US 2014/0296614 A1    Oct. 2, 2014

Related U.S. Application Data

(63) Continuation of application No. 14/052,486, filed on Oct. 11, 2013, now Pat. No. 8,753,256, which is a continuation of application No. 13/041,233, filed on Mar. 4, 2011, now Pat. No. 8,556,795.

(60) Provisional application No. 61/416,643, filed on Nov. 23, 2010.

(51) Int. Cl.
| | | |
|---|---|---|
| *A61N 1/362* | (2006.01) | |
| *G05B 19/10* | (2006.01) | |
| *A61M 1/10* | (2006.01) | |
| *A61M 1/12* | (2006.01) | |

(52) U.S. Cl.
CPC .............. *A61M 1/1086* (2013.01); *A61M 1/127* (2013.01)
USPC ............................................. 600/16; 318/567

(58) Field of Classification Search
USPC .............................................. 600/16; 318/567
See application file for complete search history.

(56) References Cited

U.S. PATENT DOCUMENTS

| | | |
|---|---|---|
| 3,633,217 A | 1/1972 | Lance |
| 4,957,504 A | 9/1990 | Chardack |
| 4,991,340 A | 2/1991 | Schildt |
| 5,089,017 A | 2/1992 | Young et al. |

(Continued)

FOREIGN PATENT DOCUMENTS

| | | |
|---|---|---|
| EP | 0760244 A1 | 3/1997 |
| GB | 2140193 A | 11/1984 |

(Continued)

OTHER PUBLICATIONS

Tursini et al., "Speed and position estimation for PM synchronous motor with back-EMF observer," conference Record of the 2005 IEEE Industry Applications Conference Fortieth IAS Annual Meeting, IEEE cat. No. 05, vol. 3, Oct. 2, 2005 pp. 2083-2090.

(Continued)

*Primary Examiner* — Nicole F Lavert
(74) *Attorney, Agent, or Firm* — Shumaker & Sieffert, P.A.

(57) ABSTRACT

A portable external device for a mechanical circulation support system includes first and second power sources, e.g. batteries and control electronics for redundant uninterrupted operation of an implantable blood pump. The control and power source module may be configured to accommodate a variety of wearable configurations for patient convenience and comfort.

29 Claims, 54 Drawing Sheets

(56) References Cited

U.S. PATENT DOCUMENTS

| | | |
|---|---|---|
| 5,569,156 A | 10/1996 | Mussivand |
| 5,613,935 A | 3/1997 | Jarvik |
| 5,766,207 A | 6/1998 | Potter et al. |
| 6,048,363 A | 4/2000 | Nagyszalanczy et al. |
| 6,183,412 B1 | 2/2001 | Benkowski et al. |
| 6,264,601 B1 | 7/2001 | Jassawalla et al. |
| 6,977,479 B2 | 12/2005 | Hsu |
| 7,105,022 B2 | 9/2006 | Yoon et al. |
| 7,561,686 B2 | 7/2009 | Vance |
| 7,585,322 B2 | 9/2009 | Azzolina |
| 8,394,009 B2 | 3/2013 | Bolyard et al. |
| 8,556,795 B2 | 10/2013 | Bolyard et al. |
| 2003/0069465 A1 | 4/2003 | Benkowski et al. |
| 2005/0071001 A1 | 3/2005 | Jarvik |
| 2005/0151502 A1 | 7/2005 | Quirion |
| 2006/0058873 A1 | 3/2006 | Peralta |
| 2007/0142696 A1 | 6/2007 | Crosby et al. |
| 2007/0197854 A1 | 8/2007 | Marseille et al. |
| 2008/0294252 A1 | 11/2008 | Myklebust |
| 2008/0306329 A1 | 12/2008 | Lu et al. |
| 2009/0118827 A1 | 5/2009 | Sugiura |
| 2009/0149951 A1 | 6/2009 | Sugiura et al. |
| 2011/0184289 A1 | 7/2011 | Oshiki et al. |
| 2011/0218383 A1 | 9/2011 | Broen et al. |
| 2011/0218384 A1 | 9/2011 | Bachman et al. |
| 2012/0130153 A1 | 5/2012 | Bolyard et al. |
| 2013/0225911 A1 | 8/2013 | Bolyard et al. |

FOREIGN PATENT DOCUMENTS

| | | |
|---|---|---|
| JP | 2008544441 A | 12/2008 |
| JP | 2009524504 A | 7/2009 |
| WO | 9908745 A1 | 2/1999 |
| WO | 9917819 A1 | 4/1999 |
| WO | 2007053881 A1 | 5/2007 |
| WO | 2007070932 A1 | 6/2007 |
| WO | 2007072025 A1 | 6/2007 |
| WO | 2008154387 A1 | 12/2008 |

OTHER PUBLICATIONS

Food and Drug Administration, Approval documentation for "Thoratec HeartMate II® Left ventricular Assist System (LVAS)," Thoratec Corporation, Apr. 21, 2008, retrieved from, http://www.accessdata.fda.gov/cdrh_docs/pdf6/P060040A, 3 pp.

"HeartMate II® Left Ventricular Assist System," Thoratec Corporation, accessed on Aug. 9, 2011 from http://www.thoratec.com/medical-professionals/vad-product-information/heartmate-II-lvad.aspx., 2 pp.

Prosecution History from U.S. Patent 8,556,795, granted Oct. 15, 2013, 24 pp.

International Search Report and Written Opinion of international application No. PCT/US2011/027290, dated Aug. 11, 2011, 13 pp.

International Preliminary Report on Patentability from international application No. PCT/US2011/027290, dated Nov. 2, 2012, 22 pp.

Reply to Written Opinion dated Aug. 11, 2011 from international application No. PCT/US2011/027290, dated Sep. 20, 2012, 22 pp.

Prosecution History from U.S. Appl. No. 14/052,486, filed Oct. 11, 2013, 10 pp.

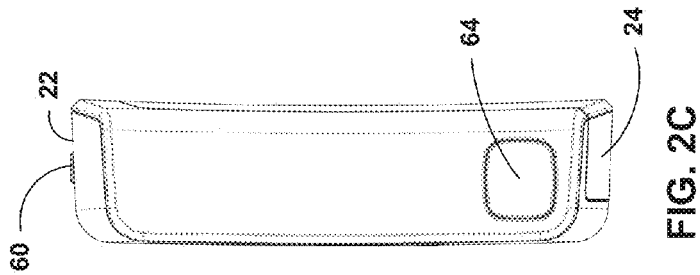
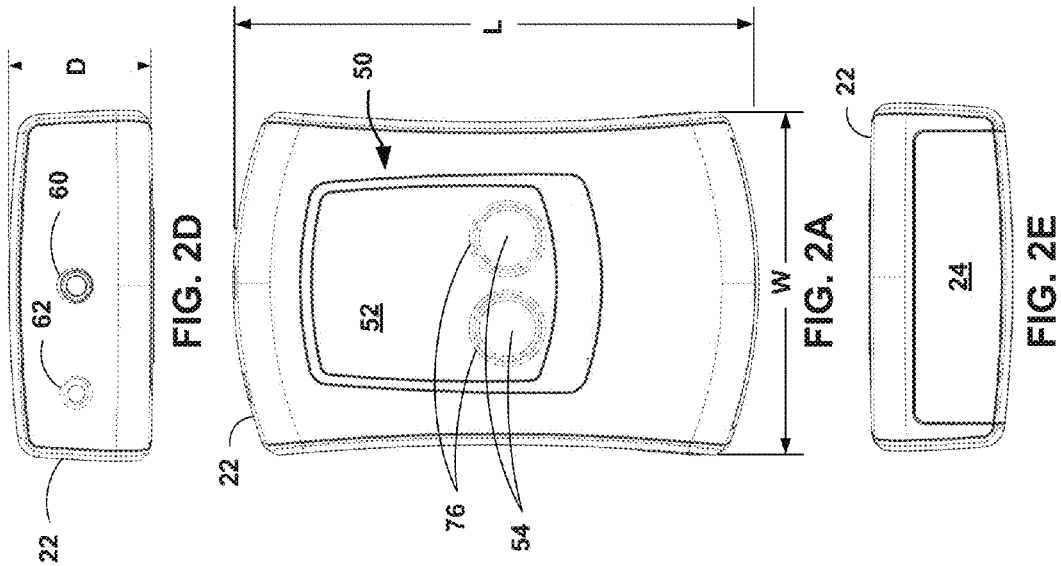
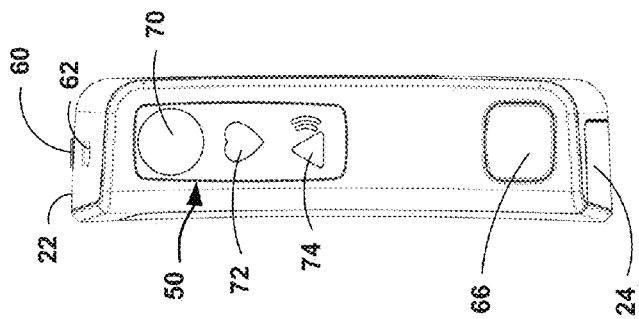

$$v_\alpha = R \cdot i_\alpha + L \frac{di_\alpha}{dt} + emf_\alpha$$

FIG. 14A $$v_\alpha = R \cdot i_\alpha + L \frac{di_\alpha}{dt} + \frac{d}{dt} RotorFlux_\alpha$$

FIG. 14B $$\frac{d}{dt} RotorFlux_\alpha = v_\alpha - R \cdot i_\alpha - L \frac{di_\alpha}{dt}$$

FIG. 14C $$RotorFlux_\alpha = \int (v_\alpha - R \cdot i_\alpha) dt - L \cdot i_\alpha = \psi_{p\alpha}$$

FIG. 14D $$RotorFlux_\beta = \int (v_\beta - R \cdot i_\beta) dt - L \cdot i_\beta = \psi_{p\beta}$$

FIG. 14E $$\varphi = \tan^{-1}\left(\frac{\psi_{p\beta}}{\psi_{p\alpha}}\right)$$

FIG. 14F

| A | B | C | $V_{AN}$ | $V_{BN}$ | $V_{CN}$ |
|---|---|---|---|---|---|
| 0 | 0 | 0 | 0 | 0 | 0 |
| 0 | 0 | 1 | $-V_{DC}/3$ | $-V_{DC}/3$ | $2V_{DC}/3$ |
| 0 | 1 | 0 | $-V_{DC}/3$ | $2V_{DC}/3$ | $-V_{DC}/3$ |
| 0 | 1 | 1 | $-2V_{DC}/3$ | $V_{DC}/3$ | $V_{DC}/3$ |
| 1 | 0 | 0 | $2V_{DC}/3$ | $-V_{DC}/3$ | $-V_{DC}/3$ |
| 1 | 0 | 1 | $V_{DC}/3$ | $-2V_{DC}/3$ | $V_{DC}/3$ |
| 1 | 1 | 0 | $V_{DC}/3$ | $V_{DC}/3$ | $-2V_{DC}/3$ |
| 1 | 1 | 1 | 0 | 0 | 0 |

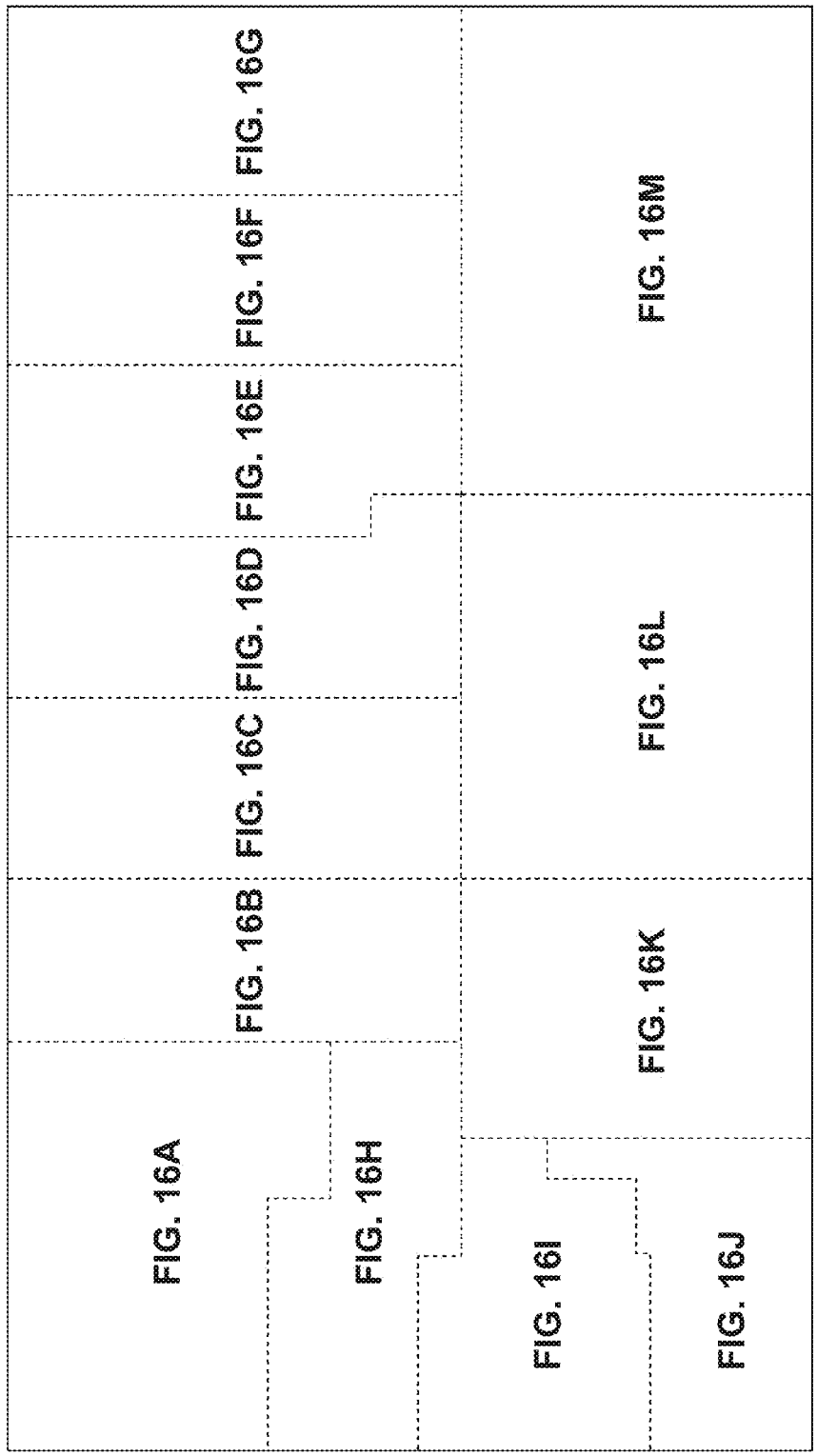

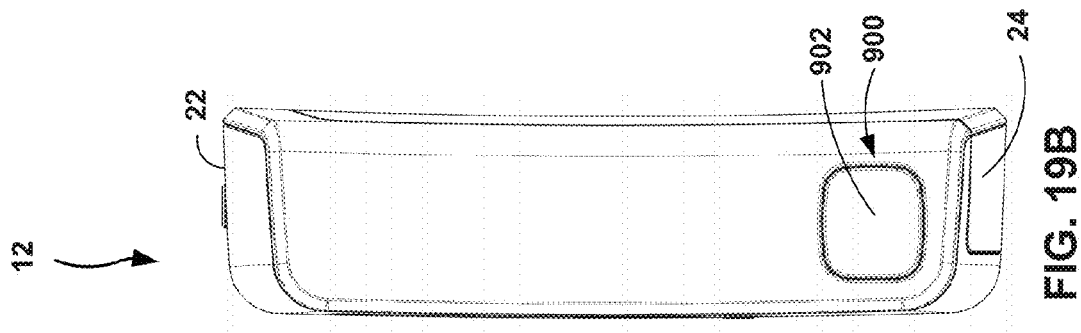
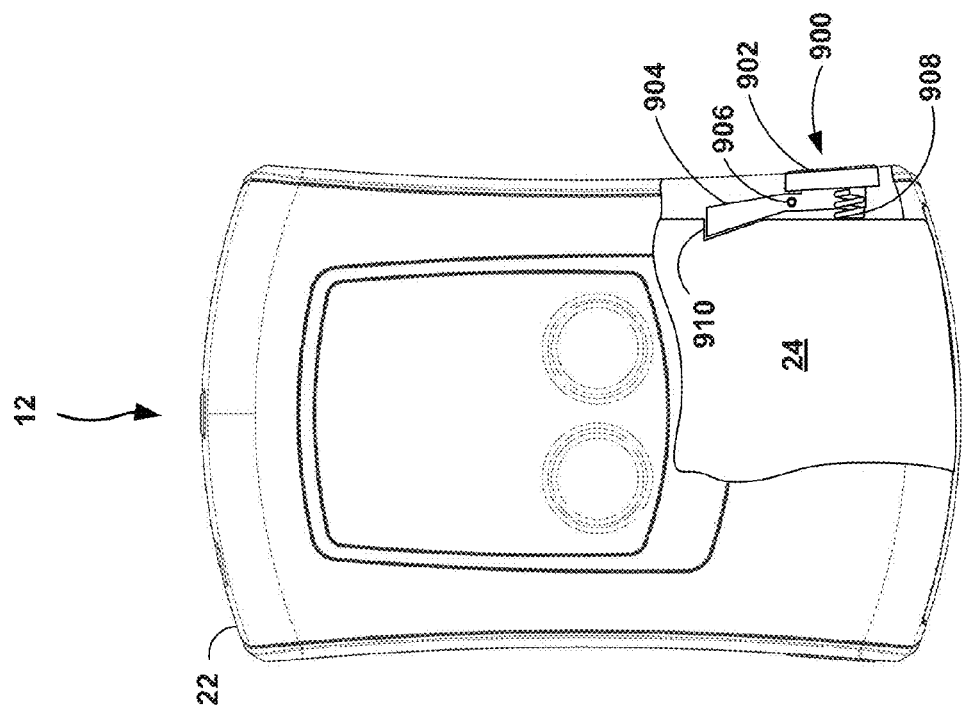

PORTABLE CONTROLLER WITH INTEGRAL POWER SOURCE FOR MECHANICAL CIRCULATION SUPPORT SYSTEMS

This application is a continuation of U.S. application Ser. No. 14/052,486, filed Oct. 11, 2013, which is a continuation of U.S. application Ser. No. 13/041,233, filed Mar. 4, 2011, which claims the benefit of U.S. Provisional Application No. 61/416,643, filed Nov. 23, 2010, the entire content of each of which is incorporated herein by this reference.

BACKGROUND

Generally speaking, heart failure is a major public health problem affecting a great number of people. Heart transplantation has been one of the most effective therapies for treating heart failure. However, transplantations may be limited by complications from long-term immunosuppressive therapy, allograft coronary artery diseases, as well as the limited number of donor organs.

Mechanical circulation support (MCS) systems, both total artificial hearts (TAH) and ventricular assist devices (VAD) have been studied in the hopes of augmenting or replacing the role of heart transplantation for heart failure patients. A VAD may be a left ventricular assist device (LVAD), a right ventricular assist device (RVAD) or a biventricular assist device (bi-VAD). Generally speaking, VADs may be employed to provide heart failure patients with therapies including as a bridge to or recovery from heart transplantation, as well as a long-term alternative to the transplantation.

TAHs and VADs are blood pumping devices connected to a patient to receive blood from a source and pump the blood to one or more destinations within the body of the patient. For example, an LVAD receives blood from the atrium or ventricle of a patient and pumps the blood into the aorta. An RVAD, on the other hand, receives blood from the atrium or ventricle and pumps the blood it into the pulmonary artery. An MCS generally includes external components including, e.g., control electronics and power sources connected by one or more percutaneous cables to internal components including, e.g., a blood pump. As a patient resumes regular activities after receiving an MCS, the design and configuration of the MCS equipment they wear becomes an important aspect of their safety and comfort.

SUMMARY

In general, the techniques described herein are directed to a portable external device for a mechanical circulation support system that includes a controller for controlling an implantable pump powered by a power source integral with the controller.

In one example, a portable external device for a mechanical circulation support system includes a power source, digital memory, and control electronics. The power source is configured to power an implantable pump. The digital memory stores an algorithm for controlling an electric motor configured to drive the implantable pump. The control electronics are configured to control the electric motor employing the algorithm. The algorithm comprises instructions for causing the control electronics to estimate a back electromotive force (EMF) of the electric motor, determine a rotational position of a rotor of the electric motor based on the estimated back EMF of the electric motor, determine a pulse width modulated (PWM) voltage signal to send from the power source to the electric motor to drive the implantable pump based on the rotational position of the rotor of the electric motor, determine an error of the estimated back EMF, compare the error of the estimated back EMF to a threshold, and control the electric motor employing a trapezoidal control algorithm stored on the digital memory if the error of the estimated back EMF is greater than the threshold.

In another example, a mechanical circulation support system includes an implantable pump and a portable external device. The portable external device includes a power source, digital memory, and control electronics. The power source is configured to power an implantable pump. The digital memory stores an algorithm for controlling an electric motor configured to drive the implantable pump. The control electronics are configured to control the electric motor employing the algorithm. The algorithm comprises instructions for causing the control electronics to estimate a back electromotive force (EMF) of the electric motor, determine a rotational position of a rotor of the electric motor based on the estimated back EMF of the electric motor, determine a pulse width modulated (PWM) voltage signal to send from the power source to the electric motor to drive the implantable pump based on the rotational position of the rotor of the electric motor, determine an error of the estimated back EMF, compare the error of the estimated back EMF to a threshold, and control the electric motor employing a trapezoidal control algorithm stored on the digital memory if the error of the estimated back EMF is greater than the threshold.

The details of one or more examples are set forth in the accompanying drawings and the description below. Other features, objects, and advantages of examples according to this disclosure will be apparent from the description and drawings, and from the claims.

BRIEF DESCRIPTION OF DRAWINGS

FIGS. 2A-2E are a number of plan and elevation views illustrating an example of the control and power source module of FIG. 1.

FIGS. 13-15B illustrate details of field-oriented control (FOC) techniques that may be used to control an electric motor of an implantable blood pump.

FIGS. 19A and 19B illustrate another battery release latch mechanism that may be employed in conjunction with control and power source modules according to this disclosure.

DETAILED DESCRIPTION

Figure 1:
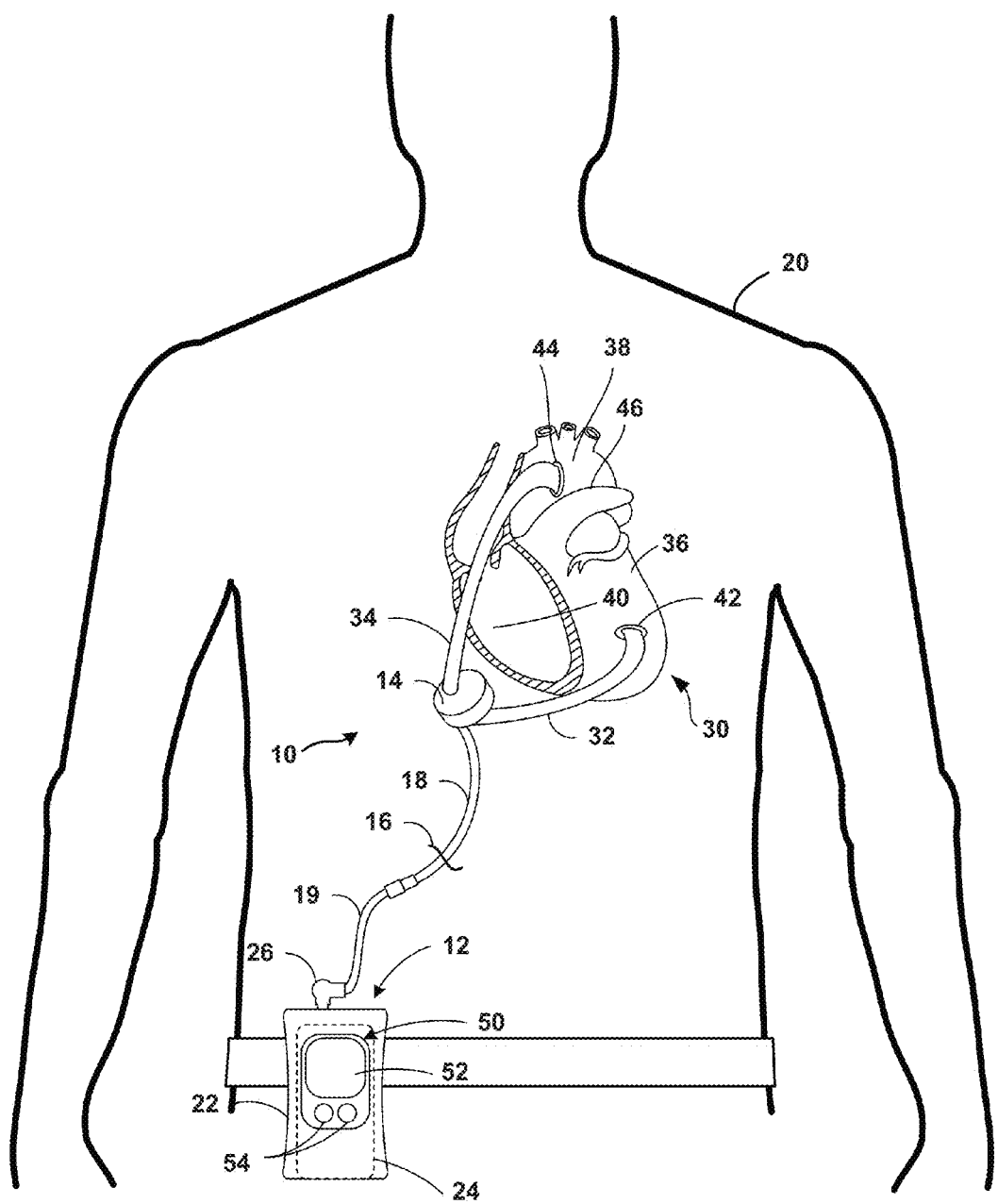
FIG. 1 is a conceptual diagram illustrating an example left ventricular assist device (LVAD) including a portable external control and power source module.

FIG. 1 is a conceptual diagram illustrating an example left ventricular assist device (LVAD) 10 including portable control and power source module 12 percutaneously connected to implanted pump 14 through incision 16 by cable 18 and cable extension 19. Control and power source module 12 includes housing 22, an internal battery (see FIGS. 3 and 5), and removable battery 24 shown in FIG. 1. Control and power source module 12 also includes connector 26 and user interface 50. User interface 50 includes display screen 52 and input buttons 54, as well as a number of other elements described below with reference to FIG. 2B.

As described in greater detail in the following examples, control and power source module 12 is a portable external device for a mechanical circulation support system that includes a controller for controlling implanted pump 12, which is powered by a power source integral with the controller. The power source of example control and power source module 12 includes removable battery 24, which is removably connected to housing 22 of the control and power source module, and an internal back-up battery (see FIGS. 3 and 5) arranged within the housing. Control and power source module 12 is sized to accommodate a variety of wearable configurations for patient 20, including, e.g., being worn on a belt wrapped around the waist of patient 20 in FIG. 1.

Cable 18 connects control and power source module 12 and pump 14 to communicate power and other signals between the external module and the implanted pump. In the example of FIG. 1, cable extension 19 connects cable 18 to control and power source module 12 via connector 26. Cable extension 19 may be fabricated in a variety of lengths and may be employed to improve the flexibility of wearing control and power source module 12 on the body of patient 20. In one example, cable extension 19 may be itself extendable such that the cable can assume a number of different lengths. For example, cable extension 19 may be coiled such that stretching and unwinding the coiled cable extension will cause it to assume a number of different lengths. In another example, control and power source module 12 may include a mechanism from which cable extension 19 may be unwound and to which the extension may be rewound to cause it to assume a number of different lengths.

Control and power source module 12 also includes control electronics (not shown in FIG. 1) configured to control operation of various components of LVAD 10 including pump 14, removable battery 24, the internal battery (see FIGS. 3 and 5), and user interface 50. As noted above, user interface 50 includes display screen 52 and input buttons 54. Display screen 52 may include a number of different types of displays, including, e.g., a liquid crystal display (LCD), dot matrix display, light-emitting diode (LED) display, organic light-emitting diode (OLED) display, touch screen, or any other device capable of delivering to and/or accepting information from a user. Display 52 may be configured to present text and graphical information in one or more colors. For example, display 52 may be configured to display the charge status of removable battery 24 and the internal battery of control and power source module 12, as well as present alarms to a user including instructions for taking action in response to the alarm. In one example of control and power source module 12, input buttons 54 are non-contact capacitive sensors configured to indicate input from a user without the user actually touching the buttons or any other part of the control and power source module.

Pump 14 of LVAD 10 may be surgically implanted within patient 20 including, e.g., in the abdominal cavity of the patient as illustrated in the example of FIG. 1. In other examples, pump 14 may be implanted in other locations within patient 20. Pump 14 is connected to heart 30 of patient 20 by inlet and outlet cannula 32, 34. In the example LVAD 10 of FIG. 1, inlet cannula 32 communicates blood from left ventricle 36 (LV) of heart 30 pump 14. Outlet cannula 34 communicates blood from pump 14 to aorta 38 of patient 20. Pump 14 includes a rigid housing formed from or with a biocompatible material or coating that resists corrosion and degradation from bodily fluids. Examples of suitable biocompatible materials include titanium and biologically inert polymers. Pump 14 may include a variety of types of positive displacement mechanisms capable of drawing blood into and ejecting the blood out of the pump. For example, pump 14 may include one of a centrifugal impeller, peristaltic, electromagnetic piston, axial flow turbine pump, magnetic bearing rotary pump, pneumatic displacement pump or another positive displacement mechanism appropriate for use with implantable devices such as RVAD 10.

In the example of FIG. 1, ventricular assist system 10 is illustrated assisting left ventricle 36 (LV) of heart 30 of patient 20. However, in other examples, the techniques disclosed may be employed in other types of mechanical circulation support (MCS) systems configurable to, e.g., assist right ventricle 40 in a right ventricular assist device (RVAD), as well as both ventricles 36, 40 in a biventricular assist device (BiVAD). As a general matter, therefore, the source of blood for example VADs may be described generally as the assisted ventricle, while the destination of the pressurized blood delivered by the control and power source module may be designated as the arterial vessel.

Referring again to FIG. 1, each of inlet and outlet cannulas 32, 34 may be formed from flexible tubine extending to left ventricle 36 and aorta 38, respectively. Inlet and outlet cannulas 32, 34 may be attached to tissue of left ventricle 36 and aorta 38, respectively, by, e.g., sutures to establish and maintain blood flow, and may include appropriate structure for such attachment techniques including, e.g. suture rings 42, 44. In any of the aforementioned LVAD, RVAD, or BiVAD configurations, inlet cannula 32 is anastomosed to the assisted ventricle (or ventricles), while outlet cannula 34 is anastomosed to the corresponding assisted arterial vessel, which for left ventricular assist is typically aorta 38 and for right ventricular assist is typically pulmonary artery 46.

FIGS. 2A-E are a number of plan and elevation views illustrating an example configuration of control and power source module 12 of FIG. 1. FIG. 2A is a front elevation view of example control and power source module 12. FIGS. 2B and 2C are left and right elevation views, respectively, of control and power source module 12. FIGS. 2D and 2E are top and bottom plan views, respectively, control and power source module 12. Control and power source module 12 includes housing 22, user interface 50, pump cable port 60, external power source port 62, battery release buttons 64 and 66, and removable battery bay door 68. User interface 50 includes display screen 52, input buttons 54, as well as mute button 70 and status indicators 72 and 74 illustrated in FIG. 2B.

Control and power source 12 includes a controller for controlling implanted pump 12 powered by a power source integral with the controller and is sized to accommodate a variety of wearable configurations for patient 20, including, e.g., being worn on a belt wrapped around the waist of the patient, as illustrated in FIG. 1. In one example, control and power source module 12, and, in particular, housing 22 is fabricated to specific size and weight targets to maintain the module at a size that facilitates flexibility and convenience for patient 20. For example, housing 22 of control and power source module 12 may be fabricated with a length, L, in a range from approximately 100 millimeters to approximately 140 millimeters, a width, W, in a range from approximately 60 millimeters to approximately 90 millimeters, and a depth, D, in a range from approximately 20 millimeters to approximately 40 millimeters. Control and power source module 12 may also be sized based on a total volume of the device. For example, housing 22 of control and power source module 12 may be fabricated to include a volume in a range from approximately 120 centimeters cubed to approximately 504 centimeters cubed. In one example, in addition to or in lieu of specific size targets, control and power source module 12 may also include a target weight. For example, control and power source module 12, including removable battery 24 and the internal battery (not shown in FIGS. 2A-E) may be fabricated to include a weight in a range from approximately 0.4 kilograms to approximately 0.8 kilograms.

The size and weight of control and power source module 12 may depend, at least in part, on the components of which the device is comprised, including, e.g. housing 22, display 52, removable battery 24 and in the internal battery, as well as the control electronics arranged within the housing of the device. In one example, the electronics of control and power source module 12 may include, e.g., one or more processors, memory, telemetry, charging circuitry, speakers, and power management circuitry. In any event, the size and weight of the internal components of control and power source module, including, e.g., display 52, status indicators 72 and 74, and the internal electronics of the device, may be proportional to the energy required to power the components. Thus, reducing the energy requirements of the electronics of control and power source module 12 may not only serve to extend battery life, but may also reduce the size and weight of the device.

In view of the foregoing considerations regarding pump and controller electronics power consumption, in one example, control and power source module 12 may be configured such that the ratio of power consumed by the electronics of the control and power source module to the power consumed by implanted pump 14 (see FIG. 1) is approximately equal to a target value. By way of comparison, some prior external VAD controllers may have a ratio of power consumed by the electronics of the controller to the power consumed by the pump connected to the controller of approximately ½. In one example of control and power source module 12, the ratio of power consumed by the electronics of the control and power source module to the power consumed by implanted pump 14 (see FIG. 1) is approximately equal to $4/20$. In another example of control and power source module 12, the ratio of power consumed by the electronics of the control and power source module to the power consumed by implanted pump 14 (see FIG. 1) is approximately equal to $1/100$. By way of comparison, some prior external VAD controllers, which may be considerably larger than examples according to this disclosure, may have a ratio of power consumed by the electronics of the controller to the power consumed by the pump connected to the controller on the order of approximately ½.

In another example, control and power source module 12 may be configured such that the power consumed by the electronics of the control and power source module is equal to a target value. For example, the electronics of control and power source module 12 may be configured to consume power in a range from approximately 0.25 to approximately 1.25 watts.

Example control and power source module 12 of FIGS. 2A-2E includes user interface 50, including display screen 52, input buttons 54, mute button 70 and status indicators 72 and 74. Display screen 52 may include a number of different types of displays, and may be configured to present text and graphical information in one or more colors. In one example, input buttons 54 are non-contact capacitive sensors configured to indicate input from a user without the user actually touching the buttons or any other part of the control and power source module. Although input buttons 54 may, in one example, include non-contact sensors, the buttons may be arranged in depressions 76 in housing 22 provide tactile feedback to a user searching for or using the buttons to view information on display 52 and otherwise interact with control and power source module 12. In one example, input buttons 54 may be soft keys configured to execute different functions on control and power source module 12 based on, e.g., current functions and contexts indicated on display 52. In such examples, the current function associated buttons 54 operating as soft keys may be presented as labels on display 52 just above each of the buttons. In one example, input buttons 54 correspond to two main functions for interacting with control and power source module 12. For example, one of input buttons 54 may function as a "home" button that, when activated by a user, navigates to a default screen presented on display 52 of user interface 50. Additionally, in such an example, the other one of input buttons 54 may function as a "next" button that, when activated by a user, toggles to the next screen in a series of possible screens that may be presented on display 52 of user interface 50.

As illustrated in FIG. 2E, user interface 50 of control and power source module 12 also includes mute button 70 and status indicators 72 and 74. In one example, mute button 70 may be configured to, when depressed, mute audible alerts issued by speakers of control and power source module 12. Mute button 70 may, in one example, only mute alerts temporarily, for example to allow patient 20 to leave a public place with other people that may be disturbed by the alert issued by speakers of control and power source module 12. In one example, status indicators 72 and 74 may be lighted, e.g. LED lighted windows that indicate the operating status of control and power source module 12 and/or implanted pump 14. For example, status indicator 72 may be illuminated to indicate that control and power source module 12 and/or implanted pump 14 are operating normally without error. Status indicator 74, on the other hand, may be illuminated to indicate one or more alarm states that indicate errors or other actionable states of control and power source module 12 and/or implanted pump 14. For example, status indicator 74 may be illuminated to indicate the state of removable battery 24 and/or the internal battery of control and power source module 12 as at or below a threshold charge level. In some examples, status indicator 74 may be illuminated in a variety of manners to indicate different states of control and power source module 12 and/or implanted pump 14, including being illuminated in different colors to indicate alarm states of removable battery 24 and/or the internal battery of different levels of severity.

Example control and power source module of FIGS. 2A-2E also includes pump cable port 60, external power source port 62, and battery release buttons 64 and 66. Pump cable port 60 may be configured to receive pump cable 18 or cable extension 19 directly or via connector 26 as illustrated in FIG. 1. External power source port 62 may be configured to receive one or more types of external power source adaptors, e.g. an AC/DC or DC/DC adaptor configured to charge removable battery 24 and/or the internal battery of control and power source module 12.

As will described in greater detail with reference to FIGS. 3 and 4, control and power source module 12 includes a latch configured to release removable battery 24 from housing 22. The battery release latch of control and power source module may be, in one example, configured to be actuated to release removable battery 24 from housing 22 by at least two independent motions. In FIGS. 2A-2E, the battery release latch of control and power source module 12 includes battery release buttons 64 and 66. In one example, battery release buttons 64 and 66 are biased into a locked position that inhibits removal of removable battery 24 from housing 22 and are configured to be pushed into an unlocked position simultaneously to release the first power source for removal from the housing. In the example control and power source module 12 of FIGS. 2A-2E, battery release button 64 is arranged on right side (from the perspective of the views of FIGS. 2A-2E) of housing 22 and battery release button 66 is arranged on opposing left side of housing 22 such that the two buttons are configured to be pushed in approximately opposite directions to one another.

Figure 3:
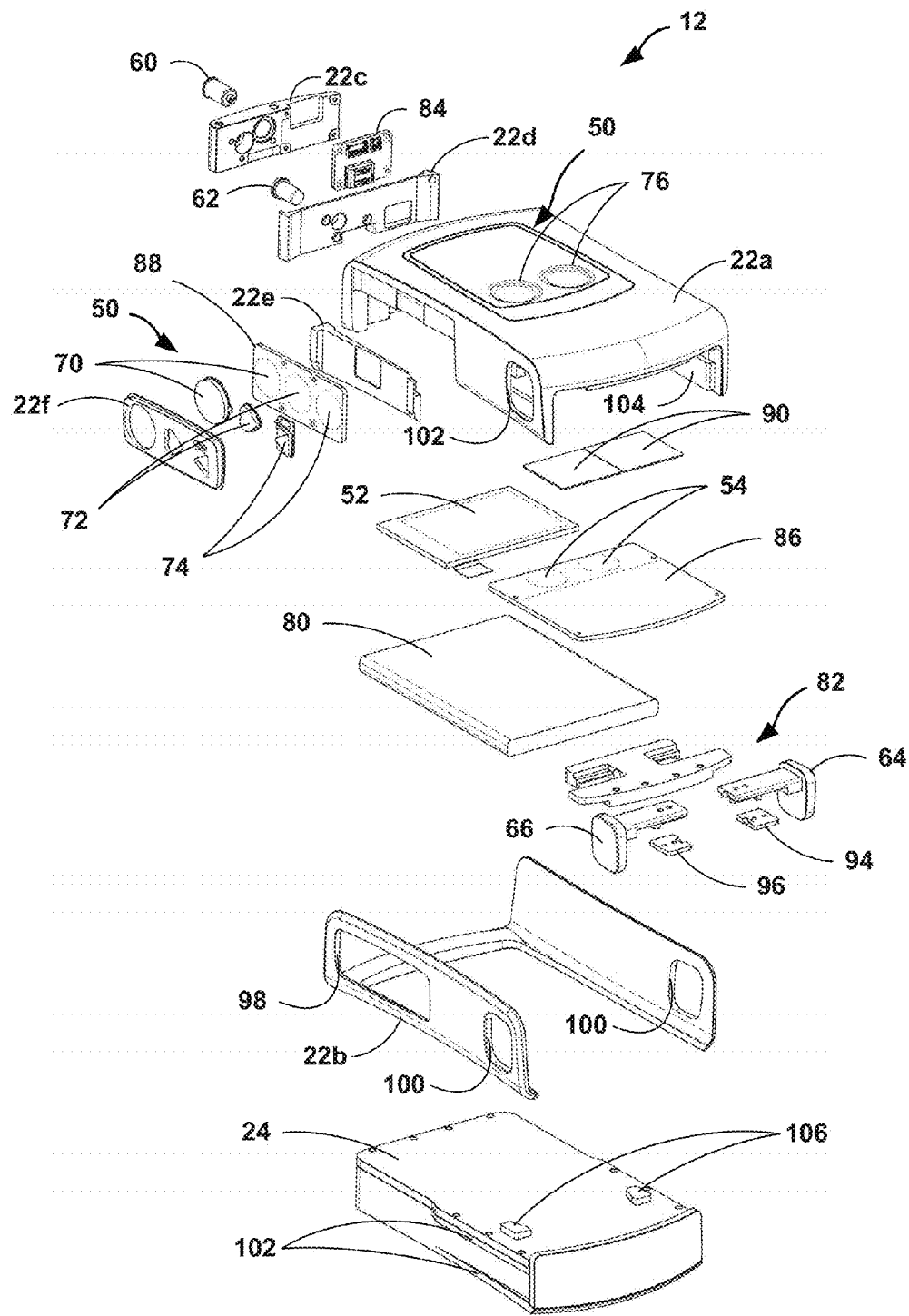
FIG. 3 is an exploded view of the example control and power source module of FIGS. 2A-2E.

FIG. 3 is an exploded view of example control and power source module 12 of FIGS. 2A-2E. Example control and power source module 12 includes housing 22, removable battery 24, internal battery 80, user interface 50, pump cable port 60, external power source port 62, battery release latch 82, circuit boards 84, 86, and 88, and speakers 90. Housing 22 includes a number of pieces, including front shield 22a, sides and back shield 22b, top cap 22c, main board backing 22d, status indicator backing 22e, and status indicator bezel 22f. As illustrated in FIG. 3, removable battery 24 forms part of the back of control and power source module 12. Housing 22 of control and power source module 12, including one or more of front shield 22a, sides and back shield 22b, top cap 22c, main board backing 22d, status indicator backing 22e, and status indicator bezel 22f may be fabricated from a variety of materials, including, e.g., plastics including acrylonitrile butadiene styrene (ABS), polyvinyl siloxane (PVS), silicone, metals including stainless steel, aluminum, titanium, copper, and composites including carbon fiber, glasses, and ceramics. In some examples different portions of housing 22, including front shield 22a, sides and back shield 22b, top cap 22c, main board backing 22d, status indicator backing 22e, and status indicator bezel 22f may be fabricated from the same materials. In another example, however, different portions of housing 22, including one or more of front shield 22a, sides and back shield 22b, top cap 22c, main board backing 22d, status indicator backing 22e, and status indicator bezel 22f may be fabricated from different materials.

In one example, front shield 22a of housing 22 may include a metallic bezel partially or completely surrounding display 52 of user interface 50. The metallic bezel may be fabricated from a variety of thermally conductive materials including, e.g., aluminum, copper, and alloys thereof. The metallic bezel of front shield 22a of housing 22 may be configured to provide thermal conductance of heat generated by one or more of circuit boards 84, 86, and 88, as well as internal battery 80 and/or removable battery 24. In one example, a metallic bezel of front shield 22a is configured to sink heat generated by circuit board 86 associated with user interface 50. The metallic portion of front shield 22a may be thermally coupled to circuit board 86 to increase thermal conduction between the two components, e.g., using a thermally conductive pad, potting material, or a thermal grease interposed between the shield and the circuit board. In a similar manner to front shield 22a, indicator bezel 22f may be configured, in one example, to provide thermal conductance of heat generated by circuit board 88. In such an example, indicator bezel 22f may be fabricated from a variety of thermally conductive materials including, e.g., aluminum, copper, and alloys thereof and may be thermally coupled to circuit board 88 to increase thermal conduction between the two components, e.g., using a thermally conductive pad, potting material, or a thermal grease interposed between the shield and the circuit board.

User interface 50 of control and power source module includes display 52, input buttons 54, mute button 70, and status indicators 72 and 74. Battery release latch 82 includes base 92, right and left push buttons 64 and 66, respectively, and right and left back plates 94 and 96, respectively. Control and power source 12 includes a number of circuit boards, including main board 84, display board 86, and status indicator board 88, one or more of which may be connected to one another. In one example, main board 84 includes the main control electronic components for control and power source module 12, including, e.g. processor(s), memory, telemetry, charging, and power management electronics. Display board 86 includes input buttons 54 and may include other electronics associated with the function of display 52. Additionally, status indicator board 88 may include a number of electronic components associated with mute button 70 and status indicators 72 and 74.

In FIG. 3, main board backing 22d is configured to be connected to front shield 22a and to secure main board 84 and to help secure pump cable port 60 and external power source port 62, along with top cap 22c. Main board 84 is interposed between top cap 22c and main board backing 22d. Pump cable port 60 and external power source port 62 are received by apertures in top cap 22c and main board backing 22d. Status indicator board backing 22e is configured to be connected to front shield 22a and to secure status indicator board 88 to housing 22 of control and power source module 12. Status indicator board 88 may be connected to backing 22e. Each of mute button 70 and status indicators 72 and 74 are comprised of a user interface component configured to be received by bezel 22f and an electronic component on status indicator board 88. In the example of FIG. 3, mute button 70 includes a push button received in an aperture of bezel 22f and a contact or non-contact sensor on indicator board 88. In the example of FIG. 3, status indicators 72 and 74 each include a lens configured to be received in a corresponding aperture in bezel 22f and a light emitter, e.g. an LED on status indicator board 88. Status indicator board 88 and the push button of mute button 72 and lenses of indicators 72 and 74 are interposed between main board backing 22e and bezel 22f.

The sides of shield 22b are configured to mate with and overlay the sides of front shield 22a of housing 22 of control and power source module 12. Sides and back shield 22b includes apertures 98 and 100. Aperture 98 is configured to receive bezel 22f. Apertures 100 are configured to receive buttons 64 and 66 of battery release latch 82 and to be aligned with corresponding apertures 102 in front shield 22a, only one of which can be seen in the view of FIG. 3. Removable battery 24 is connected to housing 22 and configured to be released by battery release latch 82. In particular, tabs 104 on removable battery 24 is configured to be received on rails 106 on the interior of front shield 22a such that the battery may slide into and out of a locked connection with housing 22 of control and power source module 12 via battery release latch 82. Display 52, display board 86 including input buttons 54, speakers 90, internal battery 80, and battery release latch 82 are configured to be arranged within housing 22 of control and power source module over removable battery 24. Base 92 of battery release latch 82 is configured to be fastened to front shield 22a and to slidably receive right and left push buttons 64 and 66 and back plates 94 and 96. Display 52 is generally aligned with a window in front shield 22a and input buttons 54 on display board 86 are generally aligned with depressions 76 in the front shield of housing 22 of control and power source module 12.

In some examples, control and power source module 12 may employ a variety of waterproofing techniques and mechanisms for protecting various components of the device from ingress or egress of one or more materials into or out of housing 22. In one example, removable battery 24 may be electrically coupled with one or more of circuit boards 84, 86, and 88 with, e.g. a multi-pin connection that employs a gasket to seal the releasable connection between battery 24 and the inner components of control and power source module 12 from ingress of materials into housing 22. Such a gasket may be fabricated from a variety of materials, including, e.g. a compressible polymer or an elastomer, e.g. rubber. In one example, one or more parts of housing 22, e.g. one or more of front shield 22a, sides and back shield 22b, top cap 22c may be hermetically sealed. For example, front shield 22a, sides and back shield 22b, top cap 22c may be connected to form enclosed housing 22 by gasket(s), sonic welding or adhesives.

In one example, speakers 90 are piezoelectric speakers that are configured to be fastened, e.g. with an adhesive to an interior surface of front shield 22a of housing 22 of control and power source module 12. Piezoelectric speakers may include a piezoelectric crystal coupled to a mechanical diaphragm. Sound is produced by alternatively applying and removing an electrical signal to the crystal, which responds by flexing and unflexing the mechanical diaphragm in proportion to the voltage applied across the crystal's surfaces. The action of flexing and unflexing the mechanical diaphragm at relatively high frequencies produces vibrations in the diaphragm that emit an audible sound, e.g. sounds in a frequency range from approximately 150 Hz to approximately 4 kHz.

In some examples, a portion of housing 22 may be configured to act in conjunction with speakers 90 to effectively increase the amplitude of the sounds emitted by the speakers. For example, the geometry of a portion of front shield 22a of housing 22 to which speakers 90 are connected may be shaped and sized to cause the shield to resonate in response to vibration of the speakers. For example, the portion of front shield 22a of housing 22 to which speakers 90 are connected may be shaped and sized such that the natural frequency of the combination of housing and speakers modulated to a target frequency within the operational range of the speakers. Controlling speakers 90 to operate at a particular frequency may then cause the speakers and portion of front shield 22a to resonate, thereby effectively increasing the amplitude of the sounds emitted by the speakers. In one example, speakers 90 include piezoelectric speakers that generally perform better above 1000 Hz. As such, the natural frequency of the combination of the portion of front shield 22a to which speakers 90 are attached and the speakers may be modulated to greater than 1000 Hz.

Modulating the housing of a control and power source module to particular resonant frequencies may be accomplished by a number of analytical, numerical, and experimental methods. In one example, the resonant frequency of a housing of a control and power source module may be modulated analytically using theory for thin, elastic plates to determine a starting point for geometry and material properties of the housing. In another example, the resonant frequency of a housing of a control and power source module may be modulated numerically using finite element analysis (FEA) modeling to simulate the vibration characteristics of different modeled geometries. Additionally, a number of processes and techniques, such as Chladni patterns, may be employed to experimentally refine the natural frequency of the housing with the speakers.

Although the example of FIG. 3 includes two speakers 90, other examples may include more or fewer speakers configured to emit audible sounds, e.g. alarms to a user of control and power source module 12. In one example, a control and power source module according to this disclosure includes one speaker. In another example, a control and power source module according to this disclosure includes four speakers.

Figure 4A:
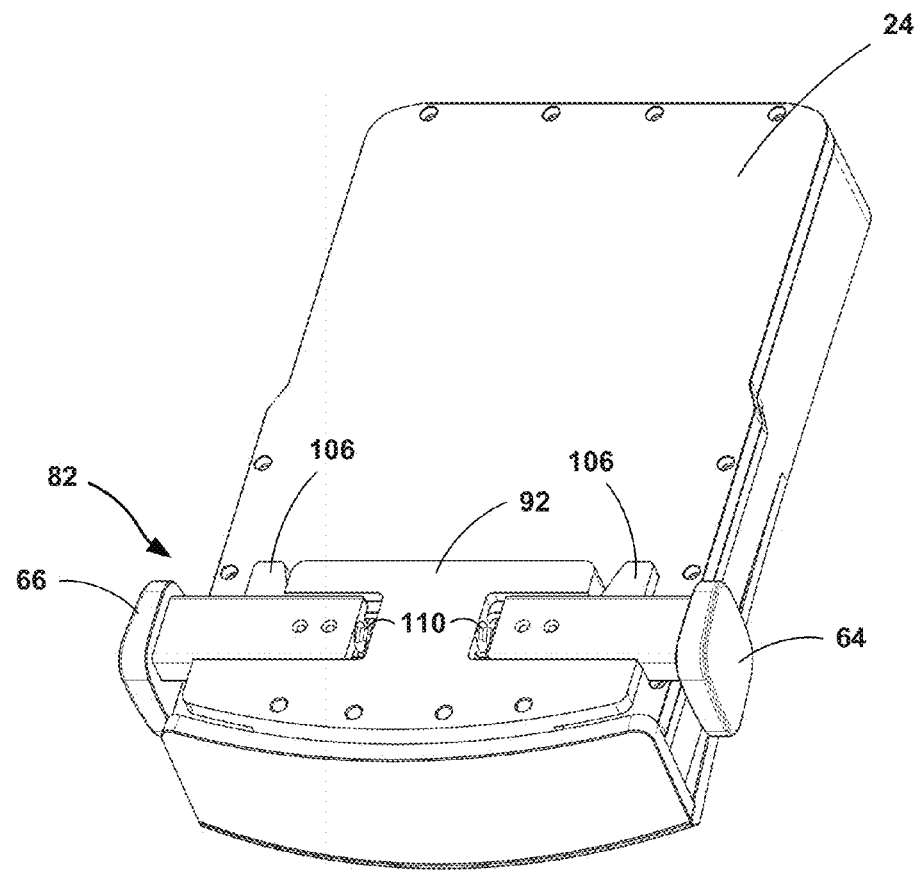
FIGS. 4A and 4B are perspective views of the battery release latch of the example control and power source module of FIGS. 2A-3.
Figure 4B:
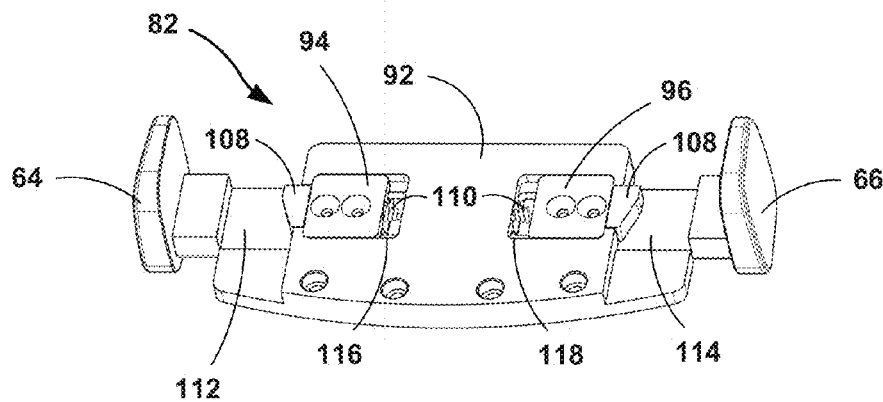

FIGS. 4A and 4B are perspective views of removable battery 24 and battery release latch 82 of control and power source module 12. Removable battery 24 includes stops 106 configured to engage catches 108 on battery release latch 82 to lock the battery in housing 22 of control and power source module 12. Battery release latch 82 includes base 92, right and left push buttons 64 and 66, respectively, right and left back plates 94 and 96, respectively, catches 108, and springs 110.

In FIGS. 4A and 4B, flanges 112 and 114 protrude from push buttons 64 and 66, respectively, and are received by slots 116 and 118, respectively, in base 92. Back plates 94 and 96 are also received by slots 116 and 118 and are fastened to flanges 112 and 114 to slidably connect push buttons 64 and 66, respectively, to base 92 of battery release latch 82. Springs 110 are interposed between a face of slots 116 and 118 of base 92 and connected flanges 112 and 114 and back plates 94 and 96. Springs 110 may function to bias push buttons 64 and 66 into a locked position that inhibits removal of battery 24 from housing 22 of control and power source module 12. In the example of FIGS. 4A and 4B, springs 110 are configured to bias push buttons 64 and 66 laterally outward, in generally opposing directions away from the outer surfaces of removable battery 24 such that catches 108 engage stops 106 on removable battery 24 to inhibit the battery from being removed from housing 22 of control and power source module 12. To release battery 24 from housing 22 of control and power source module 12, both of push buttons 64 and 66 are pushed laterally inward, in generally opposing directions toward the interior region of removable battery 24 such that catches 108 move out of engagement with stops 106 on removable battery 24. In one example, control and power source module 12 may be configured with a second mechanical latching mechanism for battery 24. For example, battery 24 may be received in housing 22 of control and power source module 12 with a friction fit such that a user must apply a threshold force, e.g. 1 pound force to remove the battery from the housing.

Although the example control and power source module 12 described and illustrated with reference to FIGS. 2A-4 includes battery release latch 82 including push buttons 64 and 66, in another example according to this disclosure the latch may be triggered by another mechanism that requires two independent motions to release a removable battery from a control and power source module. In one example according to this disclosure, a battery release latch actuated by at least two independent motions and configured to release a removable power source from a housing of a control and power source module may include a channel and a post biased into a locked position toward a first end of the channel that inhibits removal of the power source from the housing. In such an example, the post may be configured to be pushed in at least two directions toward a second end of the channel into an unlocked position to release the removable power source from the housing of the control and power source module. FIGS. 4C-4H illustrate a number of particular alternative latching mechanisms that may be employed in conjunction with control and power source modules according to this disclosure. In each of the examples of FIGS. 4C-4H, the control and power source module includes a removable battery that may be released from and locked to a housing by the respective example latching mechanisms. Additionally, the direction in which the removable battery may be released from the control and power source module in the illustrated examples is indicated in each of the figures by arrow R.

Figure 4C:
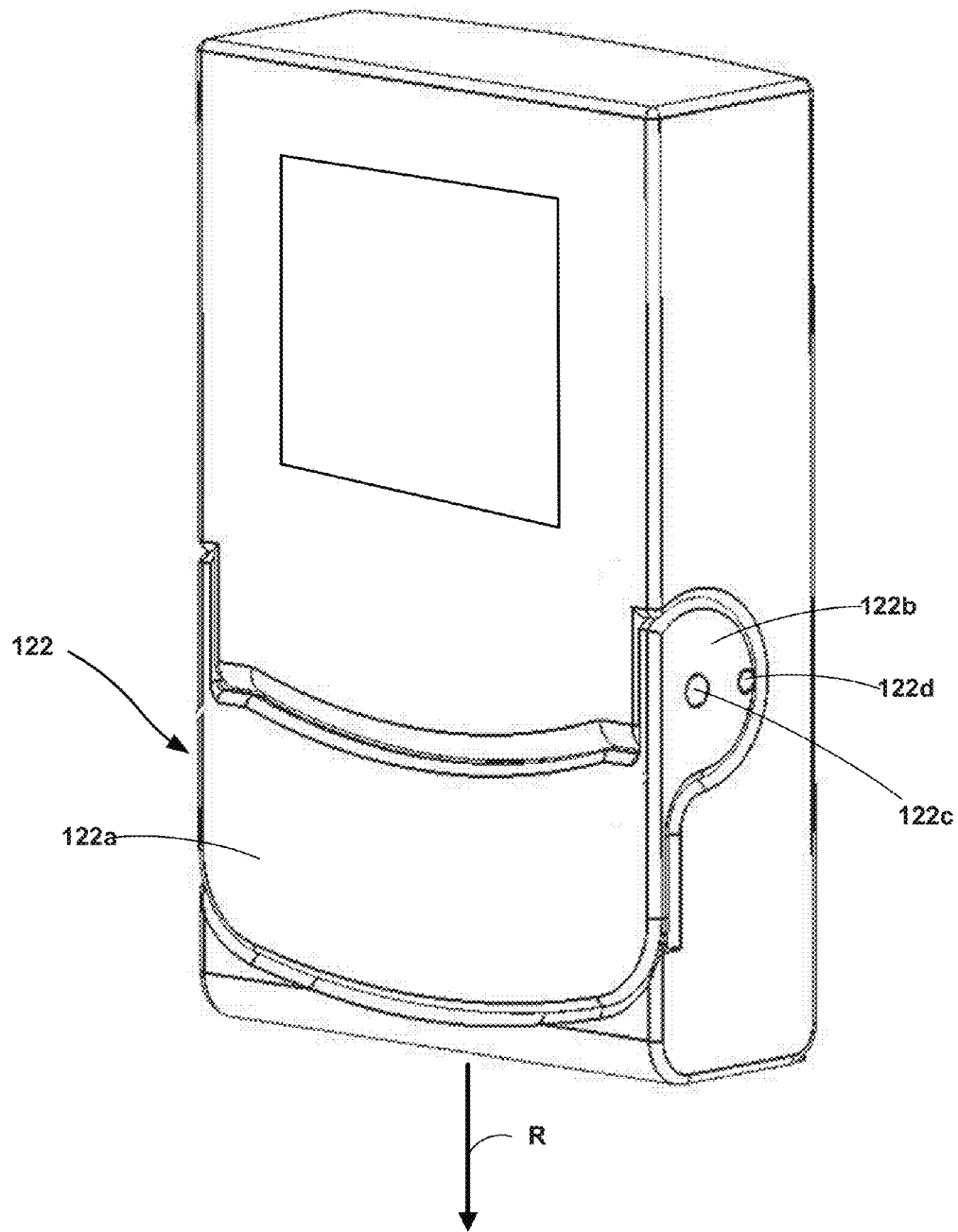
FIGS. 4C-4H illustrate a number of alternative battery release latch mechanisms that may be employed in conjunction with control and power source modules according to this disclosure.

FIG. 4C is a perspective view of a control and power source module including battery release latch 122. Battery release latch 122 includes paddle 122a, two flanges 122b (only one of which is viewable FIG. 4C), pivot 122c and cam 122d. In FIG. 4C, paddle 122a and flanges 122b are pivotably connected to the control and power source module at pivot 122c. Cam 122d is a protrusion extending inward from paddle 122b. Latch 122 may be actuated by rotating paddle 122a away from the control and power source module, which causes flanges 122b to rotate about pivot 122c. Flanges 122b turn cam 122d, which may be received within a channel in the removable battery. Rotating cam 122d pushes against the removable battery such that the battery is pushed downward and out of engagement with the control and power source module. When the battery, or a new or replacement removable battery is reinserted into the control and power source module of FIG. 4C a channel in the battery may engage cam 122d and rotating paddle 122a, which, in turn, rotates flanges 122b, may cause the cam to draw the battery into the housing and lock the battery in place. In one example of latch 122, paddle 122a may be releasably secured to the housing of the control and power source module to prevent inadvertent actuation of the latch. For example, paddle 122a may be held to the housing by a small permanent magnet.

Figure 4D:
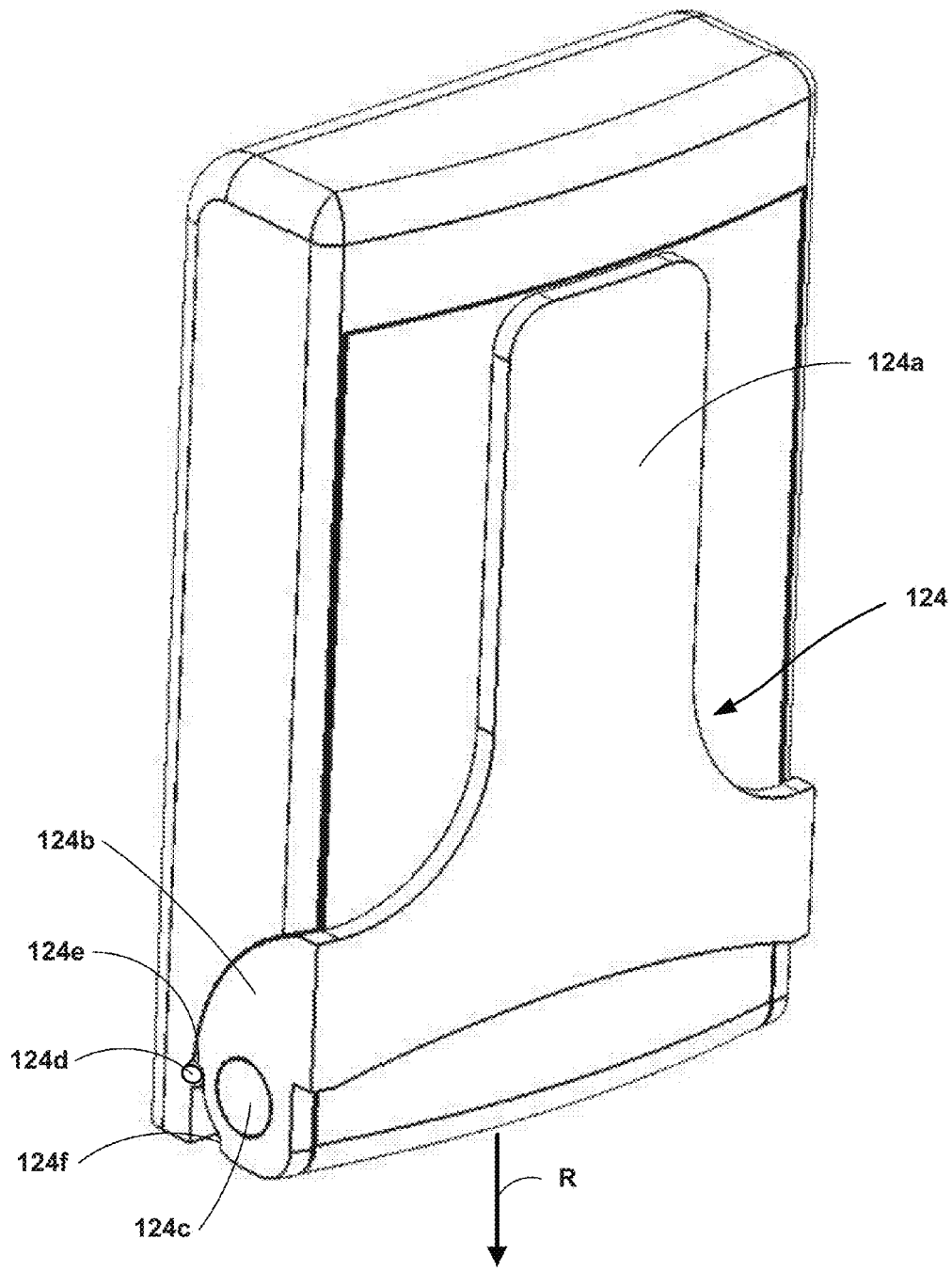

FIG. 4D is a perspective view of a control and power source module including battery release latch 124. Battery release latch 124 includes paddle 124a, two flanges 124b (only one of which is viewable FIG. 4C), pivot 124c and post 124d. Flanges 124b each include two landings 122e, 122f, which are configured to engage post when the removable battery is released and locked into the control and power source module of FIG. 4D. In FIG. 4D, paddle 124a and flanges 124b are pivotably connected to the removable battery of the control and power source module at pivot 124c. Post 124d protrudes from the housing of the control and power source module. Latch 124 may be actuated by rotating paddle 124a away from the control and power source module, which causes flanges 124b to rotate about pivot 124c. Flanges 124b turn until release landing 124f engages post 124b. As paddle 124a and flanges 124c continue to rotate, landing 124f pushes against post 124b, which causes the latch and removable battery to be released from the housing of the control and power source module. When the battery, or a new or replacement removable battery is reinserted into the control and power source module of FIG. 4D, the battery and latch 124 may be pushed into the housing until landing 124f engages post 124d, after which paddle 124a and flanges 124b may be rotated until lock landing 124e engages post 124d. As paddle 124a and flanges 124c continue to rotate, landing 124e pushes against post 124b, which causes the latch and removable battery to be pulled into and locked to the housing of the control and power source module. In one example of latch 124, paddle 124a may be releasably secured to the housing of the control and power source module to prevent inadvertent actuation of the latch. For example, paddle 124a may be held to the housing by a small permanent magnet.

Figure 4E:
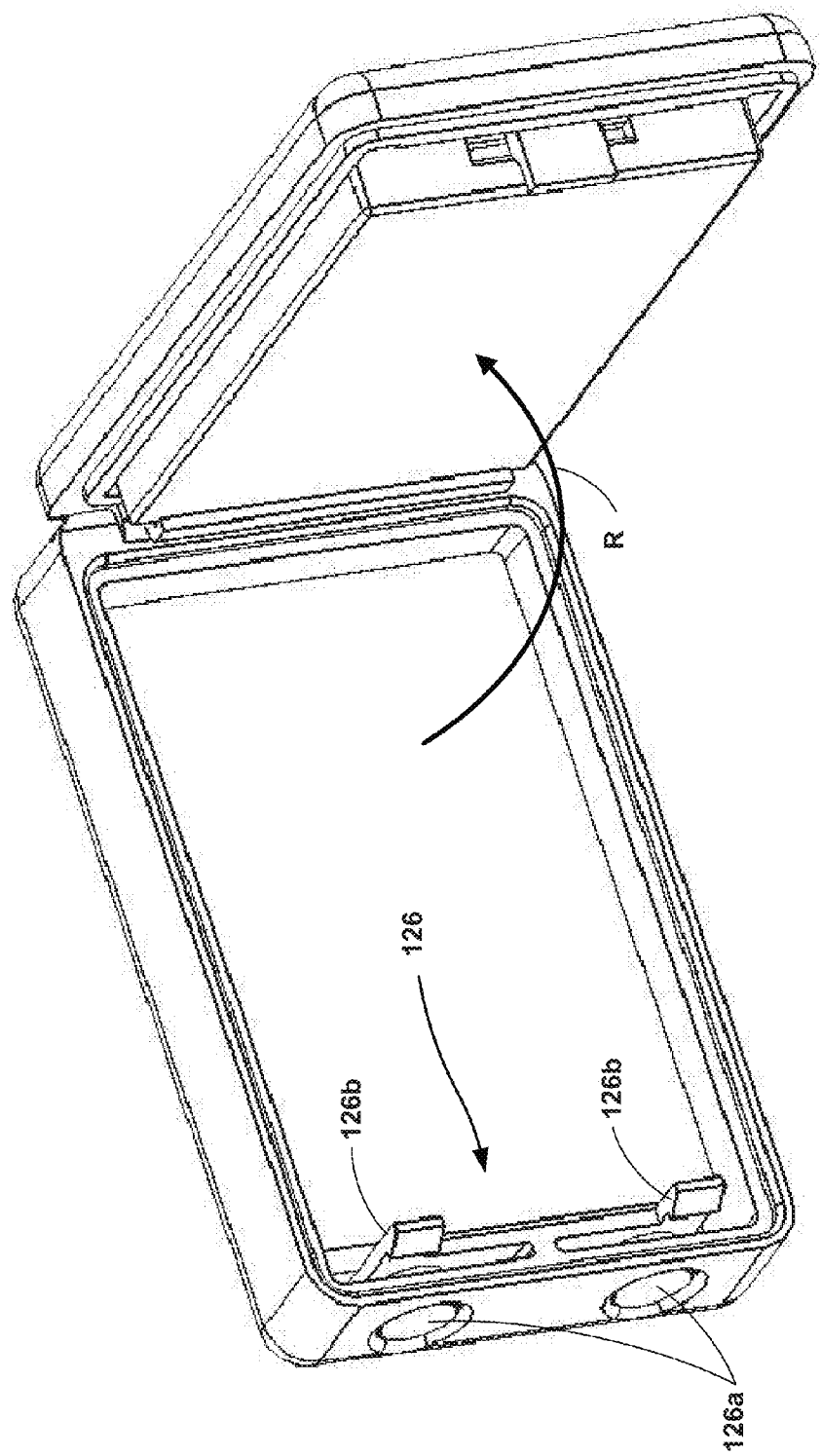

FIG. 4E is a perspective view of a control and power source module including battery release latch 126. The control and power source module of FIG. 4E includes a clam shell design including two halves pivotably connected to one another. Battery release latch 126 includes two buttons 126a and two clips 126b. In FIG. 4E, buttons 126a and clips 126b are connected to the housing of the control and power source module. Buttons 126a are configured to cause clips 126b to move into and out of engagement with catches in the other half of the clam shell housing of the control and power source module of FIG. 4E. Latch 126 may be actuated by pushing both of buttons 126a simultaneously to cause both clips 126b to move out of engagement with respective catches in the other half of the clam shell housing. In one example, the interior surface of the half of the housing opposite clips 126b may include slots that are configured to receive the clips.

Figure 4F:
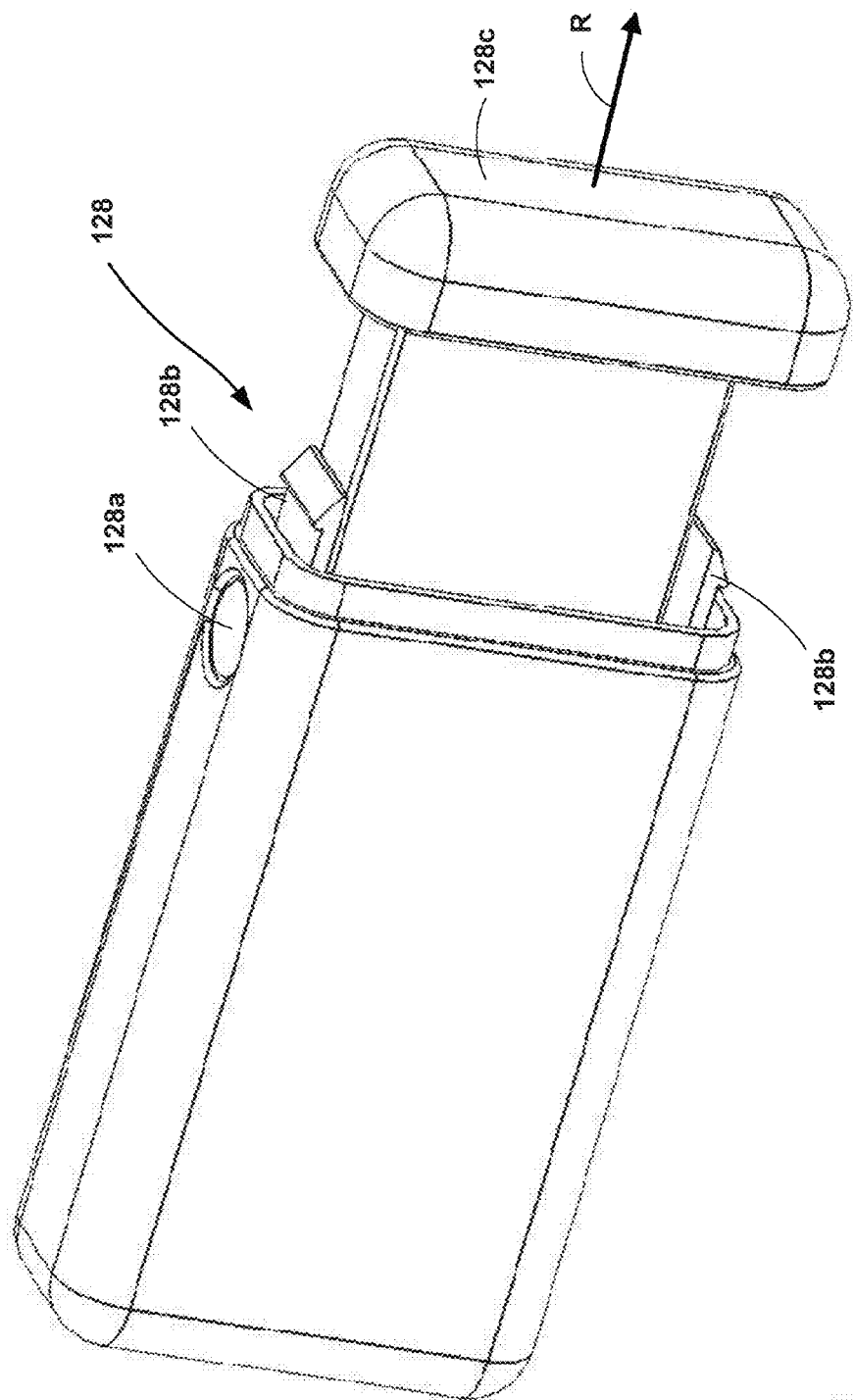

FIG. 4F is a perspective view of a control and power source module including battery release latch 128. Battery release latch 128 includes two buttons 128a and two clips 128b. In FIG. 4F, buttons 128a and clips 128b are connected to the housing of the control and power source module. Buttons 128a are configured to cause clips 128b to move into and out of engagement with catches in cap 128c of the housing of the control and power source module of FIG. 4E. Latch 128 may be actuated by pushing both of buttons 128a simultaneously to cause both clips 128b to move out of engagement with respective catches in cap 128c of the housing. In one example, the interior surface of cap 128c of the housing may include slots that are configured to receive the clips.

Figure 4G:
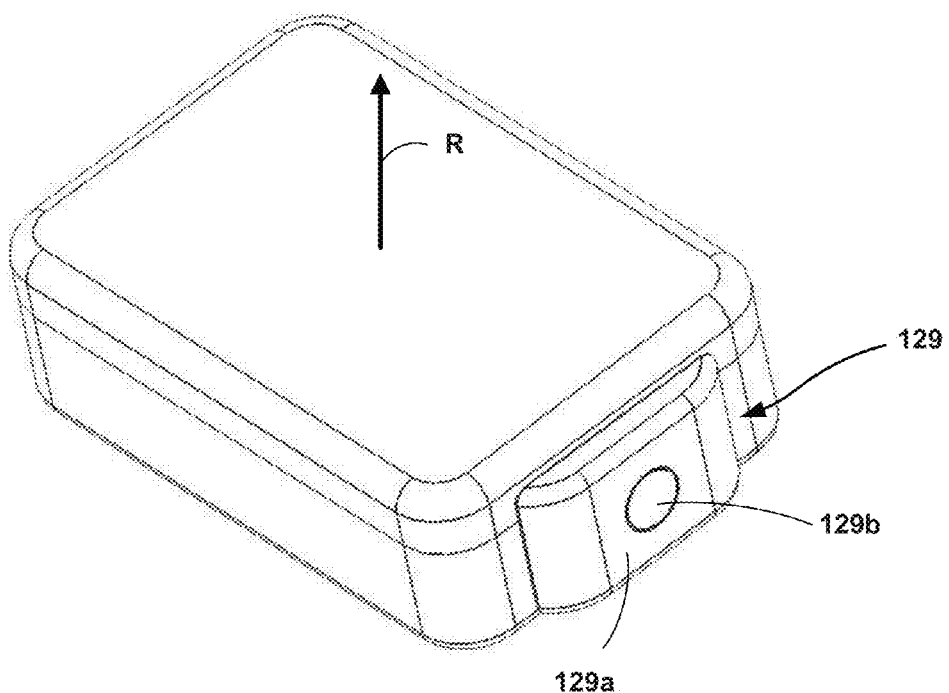
Figure 4H:
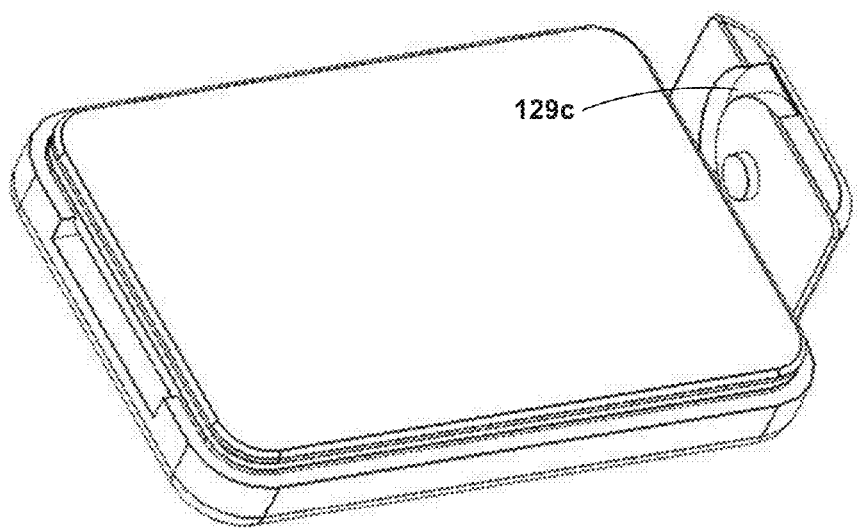

FIGS. 4G and 4H are perspective views of a control and power source module including battery release latch 129. Battery release latch 129 includes knob 129a, pivot 129b, and channel 129c. In FIGS. 4G and 4H, knob 129a is pivotably connected to the housing of the control and power source module at pivot 129b. The removable battery of the control and power source module of FIGS. 4G and 4H includes a post that protrudes from one end of the battery and is configured to be received in channel 129c. Latch 129 may be actuated to release the battery by rotating knob 129a about pivot 129b. In one example, knob 129a is rotated approximately 180 degrees about pivot 129b. Channel 129c is configured to push on the post protruding from the battery as knob 129a is rotated such that the battery is gradually released upward away from the housing. After rotating knob 129a completely, e.g. 180 degrees, the post in the battery may be released from channel 129c to release the battery from the housing of the control and power source module.

Figure 5:
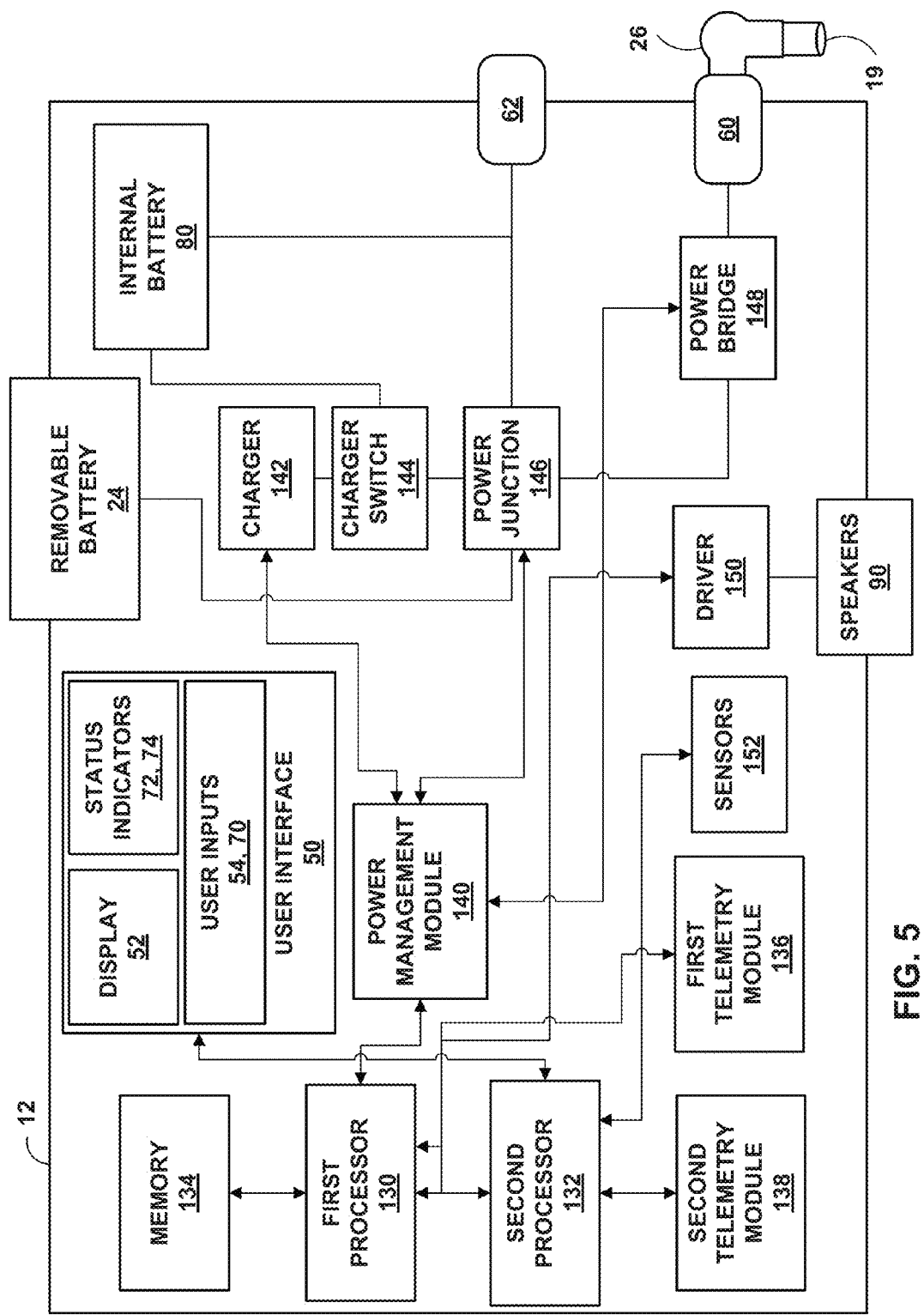
FIG. 5 is functional block diagram illustrating an example control and power source module according to this disclosure.

FIG. 5 is a functional block diagram illustrating components of an example of control and power source module 12, which includes removable battery 24, internal battery 90, pump cable port 60 connected to cable extension 19 via connector 26, external power source port 62, speakers 90, and a variety of electronics. The electronics of control and power source module 12 include first processor 130, second processor 132, memory 134, first telemetry module 136, second telemetry module 138, power management module 140, charger 142 and charger switch 144, power junction 146, and power bridge 148. Control and power source module 12 includes speakers 90 driven by driver 150 for emitting audible sounds, such as alarms to patient 20 or a caregiver, such as a clinician. As illustrated in the example of FIG. 5, control and power source module 12 may also include one or more sensors 152, including, e.g. motion or light sensors. In one example, sensors 152 includes an ambient light sensor that is configured to automatically adjust the contrast and/or brightness of display 52 of user interface 50 based on current ambient light conditions.

Control and power source module 12 is configured to provide uninterrupted power to components of a VAD, e.g. implanted pump 14, by employing one removable battery 24 as a primary power source and internal battery 80 as a back-up to bridge operation of the control and power source module components during recharge of removable battery 24. Internal battery 80 may be non-removably connected to control and power source module 12 in the sense that it is not configured to be removed and replaced by users during normal operation of the device. In some examples, internal battery 80 may, of course, be removed from control and power source module 12, e.g. by disassembling the device and disconnecting the internal battery from the internal circuitry of the device. In one example, one or both of removable battery 24 and internal battery 80 of control and power source module 12 may include, e.g., rechargeable lithium-ion (Li-ion), lithium polymer (Lipoly), nickel-metal hydride (NiMH), or nickel-cadmium (NiCd) battery cells. In one example, removable battery 24 includes rechargeable lithium-ion (Li-ion), nickel-metal hydride (NiMH), or nickel-cadmium (NiCd) battery cells, while internal battery 80 includes lithium polymer (Lipoly) battery cells.

Control and power source module 12 employs two power sources for redundancy and continuous operation. The primary power source is removable battery 24, which may be removed to recharge the battery, e.g. using a separate charging station. Internal battery 80 is generally non-removable and, in some examples, may be charged by either removable battery 24 or an external power source. Although control and power source module 12 is described as including removable battery 24 as the primary power source, the module also includes an adapter, external power source port 62 for a DC or AC source. An external power source connected to control and power source module 12 via port 62 may function not only to charge removable battery 24 and internal battery 80, but also as a third source of power for the device. In one example, such an external power source may be employed by control and power source module 12 over both removable battery 24 and internal battery 80 to power components of the device, as well as, e.g., implanted pump 14.

In examples according to this disclosure, in addition to connecting an external power source to control and power source module 12 as a third power source, removable battery 24 may be replaced by an external power source, including, e.g., an alternating or direct current (AC or DC respectively) power supply. In one such example, removable battery 24 may include an adapter to which the external power source may connect. As another alternative to the configuration illustrated in the example of FIG. 5, in the event that patient 20 desires a longer runtime between charges than removable battery 24 provides, control and power source 12 may be configured to have an enlarged removable battery connected to the device. In one example the enlarged removable battery may include twice the capacity of removable battery 24, but may also be significantly larger than battery 24. In any event, such an enlarged removable battery may be connected to control and power source module 12, e.g., via port 62 or though a port on removable battery 24.

Referring again to the example of FIG. 5, removable battery 24 and back-up internal battery 80 may be configured to have the same or different operational life times between successive charges. Additionally, removable battery 24 and back-up internal battery 80 may be rated for the same or different number of charge cycles before requiring replacement. In one example, removable battery 24 is configured to operate without recharge for a period of time in a range from approximately 4 hours to approximately 8 hours. In another example, removable battery 24 is configured to operate without recharge for a period of time approximately equal to 6 hours. In one example, internal battery 80 is configured to operate without recharge for a period of time in a range from approximately 30 minutes to approximately 2 hours. In one example, internal battery 80 is configured to operate without recharge for a period of time approximately equal to 1 hour. Employing a smaller internal battery 80 in control and power source module 12 may act to reduce the size, complexity, and cost of the device by removing the necessity for two full-size external batteries and a mechanical battery locking mechanism.

In one example, removable battery 24 is a 4S2P battery with four battery cells in series and two in parallel. Removable battery 24 may include a 3 amp-hour (Ah), 14.4 volt battery that is configured to operate in a range from approximately 500 to approximately 1000 recharging cycles before necessitating replacement. The operating lifetime of removable battery 24 over the approximately 500 to approximately 1000 recharging cycles may, in one example, equate to approximately one year. In one example, internal battery 80 is a 4S1P battery with four battery cells in series and one in parallel. Internal battery 80 may include a 100 milliamp-hour (mAh), 14.4 volt battery that is configured to operate for approximately 500 recharge cycles before necessitating replacement. As noted above, in examples according to this disclosure, internal battery 80 may be non-removably connected to control and power source module 12 in the sense that it is not configured to be removed and replaced by users during normal operation of the device. However, internal battery 80 may be removed from control and power source module 12, e.g. by disassembling the device and disconnecting the internal battery from the internal circuitry of the device in order to, e.g. replace the battery after it is no longer capable of holding a charge.

Control and power source module 12 includes power management module 140, which may be embodied as a variety of hardware and/or software components. In one example, power management module 140 may be one or more algorithms stored on memory 134 and executed by one or both of first processor 130 and second processor 132 of control and power source module 12. In any event, power management module 140 may be configured to manage the charging of the power sources of control and power source module 12, which of the power sources delivers powers to which components under different operational modes of the device, and communicate the status of the power sources to users, e.g. via one or more elements of user interface 50.

In one example of control and power source module 12 of FIG. 5, power management module 140 manages the charging of removable battery 24 and internal battery 80. For example, power management module 140 may control the operation of charger 142 and charger switch 144 to selectively charge one or both of removable battery 24 and internal battery 80. As noted above, control and power source module 12 includes external power source port 62 for connecting a third external power source to the device. In examples in which a third source is employed to power some or all of the components of control and power source module 12, the device may also employ flexible on-board charging techniques to provide users the ability to charge removable battery 24 and/or internal battery 80 while connected to the device. The third power source may be either an additional external battery or another external power source, e.g. a DC or AC external power source.

In one example, charger switch 144 may include a series of field-effect transistors (FETs) or other switches may allow one or more algorithms, e.g. stored on memory 134 and executed by power management module 140 of control and power source module 12 to control which of removable battery 24 or internal battery 80 is being charged at a given time and operational state of module 12. Additionally, in one example, power management module 140 may control charger 142 and/or charger switch 144 of control and power source module 12 to select either removable battery 24 or preferably the third external power source connected via port 62 to be employed for charging the other power sources of the device. The components associated with charger 142 and charger switch 144 of control and power source management module 14 are described in detail below with reference to the example circuits of FIG. 12. In one example, the same or different algorithms executed by power management module 140 to control which power source of control and power source module 12 is charged may also control the battery charge profile based on the state of removable battery 24 and internal battery 80 and, if connected via port 62, the third external power source.

When employed for use with a VAD or other MCS, power will be delivered by control and power source module 12 to implanted pump 14 primarily from removable battery 24. If battery 24 becomes depleted and requires removal and recharging, or, if the removable battery fails, power management module 140 of control and power source module 12 may automatically toggle to internal battery 80 or to an external power source connected to the device via port 62. Power management module 140 accomplishes this multiplexing of power sources associated with control and power source module 12 via power junction 146 in the example of FIG. 5.

In one example, power junction 146 may include a number of ideal diodes connected to removable battery 24, internal battery 80, and, if connected to control and power source module 12 via port 62, a third external power source. The ideal diodes of such an example of power junction 146 may be configured to automatically select the power source connected to control and power source module 12 with the highest voltage. In some examples of control and power source module 12, however, removable battery 24 and internal battery 80 may be configured to operate at approximately the same voltage. In such an example, a small amount of discharge of removable battery 24 may cause the operating voltage of the removable battery to fall below internal battery 80, which, without intervention would cause the ideal diodes of power junction 146 to select the internal battery after only a small amount of use of the removable battery. As such, in one example, in addition to the ideal diodes, power junction 146 may include a switch controlled by power management module 140 that may function to override the diodes, under some conditions, to select removable battery 24 to power components of control and power source module 12 and implanted pump 14 over internal battery 80.

Power management module 140 may control the switch of power junction 146 to select removable battery 24 to deliver power until the removable battery has been deleted to a threshold charge level, at which point, the power management module 140 may, e.g., deactivate the switch to allow the ideal diodes of power junction 146 to select internal battery 80. In one example, power management module 140 in conjunction with power junction 146 may be configured to select an external power source to power components of control and power source module 12 and implanted pump 14 over removable battery 24 and internal battery 80 whenever such a source is connected the device via port 62. In one example, power management module 140 in conjunction with power junction 146 may be configured to select the external power source regardless of the level of charge on removable battery 24 of internal battery 80. Additional details of power junction 146 is described in detail below with reference to the example circuits of FIG. 11.

Regardless of the particular configuration of power junction 146, power management module 140 may monitor the power sources connected to control and power source module 12 and selectively activate one of the power sources depending on the operating conditions of the device. For example, power management module 140 may monitor which of removable battery 24, internal battery 80, and an external power source are connected to control and power source module 12 to determine which of the connected sources should be used to power components of module 12, as well as implanted pump 14. Additionally, power management module 140 may monitor removable battery 24 and internal battery 80 to selectively activate one of the batteries based on the level of charge remaining on the batteries. For example, while removable battery 24 is being used, back-up internal battery 80 may be periodically tested by power management module 140 to determine a level of charge left in the internal battery. In the event removable battery 24 drops below a threshold charge level, power management module 140 may activate internal battery 80, provided, in some examples, the internal battery has at least a threshold amount of charge left.

Power management module 140, alone or in conjunction with power junction 146 may be configured to selectively activate one of the power sources of module 12 based on reasons other than the voltage delivered by the power source and the charge level remaining on the power source. For example, power management module 140 may be configured to selectively activate one of removable battery 24 or internal battery 80 based on the source and amplitude of a particular power requirement. As noted above, removable battery 24 and internal battery 80 may include rechargeable batteries with a variety of chemistries, including, e.g., lithium-ion (Li-ion), lithium polymer (Lipoly), nickel-metal hydride (NiMH), or nickel-cadmium (NiCd). In addition to removable battery 24 and internal battery 80 including particular chemistries, each of the batteries of control and power source module 12 may be configured with particular performance characteristics, based upon which, in some examples, power management module 140 may selectively activate one of the batteries.

In one example according to this disclosure, control and power source module 12, or another such device according to this disclosure, includes one energy dense power source and one power dense power source. For example, removable battery 24 of control and power source module 12 may be an energy dense power source and internal battery 80 may be a power dense power source. In another example, removable battery 24 of control and power source module 12 may be a power dense power source and internal battery 80 may be an energy dense power source. An energy dense power source may be a power source that is designed to maximize the total amount of energy per unit volume that the source can deliver. In the case of a rechargeable battery, an energy dense power source may be a battery that is designed to maximize the total amount of energy per unit volume that the source can deliver between successive charges. A power dense power source, on the other hand, may be a power source that is designed to maximize the power per unit volume that the source can deliver at any given time, e.g. to accommodate large power loads.

In one example, removable battery 24 of control and power source module 12 may be an energy dense power source including an energy density in a range from approximately 455 to approximately 600 watt-hours per liter (W-hr/L). In one example, internal battery 80 may be a power dense power source including a power density in a range from approximately 700 watts per liter (W/L) to approximately 6 kilowatts per liter (kW/L). In one example in which removable battery 24 of control and power source module 12 is an energy dense power source and internal battery 80 is a power dense power source, power management module 140 may be configured to selectively activate one of removable battery 24 or internal battery 80 based on the amplitude of a particular power requirement. For example, implanted pump 14 may have transient operating conditions which temporarily cause large spikes in the power drawn by the pump. In one example, starting implanted pump 14 may draw a significantly larger amount of power than running the pump at steady state, e.g. start-up may draw approximately 50 watts while steady state draws approximately 5 watts. In another example, transient physiological conditions of patient 20 may cause large power draws from pump 14. In examples including large power spikes in the power requirements of, e.g. implanted pump 14, power management module 140 may selectively activate internal battery 80, e.g. by controlling power junction 146, regardless of the charge level of removable batter 24, because the power dense internal battery may be better adapted for handling the power spike than the energy dense removable battery.

In addition to managing power source charging and selectively activating power sources for power delivery, as described in the foregoing examples, power management module 140 may also be configured to manage communicating the status of the power sources to users, e.g. via one or more elements of user interface 50. An example process by which power management module 140 of control and power source 12 may manage communicating the status of the power sources of the device to users is illustrated in the state diagram of FIG. 6. Functions and appearances of an example configuration of the elements of user interface 50 of control and power source module 12 are illustrated in FIGS. 7A-9C, some of which are described with reference to the state diagram of FIG. 6 by which power management module 140 of control and power source 12 manages communicating the status of the power sources of the device to users in one example according to this disclosure.

Figure 6:
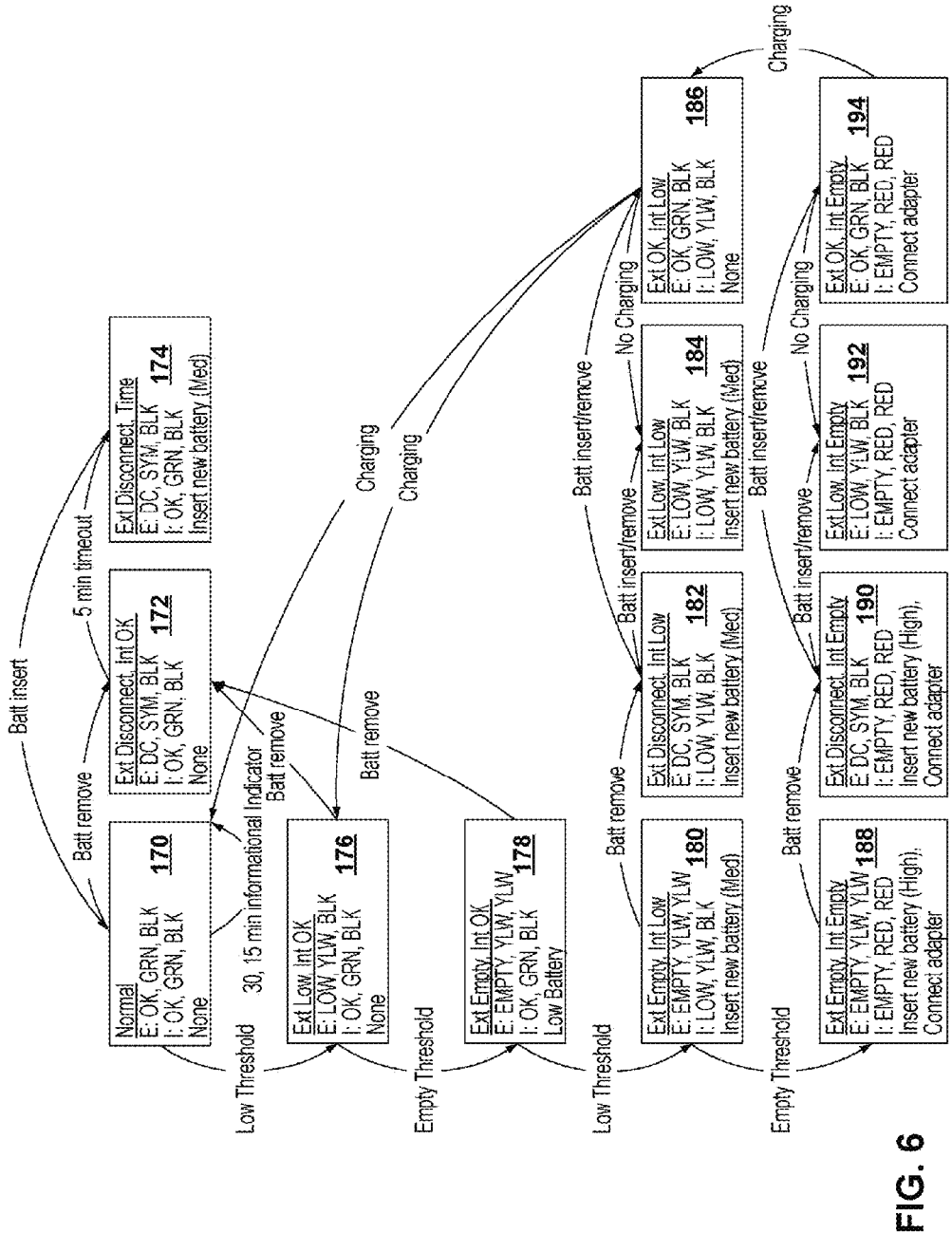
FIG. 6 is a state diagram representing a process by which the status of power sources of the control and power source module of FIG. 5 may be communicated to a user.

FIG. 6 illustrates states 170-194 of the power sources connected to control and power source module 12, e.g. removable battery 24, internal battery 80, and, in some examples, an external power source connected via port 62. The state diagram of FIG. 6 is organized such that movement between states from the left side to the right of the diagram indicates states in which removable battery 24 is disconnected from and reconnected to control and power source module 12.

Additionally, the state diagram of FIG. 6 is organized such that movement between states from the top to the bottom of the diagram indicates states in which one or both of one or both of removable battery 24 and internal battery 80 are progressively depleted to different threshold charge levels.

The state diagram of FIG. 6 uses a number of abbreviations. In FIG. 6, "batt" generally refers to battery. Each of states 170-194 include a state description, e.g. "Normal" for state 170, status and user interface indications related to each of removable battery 24 and internal battery 80, e.g. "E: OK, GRN, BLK" for removable battery 24 and "I: OK, GRN, BLK" for internal battery 80, and alarms communicated to users via user interface 50. With reference to the status and user interface indications related to each of removable battery 24 and internal battery 80, the abbreviations used in FIG. 6 have the following meanings. The first letter, e.g. E or I, refers to which of removable battery 24 or internal battery 80, respectively, the status and user interface indications relates. The first letter E, as well as the abbreviation Ext in the state description refers to an external battery, which in the example of FIG. 6 is equivalent to a removable battery, such as removable battery 24 of control and power source module 12. For both the removable battery 24 and internal battery 80, the status and user interface indications are the charge and operational state of the battery, the color of the alarm indication on user interface 50, and the color of the graphical representation of the battery on user interface 50. For example, in state 170, "E: OK, GRN, BLK" means that removable battery 24 is above a low charge level threshold and is operating properly (OK), the color of the alarm indication on user interface 50 is green (GRN), and the color of the graphical representation of the battery on user interface 50 is black (BLK).

In the state diagram of FIG. 6, alarm and battery representation color "YLW" stands for yellow and "RED" indicates the color red. In the event removable battery 24 is disconnected from control and power source module 12, the state of the battery is indicated in FIG. 6 as "DC," which stands for disconnected. Additionally, both removable battery 24 and internal battery 80 include three threshold charge levels, indicated by "OK, LOW, and EMPTY." The battery condition OK, as far as charge level is concerned, indicates that the battery to which the condition refers is above a threshold low charge level, while LOW indicates the battery is at a threshold low charge level, which may be a range of charge levels, and EMPTY indicates the battery is at a threshold empty charge level, which may also be a range of charge levels and which may be greater than zero charge. The threshold charge levels for removable battery 24 and internal battery 80 employed in examples according to this disclosure may be the same or different, in number as well as magnitude.

Starting in the upper right hand corner of the state diagram of FIG. 6, state 170 indicates a normal operational state for control and power source module 12. In state 170, removable battery 24 and internal battery 80 are both above a threshold low charge level, and there state is thus indicated in state 170 as OK. The indication in state 170 that removable battery 24 and internal battery 80 are both OK because the batteries are above a threshold low charge level does not necessarily mean that the batteries are fully charged and may occur regardless of whether control and power source module 12 is connected to an external power source to charge one or both of the batteries. For example, state 170 may occur when removable battery 24 is partially discharged, but the charge level of the battery is still above a low threshold level that may necessitate alerting the user and recharging. Similarly, state 170 may occur when internal battery 80 is partially discharged, but the charge level of the battery is still above a low threshold level that may necessitate alerting the user and recharging. State 170 may also occur when both removable battery 24 and internal battery 80 are partially discharged, but the charge levels of both the batteries are still above a low threshold level that may necessitate alerting the user and recharging. In another example, state 170 may occur when both removable battery 24 and internal battery 80 are fully charged and when an external power source is connected to control and power source module 12, as long as both batteries are also above a threshold low charge level.

Figure 7A:
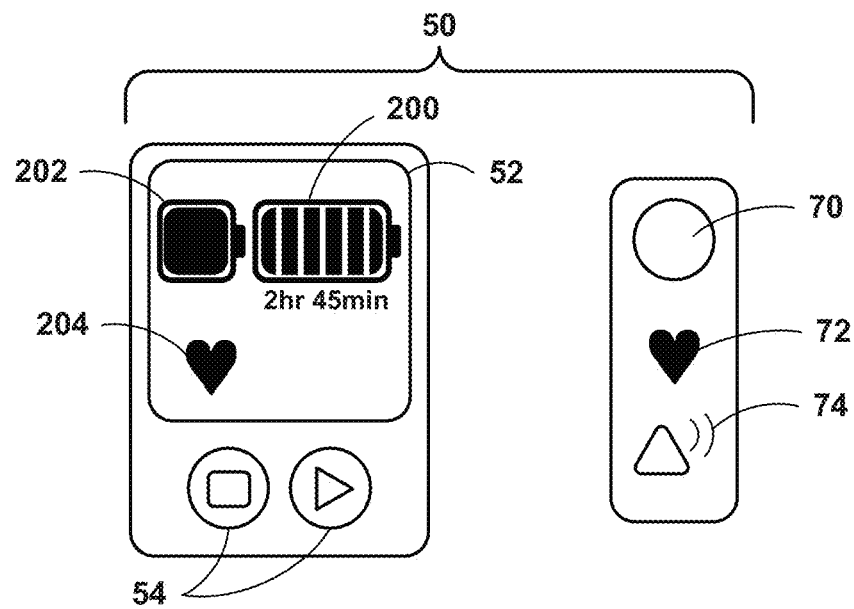
FIGS. 7A-10B illustrate a number of functions associated with elements of an example user interface of the control and power source module of FIG. 5.
Figure 7B:
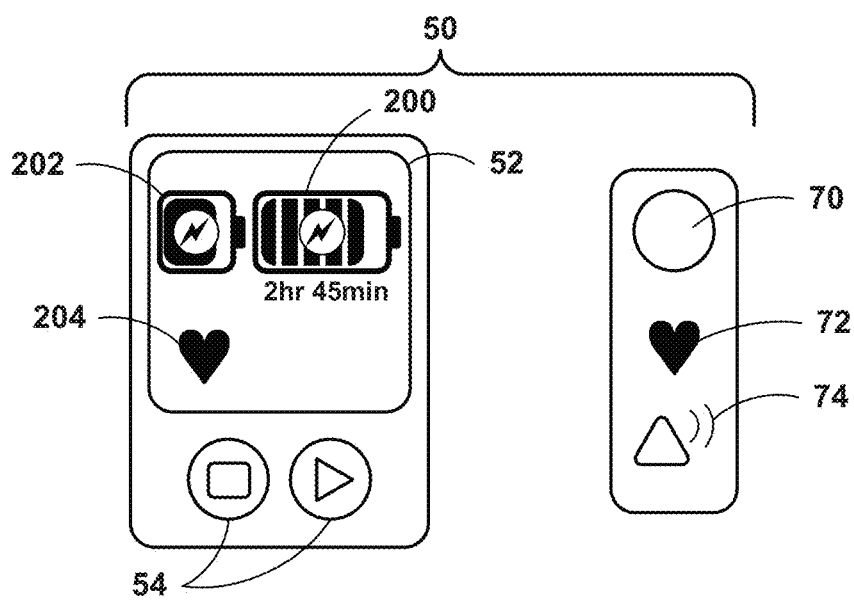

FIGS. 7A and 7B illustrate examples of the manner in which power management module 140 may control user interface 50 when control and power source module 12 is in the normal operational state indicated by state 170 in FIG. 6. As described above, user interface 50 of control and power source module 12 includes display 52, input buttons 54, as well as mute button 70 and status indicators 72 and 74. In the examples of FIGS. 7A and 7B, display 52 includes removable battery icon 200, internal battery icon 202, and status indicator 204. Also in the examples of FIGS. 7A and 7B, as well as FIGS. 8-10B, input buttons 54 are encoded with two different icons, one a rectangular icon and the other a triangular icon. In these examples of user interface 50, input buttons 54 correspond to two main functions for interacting with control and power source module 12. Input button 54 encoded with the rectangular icon may function as a "home" button that, when activated by a user, navigates to a default screen presented on display 52 of user interface 50. Input button 54 encoded with the triangular icon may function as a "next" button that, when activated by a user, toggles to the next screen in a series of possible screens that may be presented on display 52 of user interface 50.

FIG. 7A illustrates an example in which removable battery 24 and internal battery 80 of control and power source module 12 are fully charged, as indicated by the amount of fill in removable battery icon 200 and internal battery icon 202 associated with removable and internal batteries 24 and 80, respectively. In FIG. 7A, neither removable battery 24 or internal battery 80 are currently being charged, e.g. either by an external power source connected to control and power source module 12 via port 62 or, in the case of internal battery 80 by removable battery 24.

As the conditions of removable battery 24 and internal battery 80, as well as various other components of control and power source module 12, in FIG. 7A indicate a normal operating state corresponding to state 170 from FIG. 6, status indicator 204 on display 52 presents a heart icon. Additionally, status indicator 72 is activated by control and power source module 12 to illuminate the heart shaped indicator. Finally, because the conditions of removable battery 24 and internal battery 80, as well as various other components of control and power source module 12, indicate a normal operating state that does not necessitate any alarms, display 52 does not present any alarm icons and status indicator 74 associated with alarm conditions is not illuminated.

FIG. 7B illustrates an example in which removable battery 24 and internal battery 80 of control and power source module 12 are less than fully charged, but are above a threshold low charge level, as indicated by the amount of fill in graphics 200 and 202 associated with removable and internal batteries, respectively. Additionally, in FIG. 7B, both removable battery 24 and internal battery 80 are currently being charged, as indicated by charging icon 206 overlaid on removable battery icon 200 and internal battery icon 202. As described above, removable battery 24 may be charged while connected to control and power source module 12 by an external power source connected to module 12 via port 62. Additionally, internal battery 80 may be charged by the external power source or removable battery 24. As the conditions of removable battery 24 and internal battery 80, as well as various other components of control and power source module 12, in FIG. 7B indicate a normal operating state corresponding to state 170 from FIG. 6, as with the state of the device illustrated in FIG. 7A, status indicator 204 on display 52 presents a heart icon, status indicator 72 is illuminated, and status indicator 74 associated is not illuminated.

In both FIGS. 7A and 7B, power management module 140 may present control battery icon 200 and internal battery icon 202 in black, while the charge level of removable battery 24 and internal battery 80 indicated by the fill in battery icon 200 and internal battery icon 202, as well as status indicator 204 on display 52 and status indicator 72 may be presented in green, as indicated by state 170 in FIG. 6.

Referring again to FIG. 6, moving from state 170 to the right, state 172 indicates that removable battery 24 is disconnected from control and power source module 12, while internal battery 80 is above a threshold low charge level. State 172 indicates the disconnection of removable battery 24 as DC. In the example state diagram of FIG. 6, whenever removable battery 24 is disconnected from control and power source module 12, the alarm color is indicated not by a color but by a symbol, which is abbreviated in the states of FIG. 6 as "SYM." An example of this disconnection symbol is illustrated in the example of user interface 50 in FIG. 8. Removable battery 24 may disconnect from control and power source module 12 for a variety of reasons. In one example, a user, e.g. patient 20 may have more than one removable battery that may be connected to control and power source module 12 such that it is possible to always or nearly always have a fully charged removable battery that can be swapped for a discharged battery. In another example, removable battery 24 may malfunction and necessitate complete replacement. In another example, removable battery 24 may reach its maximum number of charge cycles such that it is no longer able to hold a charge and thus necessitates complete replacement.

Figure 8:
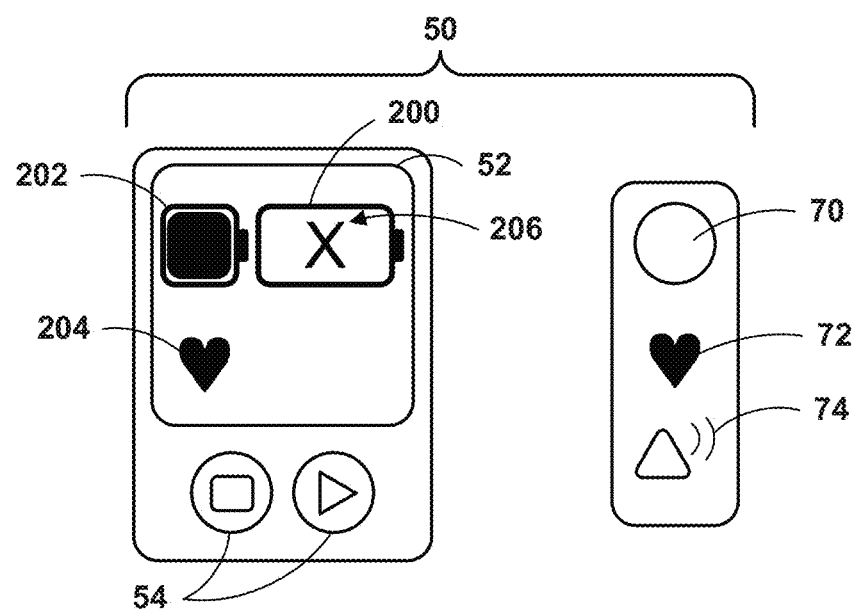

FIG. 8 illustrates an example of the manner in which power management module 140 may control user interface 50 when control and power source module 12 is in the disconnected removable battery state indicated by state 172 in FIG. 6. In the example of FIG. 8, display 52 includes removable battery icon 200, internal battery icon 202, status indicator 204, and disconnect symbol 206. FIG. 8 illustrates an example in which removable battery 24 is disconnected from control and power source module, as indicated by disconnect symbol 206 overlaid on removable battery icon 200. Internal battery 80 of control and power source module 12, as indicated in state 172 in FIG. 6, is above a threshold low charge level, and, in particular in FIG. 8 is fully charged, as indicated by the amount of fill in internal battery icon 202. In FIG. 8, neither removable battery 24 or internal battery 80 are currently being charged, e.g. either by an external power source connected to control and power source module 12 via port 62 or, in the case of internal battery 80 by removable battery 24.

As the conditions of internal battery 80, as well as various other components of control and power source module 12, in FIG. 8 do not indicate any alarm conditions, power management module 140 may present status indicator 204 on display 52 as a heart icon. Additionally, status indicator 72 is activated by power management module 140 to illuminate the heart shaped indicator. Finally, because the condition of control and power source module 12 does not the necessity for any alarms, display 52 does not present any alarm icons and status indicator 74 associated with alarm conditions is not illuminated.

In FIG. 8, power management module 140 may present battery icon 200, internal battery icon 202, and disconnect symbol 206 in black, while the charge level of internal battery 80 indicated by the fill in internal battery icon 202, as well as status indicator 204 on display 52 and status indicator 72 may be presented in green, as indicated by state 172 in FIG. 6.

Referring again to FIG. 6, moving from state 172 to the right, state 174 indicates that disconnection timeout has been reached, which causes power control module 140 to trigger an alarm instructing a user of control and power source module 12 to reconnect removable battery 24 or another such power source to the device. The disconnection timeout in the example of FIG. 6 is indicated as five minutes such that leaving removable battery 24 disconnected from control and power source module 12 for more than five minutes will trigger a battery reconnection alarm. However, in other examples according to this disclosure, the disconnection timeout may be more or less time than in the example of FIG. 6. For example, the disconnection timeout may be equal to ten minutes such that power management module 140 will trigger a battery reconnection alarm after leaving removable battery 24 disconnected from control and power source module 12 for more than ten minutes. In one example of state 174, power management module 140 may control user interface 50 to present instructions to a user of control and power source module 12 on display 52 to insert a new or recharged removable battery after the disconnection timeout has been reached. In another example, power management module 140 may also control speaker driver 150 and speakers 90 to cause the speakers to issue and audible sound.

In the example of FIG. 6, moving down from normal state 170 to state 188 the charge levels of removable battery 24 and internal battery 80 get progressively lower. Additionally, moving down from normal state 170 to state 188 the alarms issued by power management module 140 and the instructions associated with such alarms increase in severity, e.g. by changing graphical symbols, color, and/or the amplitude of audible sounds issued by speakers 90 of control and power source module 12. In state 176, removable battery 24 has reached a threshold low charge level, while internal battery 80 remains above a threshold low charge level. In state 178, removable battery 24 has reached a threshold empty charge level, while internal battery 80 remains above a threshold low charge level. In state 178, because removable battery 24 has reached a threshold empty charge level, power management module 140 of control and power source module 12 triggers a low battery alarm. In one example of state 18, user interface 50 may illuminate status indicator 74 and present status indicator 204 on display 52 as an alarm icon. Additionally, user interface 50 may present a user of control and power source module 12 an indication on display 52 of the low battery charge level, e.g. by coloring part or all of a removable battery icon on display 52 yellow. In state 180, removable battery 24 has reached a threshold empty charge level and internal battery 80 has reached a threshold low charge level. Finally, in state 188, removable battery 24 and internal battery 80 have both reached a threshold empty charge level.

In addition to the charge levels of removable battery 24 and internal battery 80 progressively lowering moving down from state 170 to state 188 in the example of FIG. 6, the alarms issued by power management module 140 and the instructions associated with such alarms increase in severity, e.g. by changing graphical symbols and colors associated with elements of user interface 50 and/or changing the amplitude of audible sounds issued by speakers 90 of control and power source module 12. For example, while the alarm associated with the empty removable battery and ok internal battery state 178 may include user interface 50 presenting a user of control and power source module 12 an indication on display 52 of the low battery charge level, e.g. by coloring part or all of a removable battery icon on display 52 yellow, the alarm associated with the empty removable battery and low internal battery state 180 may include presenting the user instructions on display 52 to insert a new battery. In one such example, the priority of the alarm instructing the user to insert a new battery, as indicated, e.g., by the amplitude of a sound issued by speakers 90, may be medium.

In the empty removable battery and empty internal battery state 188, in contrast to both states 178 and 180, power management module 140 may further increase the severity of the alarms presented to the user of control and power source module. As indicated in FIG. 6, for example, power management module 140 may color alarms and battery icons presented by user interface 50 on display 52 red and may also issue instructions to the user to insert a new battery and/or connect control and power source module 12 to an external power source, e.g. via port 62. In one such example, the priority of the alarm instructing the user to insert a new battery and/or connect control and power source module 12 to an external power source, as indicated, e.g., by the amplitude of a sound issued by speakers 90, may be high.

Referring again to state 180 in the example of FIG. 6, moving to the right from state 180 indicates situations in which internal battery 80 maintains a charge at a threshold low charge level, but the state of removable battery 24 changes, including disconnecting and reconnecting or replacing the removable battery. In state 182, removable battery 24 is disconnected from control and power source module 12 and internal battery 80 is at a threshold low charge level. In state 182, power management module 140 may issue an alarm to a user of control and power source module 12, including, e.g., controlling user interface 50 to present a symbol associated with a removable battery icon indicating that battery 24 has been disconnected and to color part or all of an internal battery icon on display 52 yellow. Power management module 140 may also present instructions on display 52 to insert a new battery, as well as indicating the priority of the alarm instructing the user to insert a new battery as medium by, e.g., controlling speakers 90 to issue an audible sound at a particular amplitude.

In state 184, a removable battery at a threshold low charge level is connected to control and power source module 12 and internal battery 80 is at a threshold low charge level. In one example of state 184, removable battery 24 has been recharged to the threshold low charge level and reconnected to control and power source module 12. In another example, however, removable battery 24 has been replaced by another removable battery, which is at the threshold low charge level and which is connected to control and power source module 12. In state 184, power management module 140 may issue an alarm to a user of control and power source module 12, including, e.g., controlling user interface 50 to color part or all of a removable battery icon and an internal battery icon on display 52 yellow, present instructions on display 52 to insert a new battery, as well as indicating the priority of the alarm instructing the user to insert a new battery as medium by, e.g., controlling speakers 90 to issue an audible sound at a particular amplitude.

In state 186, a removable battery above a threshold low charge level is connected to control and power source module 12 and internal battery 80 is at a threshold low charge level. In one example of state 186, removable battery 24 has been recharged to above the threshold low charge level and reconnected to control and power source module 12. In another example, however, removable battery 24 has been replaced by another removable battery, which is charged above the threshold low charge level and which is connected to control and power source module 12. In state 186, power management module 140 may issue an alarm to a user of control and power source module 12, including, e.g., controlling user interface 50 to color part or all of a removable battery icon green to indicate that the removable battery is above the threshold low charge level and controlling user interface 50 to color part or all of an internal battery icon on display 52 yellow to indicate that internal battery 80 is still at the threshold low charge level.

Referring again to state 188 in the example of FIG. 6, moving to the right from state 188 indicates situations in which internal battery 80 maintains a charge at a threshold empty charge level, but the state of removable battery 24 changes, including disconnecting and reconnecting or replacing the removable battery. In state 190, removable battery 24 is disconnected from control and power source module 12 and internal battery 80 is at a threshold empty charge level. In state 190, power management module 140 may issue an alarm to a user of control and power source module 12, including, e.g., controlling user interface 50 to present a symbol associated with a removable battery icon indicating that battery 24 has been disconnected and to color part or all of an internal battery icon on display 52 red. Power management module 140 may also present instructions on display 52 to insert a new battery and/or connect control and power source module 12 to an external power source, as well as indicating the priority of the alarm instructing the user to insert a new battery as high by, e.g., controlling speakers 90 to issue an audible sound at a particular amplitude, e.g. a higher amplitude than a sound issued for a medium priority alarm.

In state 192, a removable battery at a threshold low charge level is connected to control and power source module 12 and internal battery 80 is at a threshold empty charge level. In one example of state 192, removable battery 24 has been recharged to the threshold low charge level and reconnected to control and power source module 12. In another example, however, removable battery 24 has been replaced by another removable battery, which is at the threshold low charge level and which is connected to control and power source module 12. In state 192, power management module 140 may issue an alarm to a user of control and power source module 12, including, e.g., controlling user interface 50 to color part or all of a removable battery icon yellow and an internal battery icon on display 52 red, as well as present instructions on display 52 to connect control and power source module 12 to an external power source.

In state 194, a removable battery above a threshold low charge level is connected to control and power source module 12 and internal battery 80 is at a threshold empty charge level. In one example of state 194, removable battery 24 has been recharged to above the threshold low charge level and reconnected to control and power source module 12. In another example, however, removable battery 24 has been replaced by another removable battery, which is charged above the threshold low charge level and which is connected to control and power source module 12. In state 194, power management module 140 may issue an alarm to a user of control and power source module 12, including, e.g., controlling user interface 50 to color part or all of an internal battery icon on display 52 red to indicate that internal battery 80 is still at the threshold empty charge level. As internal battery 80 is still at the threshold empty charge level, power management module 140 may also present instructions on display 52 to connect control and power source module 12 to an external power source to charge the internal battery above the empty threshold without depleting the removable battery.

The foregoing example of the state diagram of FIG. 6 is described by beginning with state 170 in the upper right hand corner of the diagram and moving in a number of directions from that state. However, the selection of state 170 as a starting point as well as the movements from there to other states described below is arbitrary and does not indicate any required order for the states of control and power source module 12. The arrows in the state diagram of FIG. 6 illustrate that movement between the various states of control and power source module 12 may occur as a result of a number of different factors, including, e.g. removing or inserting a removable battery, depleting or increasing the charge level of one or both of removable battery 24 and internal battery 80 to a number of different thresholds, and charging one or both of removable battery 24 and internal battery 80.

Figure 9A:
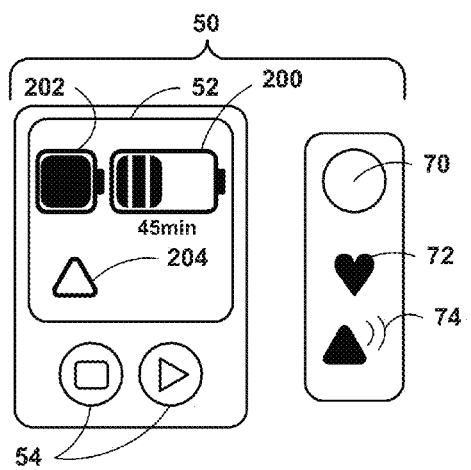

FIGS. 9A-10B illustrate a number of additional example functions and appearances of an example configuration of the elements of user interface 50 of control and power source module 12. FIGS. 9A-C illustrate a number of examples of user interface 50 by which power management module 140 indicates three states of control and power source module 12 with removable battery 24 and internal battery 80 at varying charge levels. In the examples of FIGS. 9A-C, neither removable battery 24 or internal battery 80 are currently being charged, e.g. either by an external power source connected to control and power source module 12 via port 62 or, in the case of internal battery 80 by removable battery 24.

FIG. 9A illustrates examples of the manner in which power management module 140 may control user interface 50 when removable battery 24 is at a threshold low charge level and internal battery 80 is above a threshold charge level. In one example of the state represented by user interface 50 in FIG. 9A, power management module 140 may present status indicator 204 on display 52 as an alarm icon. In the example of FIG. 9A, status indicator 204 indicates the lowest level alarm condition by outlining the alarm icon and presenting no emphasis symbols. Status indicator 72 is also deactivated by power management module 140 such that the heart shaped indicator is not illuminated and status indicator 74 is illuminated to indicate the alarm condition. In the example of FIG. 9A, status indicator 204 indicates the lowest level alarm condition by illuminating the triangle portion of the indicator without illuminating the emphasis symbols indicated as two curved lines in FIG. 9A. In one example, power management module 140 may present removable battery icon 200 and internal battery icon 202 in black, while the charge level of removable battery 24 indicated by the fill in battery icon 200, as well as status indicator 204 on display 52 and status indicator 74 may be presented in yellow. Power management module may present the charge level of internal battery 80 indicated by the fill in battery icon 202 as green to indicate, in contrast to removable battery 24, the internal battery is above a threshold low charge level.

Figure 9B:
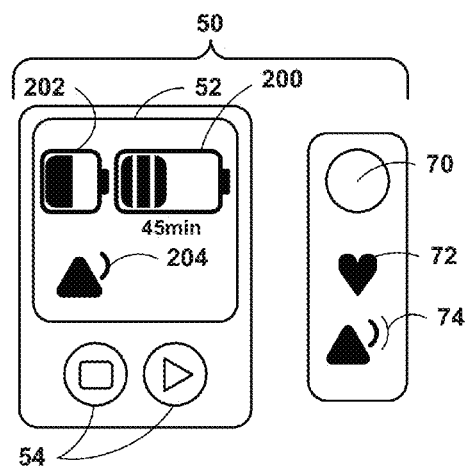

FIG. 9B illustrates examples of the manner in which power management module 140 may control user interface 50 when both removable battery 24 and internal battery 80 are at a threshold low charge level. In one example of the state represented by user interface 50 in FIG. 9B, power management module 140 may present status indicator 204 on display 52 as an alarm icon. In the example of FIG. 9B, status indicator 204 indicates a medium level alarm condition by filling the alarm icon and presenting one emphasis symbol represented by a thickened curved line. Status indicator 72 is also deactivated by power management module 140 such that the heart shaped indicator is not illuminated and status indicator 74 is illuminated to indicate the alarm condition. In the example of FIG. 9B, status indicator 204 indicates the medium level alarm condition by illuminating the triangle portion of the indicator and illuminating one of the two emphasis symbols indicated as two curved lines in FIG. 9B. In one example, power management module 140 may present removable battery icon 200 and internal battery icon 202 in black, while the charge level of removable battery 24 and internal battery 80 indicated by the fill in battery icons 200 and 202, as well as status indicator 204 on display 52 and status indicator 74 may be presented in yellow.

Figure 9C:
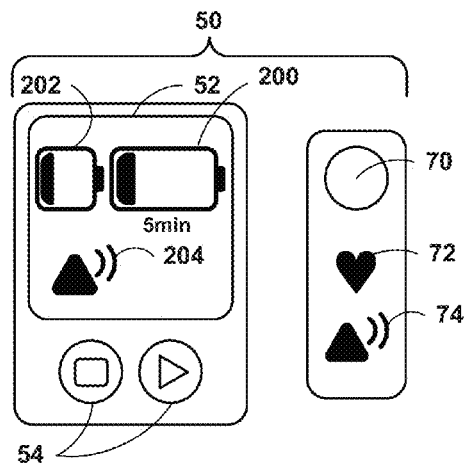

FIG. 9C illustrates examples of the manner in which power management module 140 may control user interface 50 when both removable battery 24 and internal battery 80 are at a threshold empty charge level. In one example of the state represented by user interface 50 in FIG. 9C, power management module 140 may present status indicator 204 on display 52 as an alarm icon. In the example of FIG. 9C, status indicator 204 indicates a high level alarm condition by filling the alarm icon and presenting two emphasis symbols represented by two thickened curved lines. Status indicator 72 is also deactivated by power management module 140 such that the heart shaped indicator is not illuminated and status indicator 74 is illuminated to indicate the alarm condition. In the example of FIG. 9C, status indicator 204 indicates the high level alarm condition by illuminating the triangle portion of the indicator and illuminating both emphasis symbols indicated as two curved lines in FIG. 9C. In one example, power management module 140 may present removable battery icon 200 and internal battery icon 202 in black, while the charge level of removable battery 24 and internal battery 80 indicated by the fill in battery icons 200 and 202, as well as status indicator 204 on display 52 and status indicator 74 may be presented in red.

Figure 10A:
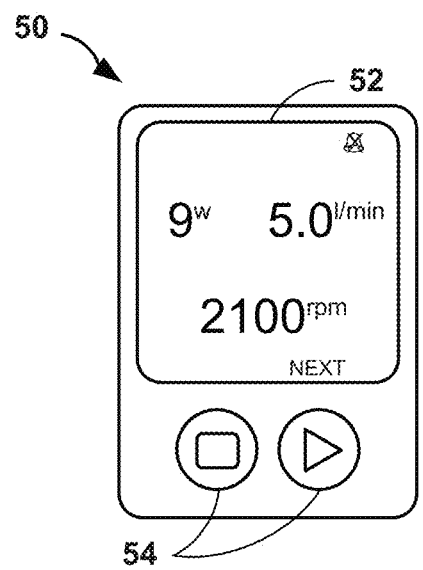
Figure 10B:

FIGS. 10A and 10B illustrate screens that may be presented by display 52 of user interface 50 in addition to the screens indicating battery charge state and alarm conditions. FIG. 10A illustrates an example in which power management module 140 presents various parameters related to the implanted pump 14. As described below, power management module 140, in conjunction with power bridge 148 illustrated in FIG. 5, may be configured to detect the operational parameters of the motor driving implanted pump 14. In FIG. 10A, power management module 140 presents the current power drawn by the motor driving pump 14 in watts (w), the current throughput of the pump in liters per minute (l/min), and the current angular velocity of the pump motor in revolutions per minute (rpm). FIG. 10B illustrates an example in which power management module 140 presents a description of an alarm the module issues to a user of control and power source module 12, as well as instructions for remedial actions that may be performed by the user to take the control and power source module out of the alarm state.

Referring to FIGS. 7A, 7B, and 9A-10B, power management module 140 not only presents users of control and power source module 12 with estimations of the amount of charge remaining in removable battery 24 and internal battery 80, but also provides an estimate of the amount of time the batteries will continue to operate before requiring replacement or recharging. For example, in FIGS. 7A and 7B, power management module 140 calculates the time remaining on the battery charges as two hours and forty five minutes, which is presented by user interface 50 on display 52 just below removable battery icon 200. In FIGS. 9A and 9B, power management module 140 calculates the time remaining on the battery charges as forty five minutes, which is presented by user interface 50 on display 52 just below removable battery icon 200. In one example, power management module 140 may calculate and user interface 50 may present the time remaining on the charge of removable battery 24. In another example, power management module 140 may calculate and user interface 50 may present the time remaining on the charge of internal battery 80. In another example, power management module 140 may calculate and user interface 50 may present the total time remaining on the charges of both removable battery 24 and internal battery 80. In another example, power management module 140 may calculate the time remaining on the charges of each of removable battery 24 and internal battery 80, which user interface may present separately on display 52.

Power management module 140 may use a number of different types of estimations and/or assumptions to calculate time remaining on the battery charges for control and power source module 12. In one example, power management module 140 may assume a default nominal power draw from the components of control and power source module 12 and implanted pump 14 and calculate the time remaining on the battery charges based on the default power requirement and the amount of charge left on removable battery 24 and internal battery 80. In another example, power management module 140 may track and store the power drawn by the components of control and power source module 12 and implanted pump 14 and average the power requirements over time. Power management module 140 may then calculate the time remaining on the battery charges based on the average historical power requirement and the amount of charge left on removable battery 24 and internal battery 80.

Referring again to FIG. 5, in addition to the redundant power source architecture described above, control of control and power source module 12 also includes dual processors 130, 132 and two telemetry modules 136, 138, both which elements of the device of FIG. 5 may be configured for redundant and/or complementary operation. Control and power source module 12 may employ first and second processors 130, 132 to provide error protection and redundant operation in the event one processor malfunctions. Additionally, first and second processors 130, 132 may be configured to power different components of control and power source module 12 and to further improve power management achieved by the device. In this sense, the use of first and second processors 130, 132 may be controlled by power management module 140, which, as noted above, may, in some examples, be embodied as one or both of processors 130, 132 and memory 134.

In one example employing error protection and redundancy techniques, first and second processors 130, 132 are configured to periodically test each other to detect malfunctions and/or failures. In the event one of first and second processors 130, 132 malfunctions or fails, the other of the processors may shut down the malfunctioning processor and assume management/control of any of the components of control and power source module 12 and/or implanted pump 14 previously handled by the malfunctioning processor. Additionally, the one of first and second processors 130, 132 that is still operating properly may trigger an alarm to alert a user of control and power source module 12 to the processor error/failure. For example, the one of first and second processors 130, 132 that is still operating properly may control display 52 of user interface 50 to present a message to the user of control and power source module 12, which the processor may retrieve, e.g., from memory 134.

In addition to error protection and redundancy techniques, first and second processors 130, 132 may be configured to manage and control different components of control and power source module 12 and one of the two may be configured to manage and control implanted pump 14. In the example of FIG. 5, first processor 130 is communicatively connected to memory 134, first telemetry module 136, power management module 140, and speaker driver 150. Power management module 140, connected to and associated with first processor 130, is communicatively connected to charger 142, power junction 146, and power bridge 148. In the example of FIG. 5, therefore, first processor 130, by default, is configured to control and manage implanted pump 14 via power management module 140 and power bridge 148. Second processor 132, on the other hand, is connected to memory 134, second telemetry module 138, sensors 152, and user interface 50. Thus, the control and management of control and power source module 12 is split between first processor 130 and second processor 132. The connection lines illustrated between components of control and power source module 12 in FIG. 5 are not meant to represent the only connections in the device. For example, in the event that first processor 130 malfunctions or fails, second processor 132 may take over control and management of implanted pump 14 via power management module 140 and power bridge 148.

In order to provide redundant operation of implanted pump 14, both first and second processors 130, 132 are configured to control and manage the pump in the event the other processor malfunctions or fails. However, first and second processors 130, 132 may not be, in some examples, exactly the same. For example, one of first and second processors 130, 132 may have lower power requirements than the other processor to further decrease the power loads on removable batter 24 and internal battery 80 of control and power source module 12. In any event, splitting the control and management of control and power source module 12 between first processor 130 and second processor 132 enables some of the components of the device to be shut down when not in use, which may, in turn, significantly decrease the power requirement of the electronics of the device. Thus, although control and power source module 12 may be designed to maximize space utilization and minimize the size of the device and although two processors may take up more space and weighs more than one, employing first and second processors 130, 132 may effectively reduce the power requirements enough that the size and capacity of removable battery 24 and internal battery 80 are also reduced.

In one example, first processor 130 is configured to control implanted pump 14 via power bridge 158, first telemetry module 136, power management module 140, and speaker driver 150. Second processor 132 is configured to control user interface 50, second telemetry module 138, and sensors 152. However, only a limited number of these components of control and power source module 12 are required be running all or even most of the time, which are primarily those affecting or relating to operation of implanted pump 14. As such, first processor 130 and second processor 132 may be configured to shut down one or more of the components they control in the event they are not in use. For example, second processor 132 may be configured to shut down user interface 50 and second telemetry module 138 when these components of control and power source module 12 are not in use. Additionally, in this example, second processor 132 does not control any components related to implanted pump 14 or any other component that must operate uninterrupted. As such, second processor 132 may be shut down. In such examples in which second processor 132 is shut down, in the event a component controlled by the processor needs to operate, e.g. a user calls on an element of user interface 50, first processor 130 may be configured to detect this activity and wake-up second processor 132. Additionally, in order to continue to provide error protection and redundancy, first processor 130 may be configured to periodically wake-up second processor 132, which, in turn, may then check the first processor for any malfunctions or failures. In another example, second processor 132 may be configured to periodically wake itself up to test first processor 130 for errors or failures.

In accordance with foregoing example split of control between first and second processors 130, 132, first processor 130 may store data on and retrieve data from memory 134 related to the operation of pump 14, as well as, e.g., speakers 90. In particular, first processor 130 may, e.g., retrieve information stored on memory 134 related to parameters for controlling pump 14 to pump blood through heart 30 of patient 20. In some examples, pump 14 may include an electric motor that drives operation of the pump to draw blood from left ventricle 36 and deliver it to aorta 38. For example, pump 14 may include any number of types of three-phase direct current (DC) or alternating current (AC) motors that are controlled by first processor 130 based on parameters including, e.g., motor speed (RPM) and power range (nominal, high, max power in Watts), retrieved from memory 134.

First processor 130 may also receive feedback from pump 14 or other devices including, e.g., removable battery 24 and internal battery 80 and store data related to the operation of the devices on memory 134. In one example, first processor 130 measures voltage levels going to the phases of the motor of pump 14 and the current that is returning on these phases. First processor 130 may use this voltage and current information from pump 14, as well as characteristics of the pump, e.g. winding resistance and inductance to estimate the speed and the torque of the pump. First processor 130 may then execute a control loop that sets the speed of pump 14, which then sets the pump torque. The torque setting defines how much current first processor 130 delivers to pump 14. In another example, first processor 130, e.g. as part of power management module 140 monitors the level of charge in each of removable battery 24 and internal battery 80 and controls status user interface 50 to indicate to patient 20 how much charge remains in each battery, e.g. graphically on display 52.

In some examples, control and power source module 12 is configured as a generic controller capable of controlling multiple types of pumps that include multiple types of motors. Generally speaking, many motors employed in implantable pumps of VADs will be able to be driven using a 3-phase bridge incorporated into control and power source module 12. The electronics of control and power source module 12 may be designed to drive and provide sensorless speed or torque control of virtually any permanent magnet motor. Many control algorithms may be used, including, e.g., a field oriented control (FOC) algorithm. Such algorithms, however, require some information about the motor parameters to be effective, such as the number of poles, the coil resistance, the coil inductance, as well as torque and speed constants. VAD controllers are commonly configured by selecting a set of motor parameters that work for a particular type or manufacturer motor. However, in examples of control and power source module 12 described in this disclosure, the module, and, in particular, first processor 130 may be configured to control a number of different types of motors by selecting a set of parameters that provide acceptable performance for all of the motors, instead of optimizing the parameters for a single motor.

In another example, first processor 130 of control and power source module 12 discovers the kind of motor that drives pump 14 to provide a plug-and-play type interface that allows control and power source module 12 to adapt control parameters of pump 14 to the particular type of motor driving the pump. In some examples, each motor type may be assigned a unique identifier and first processor 130 may query pump 14 for this identifier. First processor 130 may then retrieve a set of motor parameters associated with identifier from memory 134. In another example, first processor 130 may execute an adaptive algorithm stored in memory 134 that determines the operational parameters of the motor driving pump 14 once control and power source module 12 is connected to the specific motor by cable 18. Such an adaptive algorithm may use the motor driver and sense circuitry to directly or indirectly measure the needed motor parameters.

In another example, one or more of the foregoing functions related to the operation of implanted pump 14 may be executed by second processor 132. For example, in the event first processor 130 malfunctions or fails, second processor 132 may be configured to take over control of implanted pump 14.

Memory 134 of control and power source module 12 is a computer-readable storage medium that may be used to store data including instructions for execution by first and second processors 130, 132 or a processor of another device, such as, but not limited to, data related to the operation of pump 14 to assist heart 30 of patient 20. In some examples, memory 134 may store pump programs specific to, e.g., a particular pump motor that is controlled by first processor 130 to drive pump 14. In another example, memory 134 may store data related to power management functions executed by power management module 140. For example, memory 134 may store threshold charge level values associated with different threshold charge levels for one or both of removable battery 24 and internal battery 80. In one example, memory 134 stores the low and empty threshold charge levels employed in the power management state diagram of FIG. 6. Memory 134 may include separate memories for storing instructions, patient information, pump or pump motor parameters (e.g., motor speed and power range), patient and pump operation histories, and other categories of information such as any other data that may benefit from separate physical memory modules. In some examples, memory 134 stores data that, when executed by first or second processor 130, 132, cause control and power source module 12 and pump 14 to perform the functions attributed to them in this disclosure.

Components described as processors within control and power source module 12, e.g. first and processors 130, 132 or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination. Additionally, memory 62 and other computer readable storage media described in this disclosure may include a variety of types of volatile and non-volatile memory including, e.g., random access memory (RAM), static random access memory (SRAM), read only memory (ROM), programmable read only memory (PROM), erasable programmable read only memory (EPROM), electronically erasable programmable read only memory (EEPROM), flash memory, a hard disk, magnetic media, optical media, or other computer readable media.

In addition to first and second processors 130, 132 and memory 134, control and power source module 12 includes first and second telemetry modules 136, 138. Generally speaking, first and second telemetry modules 136, 138 facilitate wireless communications from and to control and power source module 12 and other devices including, e.g. a separate display device for presenting a user interface to patient 20 or another user like a clinician or an device implanted within the patient, e.g. an implanted physiological sensor. First and second processors 130, 132 may, therefore, control first and second telemetry modules 136, 138 to wirelessly communicate between control and power source module 12 and other devices including.

First and second telemetry modules 136, 138 in control and power source module 12, as well as telemetry modules in other devices described in this disclosure, can be configured to use a variety of wireless communication techniques, including, e.g. RF communication techniques to wirelessly send and receive information to and from other devices respectively. First and second telemetry modules 136, 138 may, e.g., employ RF communication according to one of the 802.11, a Medical Implant Communication Service (MICS), Bluetooth or Bluetooth Low Energy specification sets, infrared (IR) communication according to the IRDA specification set, or another standard or proprietary telemetry protocol. First and second telemetry modules 136, 138 may send information from and receive information to control and power source module 12 on a continuous basis, at periodic intervals, or upon request from a user, e.g. patient 20 via a user interface device. In one example, one of first and second telemetry modules 136, 138 communicates with a separate user interface device that includes a display, e.g. a liquid crystal display device (LCD) to display to patient 20 or another user the operation status of control and power source module 12 and pump 14, as well as the specific status of removable battery 24 and internal battery 80.

As noted above, first and second telemetry modules 136, 138 may be configured for redundant and complementary operation. For redundancy, one of first and second telemetry modules 136, 138 may act as a primary wireless communication module for control and power source module 12, while the other functions as back-up in the event the primary module malfunctions or fails. In another example, however, first and second telemetry modules 136, 138 may be configured to operate together to communicate using different wireless communication protocols or standards for communicating with different types of devices. In one example, first telemetry module 136 may be configured to communicate with peripheral devices via a Wi-Fi network using an 802.11 specification set, while second telemetry module 138 is configured to communicate with an implanted device, e.g. a physiological sensor implanted within patient 20 using MICS.

In one example of control and power source module 12, power may be delivered unregulated from removable battery 24 or internal battery 80, e.g via a switch to driver 150 and speakers 90. In contrast to the operation of a component such as speakers 90, however, power management module 140 may manage power delivered from removable battery 24 or internal battery 80 through connector 26 and cable 18 to pump 14 using power bridge 148. In one example, power management module 140 may control power bridge 148, which may include circuitry for properly and safely delivering power to drive the motor of pump 14 including, e.g., power measurement, power regulation, bridging (waveform generation), both thermal and electrical overload detection and protection, and feedback circuitry for receiving signals back from pump 14 and communicating them to, e.g. first processor 130.

Figure 11:
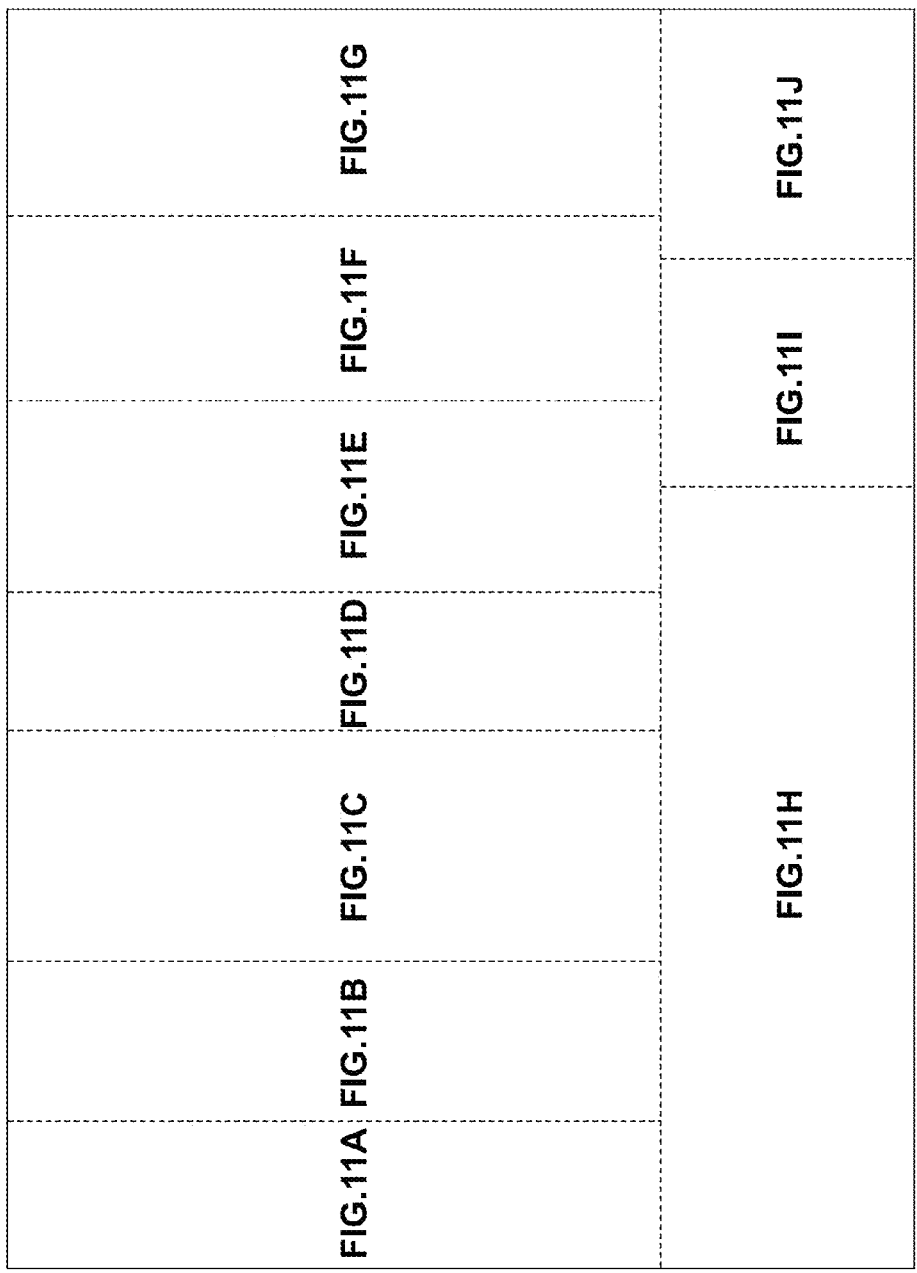
FIGS. 11A-11J ("FIG. 11") are circuit diagrams illustrating circuitry of an example of the power junction of the control and power source module of FIG. 5.
Figure 11A:
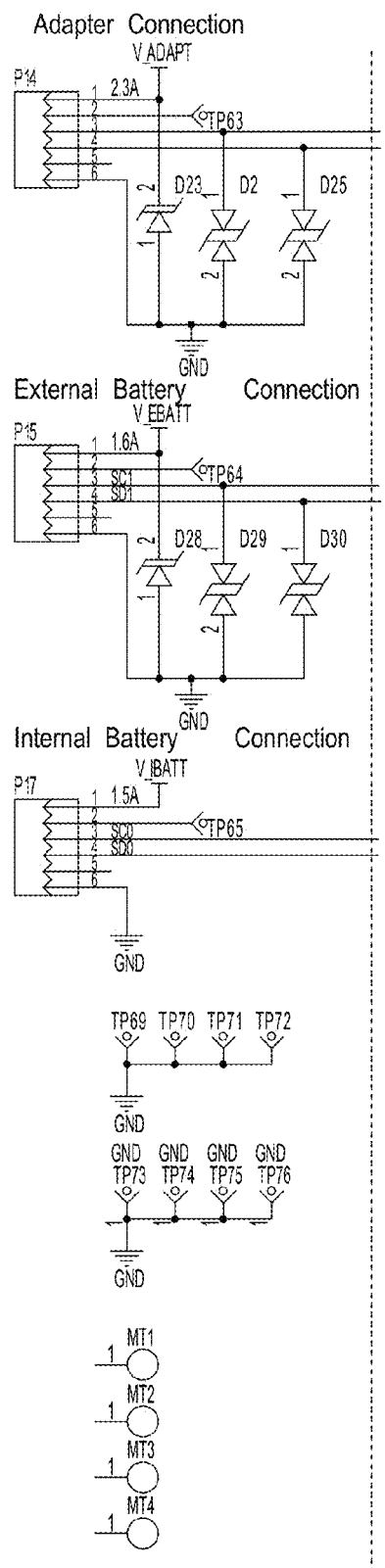
Figure 11B:
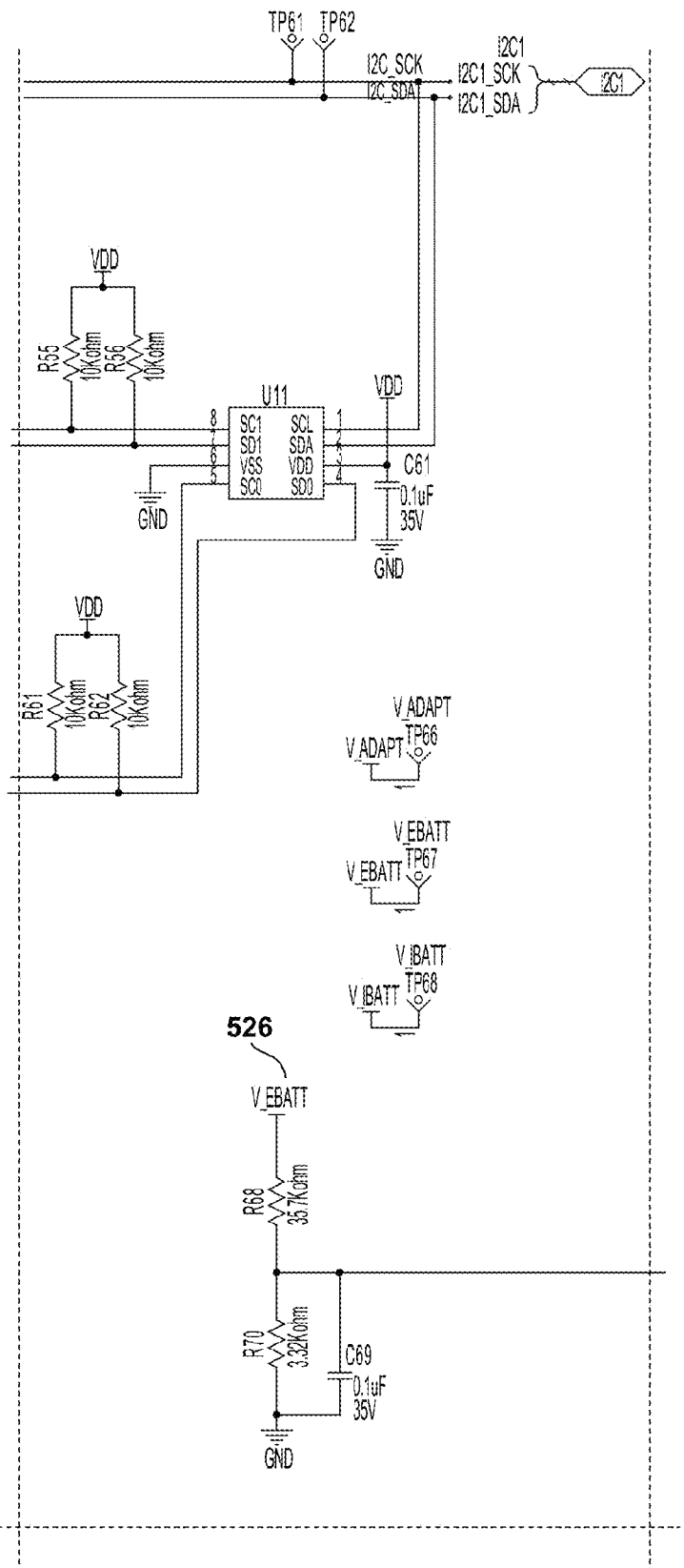
Figure 11C:
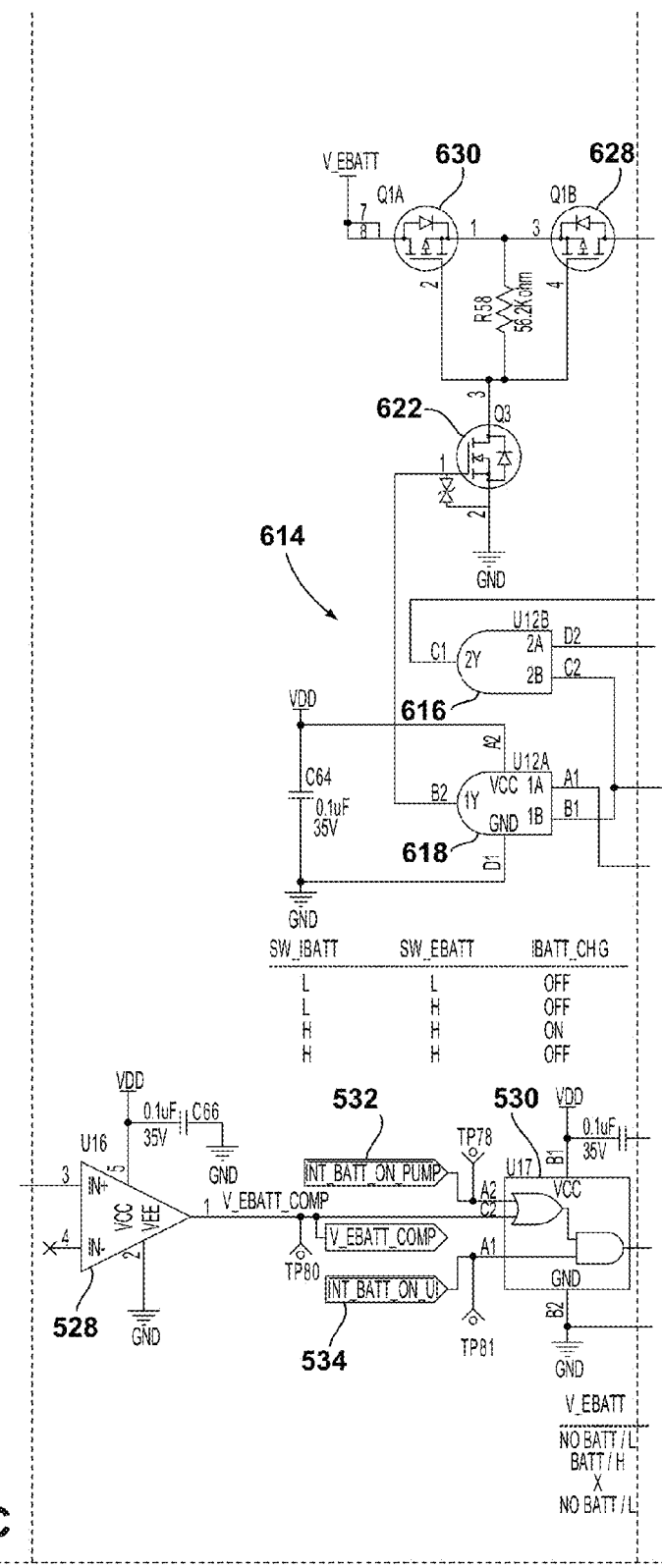
Figure 11D:
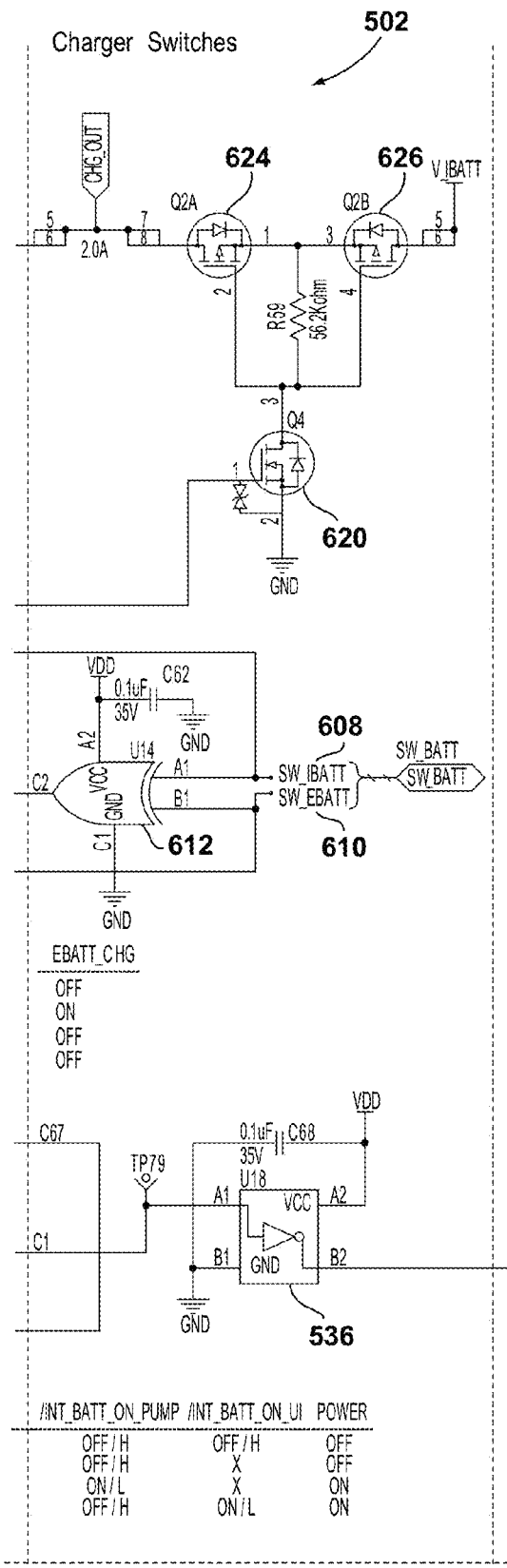
Figure 11E:
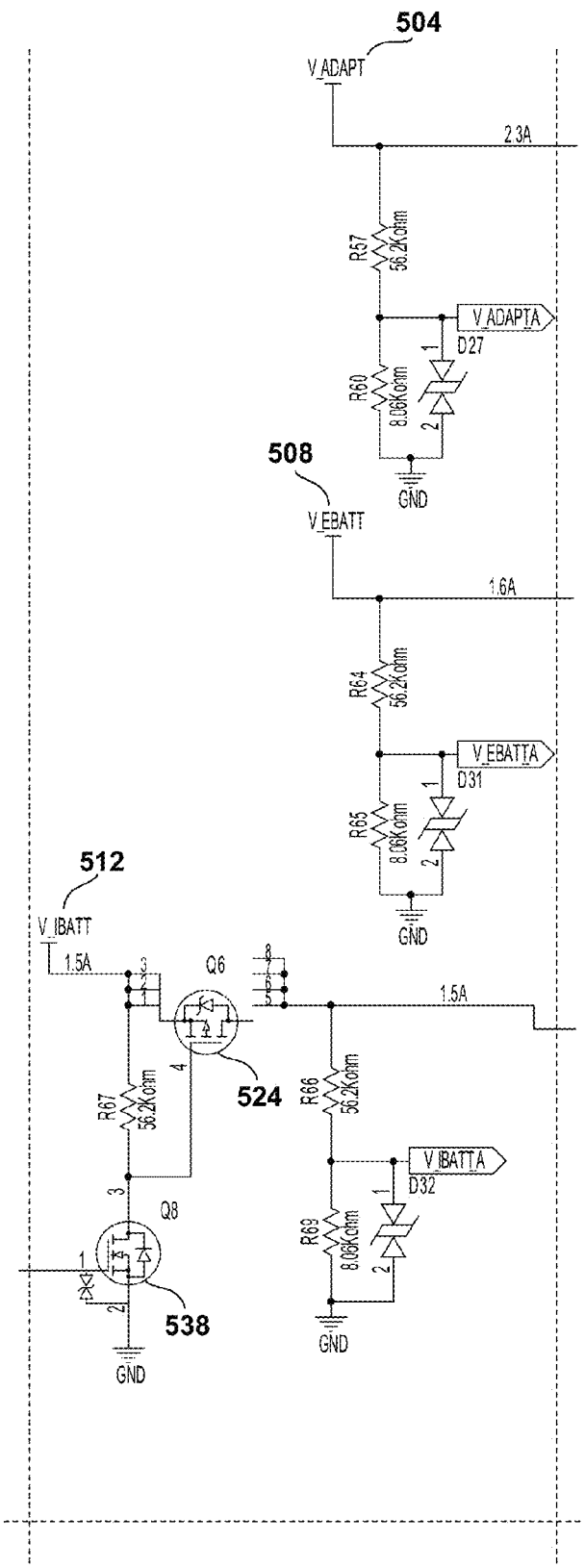
Figure 11F:
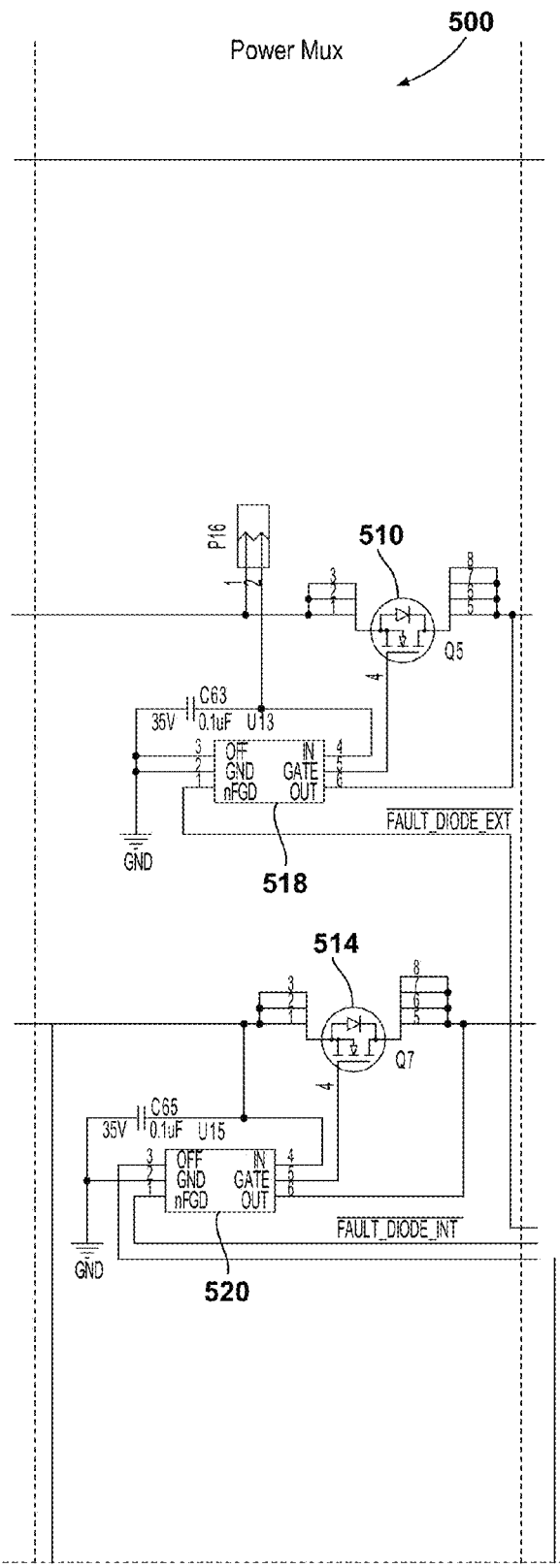
Figure 11G:
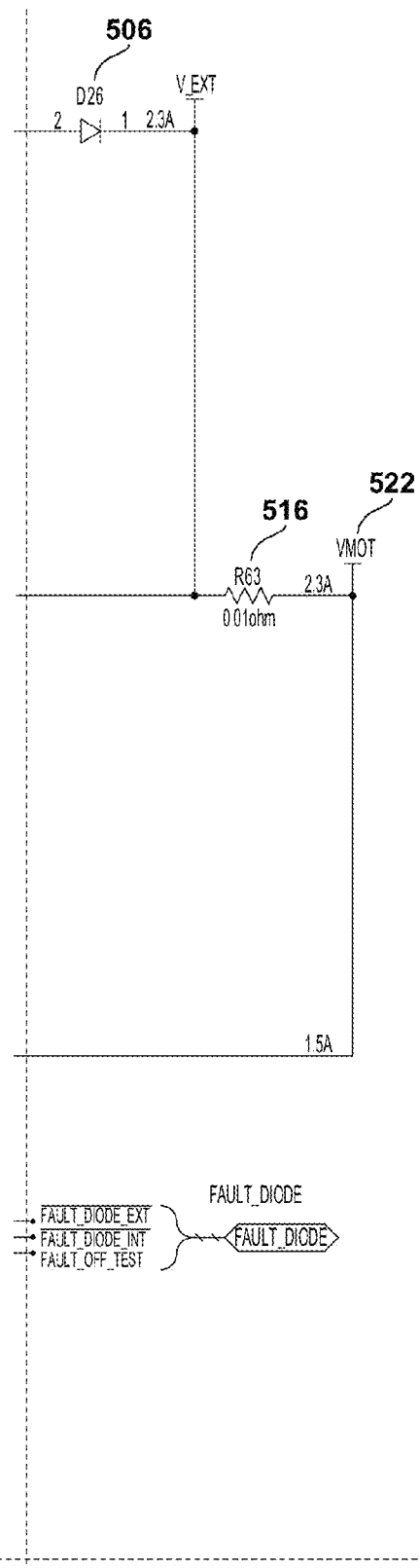
Figure 11H:
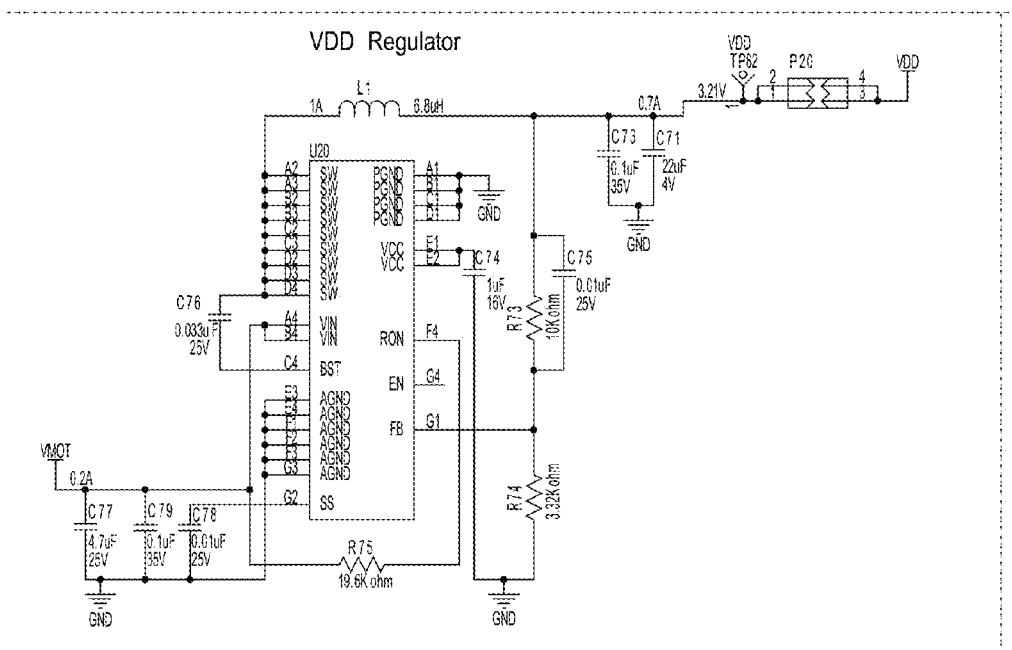
Figure 11I:
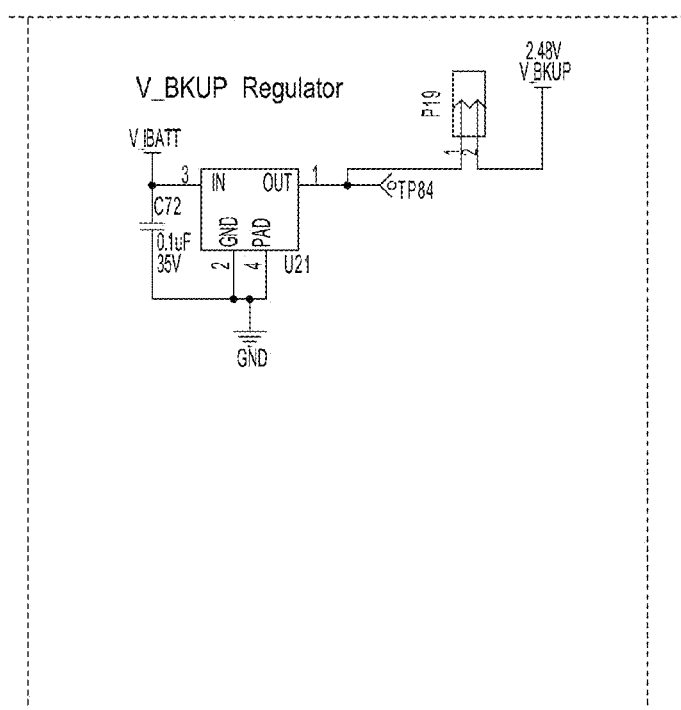
Figure 11J:
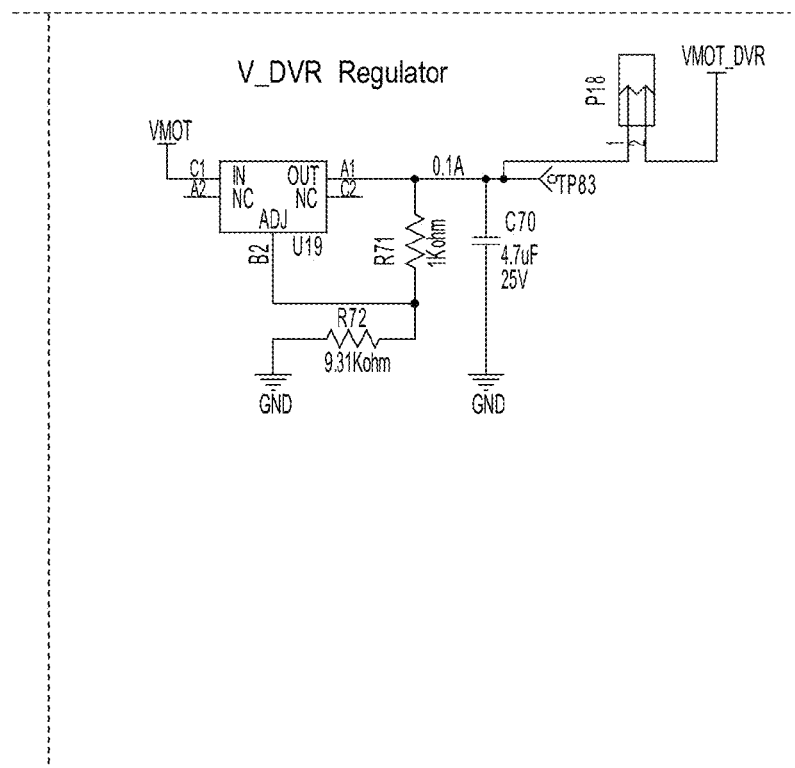

FIG. 11 is a circuit diagram illustrating the circuitry of power junction 146 (FIG. 5) in more detail. As seen in FIG.

11, power junction 146 includes power mux circuitry, shown generally at 500, and charger switches circuitry, shown generally at 502. As described in more detail below, power mux circuitry 500 allows power from several power sources, i.e., a power adapter, removable battery 24, and internal battery 80, to be combined and delivering power from only a single power source to the motor of, e.g., implanted pump 14.

In accordance with this disclosure, power mux circuitry 500 is designed to allow the highest voltage between the power sources, i.e., a power adapter, the removable battery, and the internal battery, to be selected and thus power the pump motor. As seen in FIG. 11, adapter voltage rail 504 is connected to Schottky diode 506, removable battery voltage rail 508 is connected to FET 510, and internal battery voltage rail 512 is connected to FET 514. The cathode of diode 506 and the drain of FET 510 are connected at a first terminal of charger sense resistor 516 and the drain of FET 514 is connected to a second terminal of sense resistor 516. Each of FETs 510, 514 is controlled by a FET controller, namely FET controllers 518, 520, respectively, to keep FETs 510, 514 operating at peak efficiency. One example FET controller that may be used to control FETs 518, 520 is an LM5050-2, available from National Semiconductor.

Each of FETs 518, 520 behave like ideal diodes, thereby effectively creating three "OR"-ing diodes. Whichever of the three voltages rails, i.e., adapter voltage rail 504, removable battery voltage rail 508, and internal battery voltage rail 512, is highest will appear at the common node between the three, i.e., sense resistor 516. For example, removable battery voltage rail 508 and internal battery voltage rail 512 may each have a maximum voltage of 16.8 Volts (V) and adapter voltage rail 504 may have a maximum voltage of 18V. Whenever an adapter is connected to a control and power source module, e.g., control and power source module 12, the adapter voltage will always be selected as the voltage to power the pump motor via motor bus 522 (an unregulated high voltage rail to the pump). That is, adapter voltage rail 504 will be reduced by about 0.2-0.3V by Schottky diode 506 to a voltage of about 17.7-17.8V, and the removable battery voltage rail 508 and internal battery voltage rail 512 will be reduced to a voltage of about 16.1-16.2V due to the ideal diode drop (0.6V-0.7V) of FETs 510, 514. It should be noted that the adapter voltage (either AC or DC) is designed to be higher than either the removable or internal battery voltages so that power mux circuitry 500 automatically defaults to the adapter as the power supply to motor bus 522.

Still referring to power mux circuitry 500, internal battery voltage rail 512 is also connected to FET 524. FET 524 acts as a switch and is included in power mux circuitry 500 to allow the internal battery to be connected and disconnected. In addition, if not for FET 524, the internal battery and the removable battery would drain at the same voltage level.

To the left of FET 524 in FIG. 11, logic circuitry is included to control the operation of FET 524. Generally, the removable battery voltage rail, shown at 526, is fed into comparator 528, which includes a 1.25V internal reference voltage. The output of comparator 528 is fed into 3-input OR-AND gate 530 along with two internal battery signals, 532, 534. In particular, the output of comparator 528 is fed along with internal battery signal 532 from a pump processor, e.g. first processor 130 of control and power source module 12 of FIG. 5, into the OR portion of OR-AND gate 530, and internal battery signal 534 from a UI processor, e.g. second processor 132 of control and power source module 12 of FIG. 5, is fed along with the output of the OR portion into the AND portion of OR-AND gate 530. In this manner, the operation of FET 524, and thus whether the internal battery is connected to the control and power source module, may be controlled (via inverter gate 536 and FET 538). For example, as a safety feature, if there is no removable battery voltage, then both the pump processor and the UI processor must agree and generate control signals in order for the system to shut off FET 524 (and thus disconnect the internal battery from the circuit and the control and power source module).

As another safety feature, a sudden drop in the removable battery voltage will turn FET 5240N, thereby connecting the internal battery to the control and power source module. In particular, comparator 528 compares the removable battery voltage to its internal reference and provides an output, e.g., a logical low, to the OR portion of OR-AND gate 530. The output of the OR portion is fed along with internal battery signal 534, e.g., a logical low, into the AND-portion of OR-AND gate 530, which then turns on FET 524 via inverter gate 536 and FET 538, thereby connecting the internal battery to the control and power source module.

In other examples, FET 524 may be automatically controlled based on load demands. For example, during power up, the pump motor may draw more power than during a steady state condition, e.g., due to inrush current. Using the techniques described above, power mux circuitry 500 may automatically switch over from the removable battery to the more power-dense internal battery until the pump motor reaches a steady state condition. In operation, if the removable battery cannot sustain the load, then removable battery voltage rail 526 temporarily collapses, resulting in comparator 528 firing, thereby turning on FET 524 and connecting the internal battery voltage rail 508 to motor bus 522.

In some examples, the pump processor may control FET 524 during pump start up by outputting specific control signals. It may be desirable for the pump processor to control FET 524 during start up because allowing the removable battery voltage to temporarily collapse may generate unnecessary heat. In addition to start up, physiological conditions may cause the pump motor to work harder and thus increase the load. For example, certain medications may result in thickening of the blood, and certain activities, such as lifting heavy objects, may cause vasoconstriction. In either case, the pump may need to work harder and, as a result, draw more power from the power source. Using the techniques described above, an alternate power source may be used to accommodate increased demand from the pump motor.

It should be noted that in order to save power, the UI processor may be configured to shut off if no services are being provided. The UI processor may periodically wake up, e.g., once every second, to verify that the pump processor is working properly, thereby providing a cross-checking function. In some examples, the UI processor may send a signal to the pump processor, e.g., via a serial peripheral interface (SPI) bus, and receives a predictable response. In addition, the UI processor measures the pump speed to verify that the pump processor has not failed. So, as part of the pump feedback control, not only does the pump processor measure the speed of the pump, the UI processor measures the pump speed as well in order to provide the system with a redundancy feature.

Figure 12:
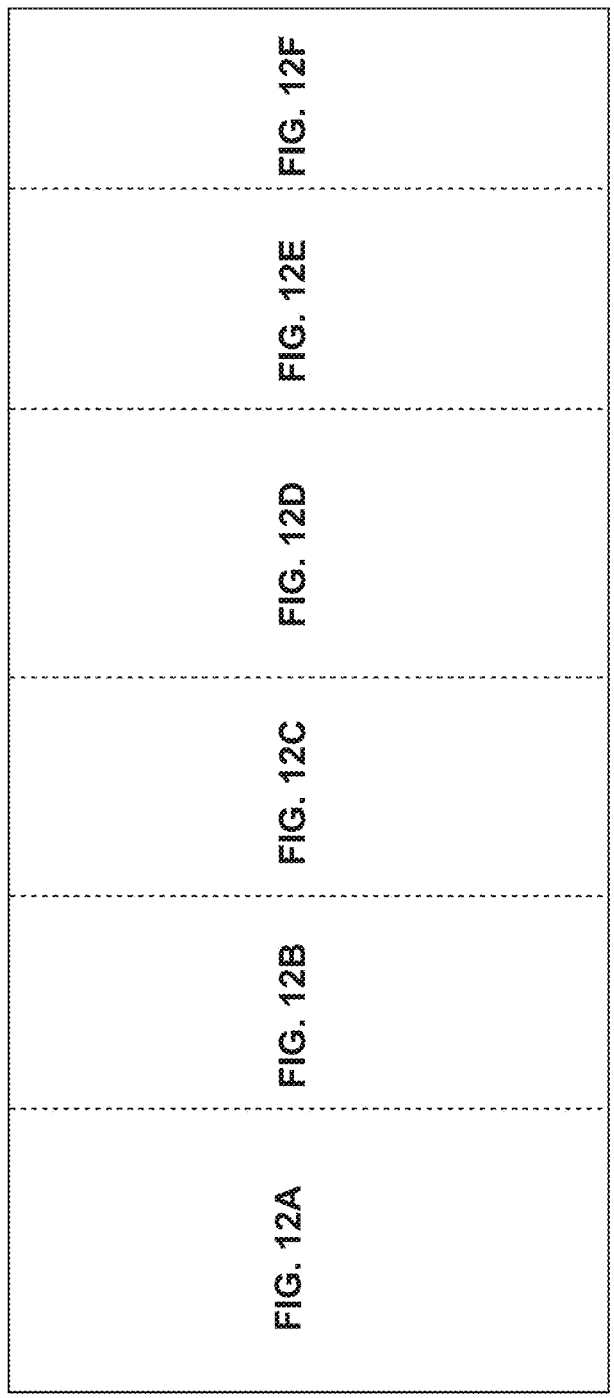
FIGS. 12A-12F ("FIG. 12") are circuit diagrams illustrating circuitry of an example of the charger of the control and power source module of FIG. 5.
Figure 12A:
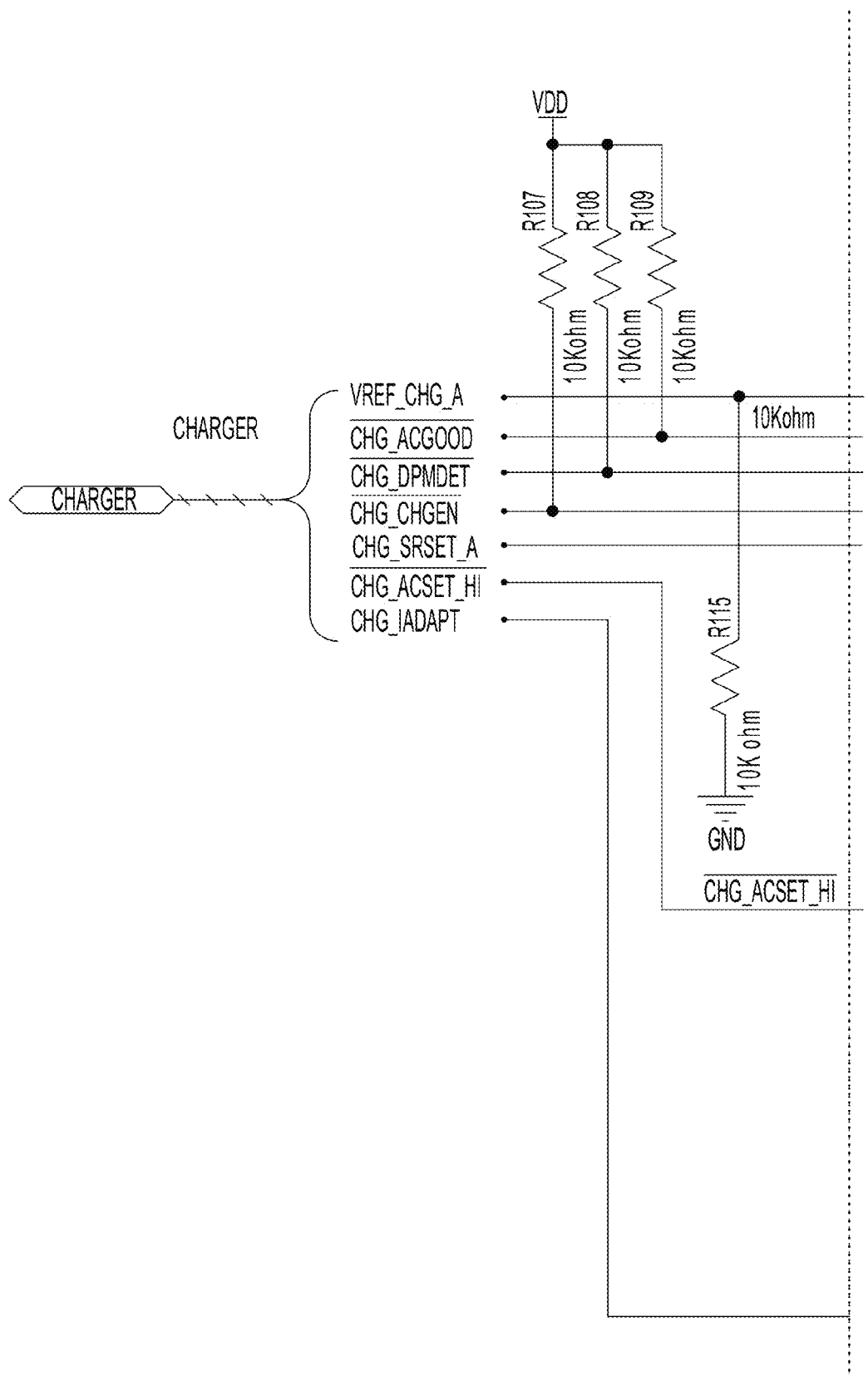
Figure 12B:
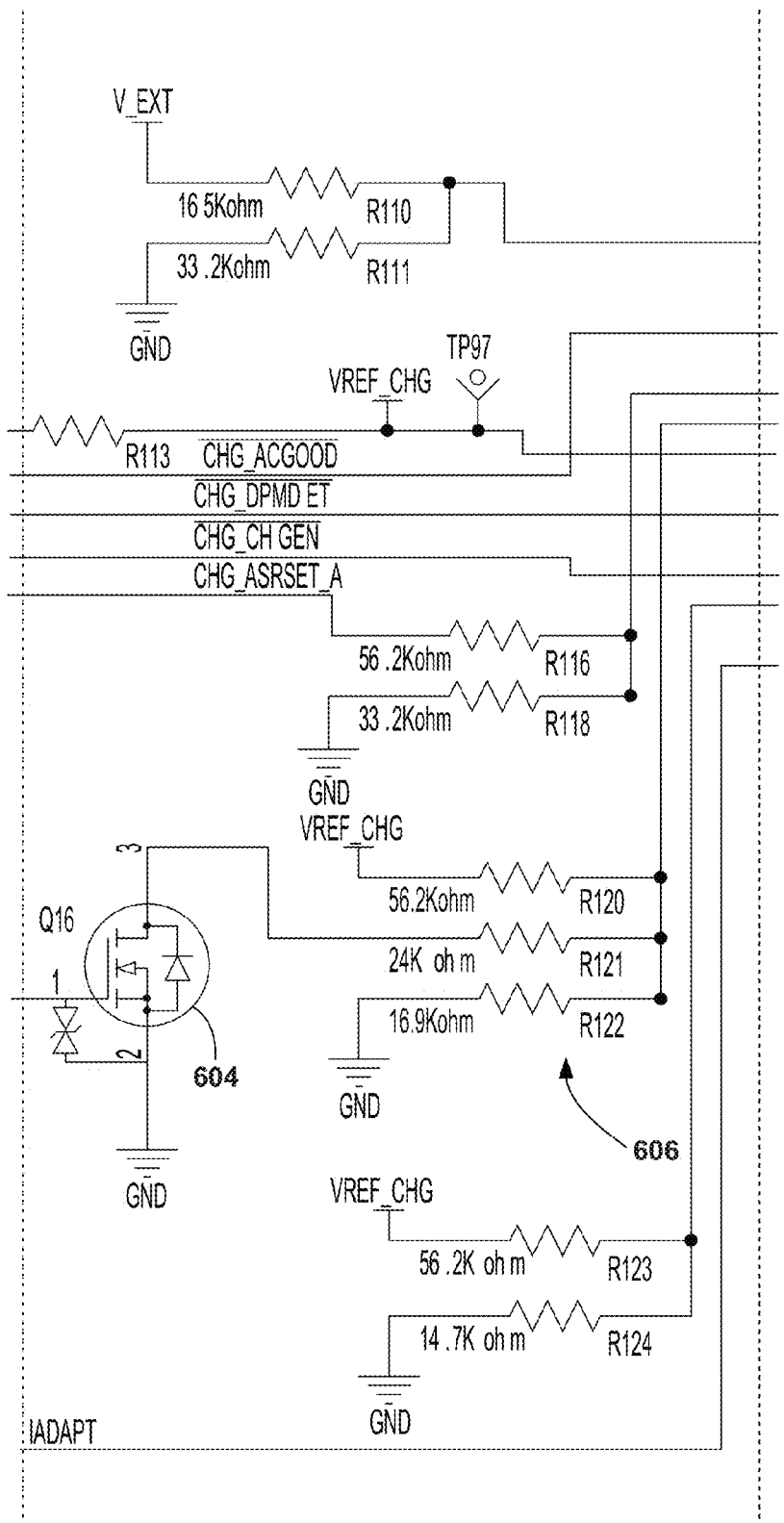
Figure 12C:
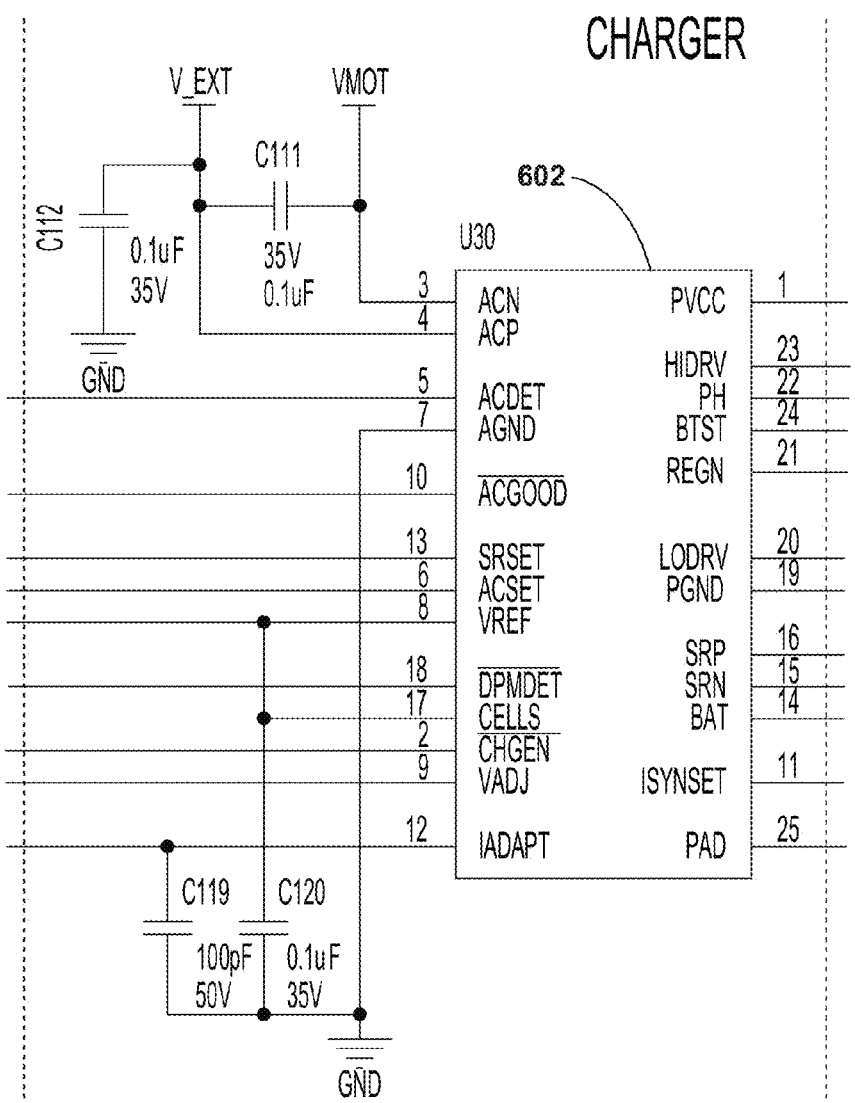
Figure 12D:
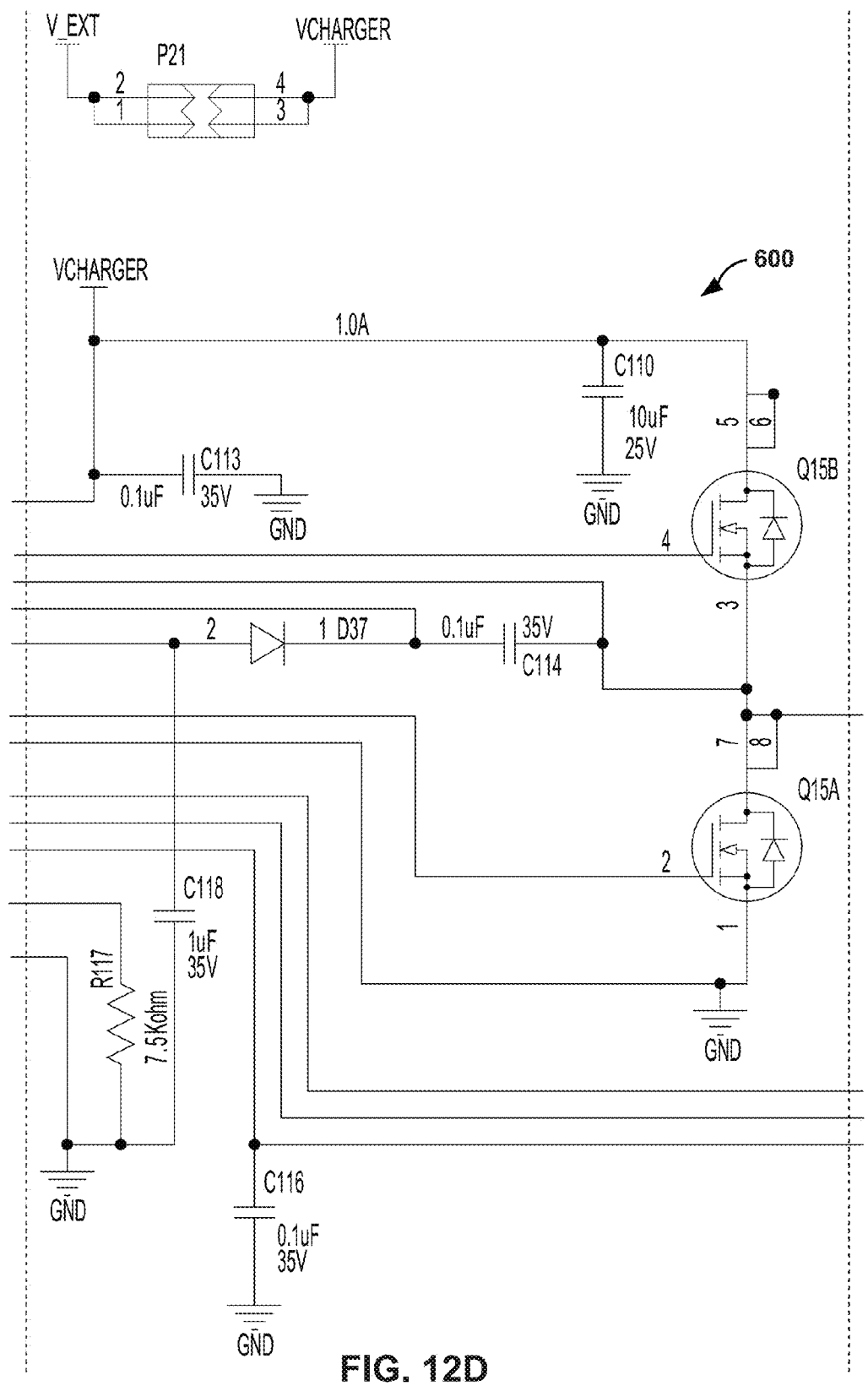
Figure 12E:
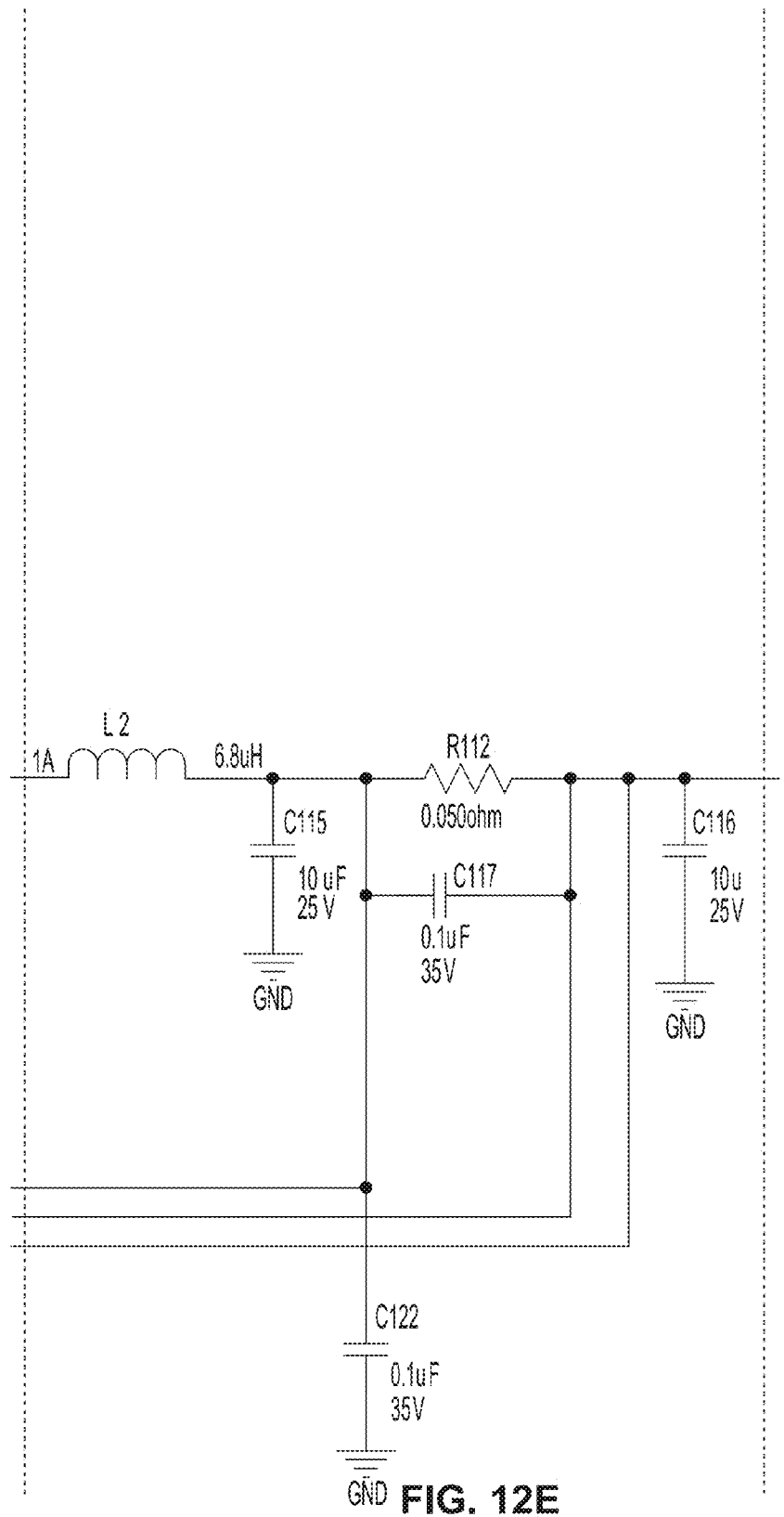
Figure 12F:
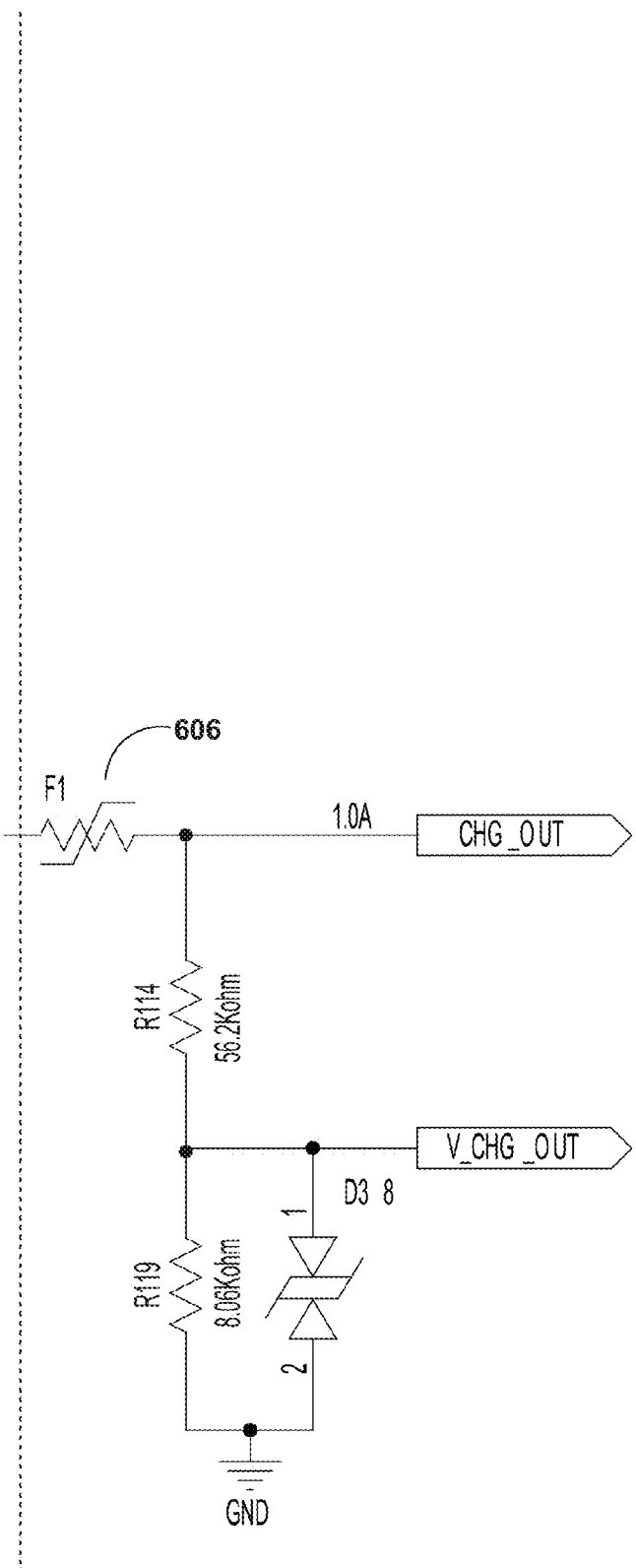

FIG. 12 is a circuit diagram illustrating the circuitry of charger 142 (FIG. 5) in more detail. In FIG. 12, charger circuitry 600, via battery charger 602, provides dynamic power management, which provides less power to the battery if the system is requiring more power so that the system is not starved of power. Using the techniques of this disclosure, charger circuitry 600 may change the power system limit based on the battery from which the system is drawing power.

As mentioned above and as seen in FIG. 11, both external power sources, i.e., the adapter and the removable battery, are connected to sense resistor 516. Battery charger 602 measures how much power is coming in to the system and battery charger 602 knows how much power it is providing to the removable battery during charging. Using dynamic power management, charger circuitry 600 may change the power system limit based on the battery from which the system is drawing power in order to provide less power to the battery during charging so that the system is not deprived of power. The power system limit is how much power the system needs and, in accordance with this disclosure, is settable. In particular, charger circuitry 600 includes FET 604 and a resistor divider network, shown generally at 606. Based on whether the system needs more power or less power, the pump processor controls FET 604 to turn ON or OFF, thereby switching in or switching out a leg of resistor divider network 606. In some example implementations, the power system limit may be controlled via a digital-analog converter (DAC) output.

In addition, in accordance with this disclosure, sense resistor 516 (FIG. 11) is connected to the external power sources, namely the adapter and the removable battery, and not the internal battery. Sense resistor 516 need not be connected to the internal battery because, by design, the system does not charge from the internal battery.

Further, charger circuitry 600 includes resettable fuse 606 for safety. It should be noted that resettable fuse 606 may be included on the charger board in some example implementations.

Referring again to FIG. 11, charger switches circuitry 502 provides a fail-safe means to control whether the internal battery or the removable battery receives power from the charger, thereby allowing the system to use a single charger circuit. Charger switches circuitry 502 includes a combination of FETs and logic circuitry that allows the pump processor to select which battery is charging. The logic circuitry eliminates the possibility of a short between the internal and removable batteries.

In charger switches circuitry 502, the pump processor provides two control signals, namely internal battery switch signal 608 and removable battery switch signal 610, to exclusive-OR gate 612. The output of exclusive-OR gate 612 is fed into one input of each of the AND gates of a dual 2-input positive AND gate, shown generally at 614. The other two inputs of the AND gates of dual 2-input AND gate 614 are supplied by internal battery switch signal 608 and removable battery switch signal 610. In particular, internal battery switch signal 608 is supplied to an input of AND gate 616 and removable battery switch signal 610 is supplied to an input of AND gate 618. The output of AND gate 616 turns on FET 620, which causes the internal battery to begin charging through FETs 624 and 626. The output of AND gate 618 turns on FET 622, which causes the removable battery to begin charging through FETs 628 and 630.

In one example implementation, the removable battery begins charging if internal battery switch signal 608 is a logic level low and removable battery switch signal 610 is a logic level high, and the internal battery begins charging if internal battery switch signal 608 is a logic level high and removable battery switch signal 610 is a logic level low. If internal battery switch signal 608 and removable battery switch signal 610 are at the same logic level (low or high), then neither battery is charging.

Figure 13:
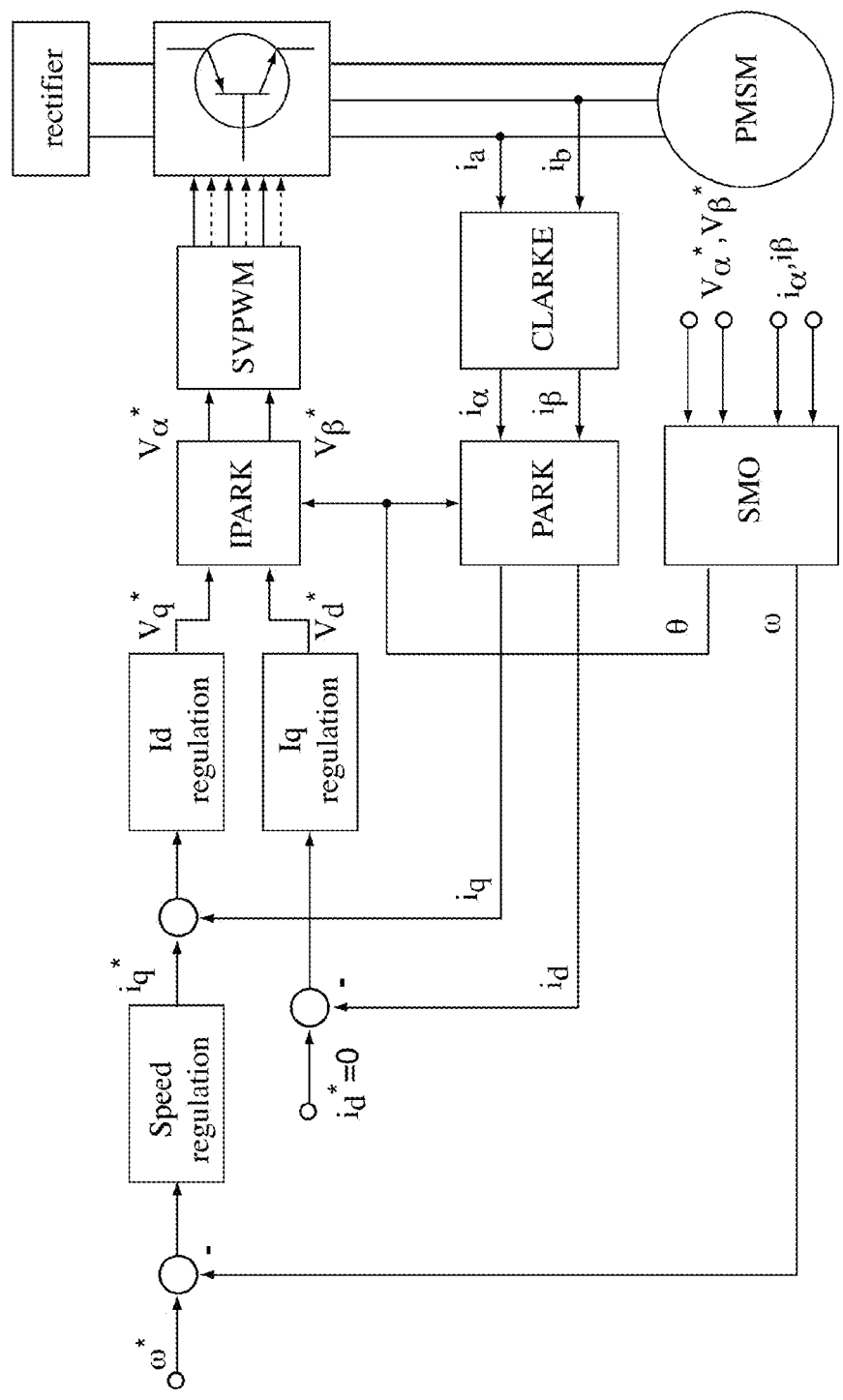

As mentioned above with reference to FIG. 5, one example of control and power source module 12 may employ one of first or second processors 130, 132 to control an electric motor driving pump 14 according to a field-oriented controller (FOC) algorithm stored as executable instructions within memory 134. FOC may generally act to achieve improved motor control by trading the burden of complex and processor intensive mathematics for the ability to directly affect the basic motor parameters of concern. The FOC algorithm may be implemented in several steps. First, the three phase currents, which are represented on a stationary, time-dependent, three-axis coordinate system (a, b, c), are mapped into a single current vector on a stationary, time dependent, two-axis coordinate system ($\alpha$, $\beta$) using a Clarke Transformation. Second, this stationary frame is mapped to a rotating, time-independent, two-axis coordinate system (d,q) using a Park Transformation. This means that $I_d$ and $I_q$ (and subsequently $T_M$ and $\omega_M$) are a function of phase currents ($I_a$, $I_b$, $I_c$) and flux or rotor electrical position ($\Theta_E$). A system diagram representing these aspects of the FOC algorithm is illustrated in FIG. 13.

The need for the flux position, $\Theta_E$, is unique to FOC. In order to maintain a sensorless configuration, the flux position, $\Theta_E$, may be derived indirectly from the phase currents, voltages and back-EMFs. This may be accomplished by employing a Sliding Mode Observer, which compares the measureable parameters of the motor driving pump 14 to a model. Once the error of the model is minimized, the flux position, $\Theta_E$, is calculated from the model, e.g. in accordance with the formulas presented in FIGS. 14A-F.

Figure 15A:
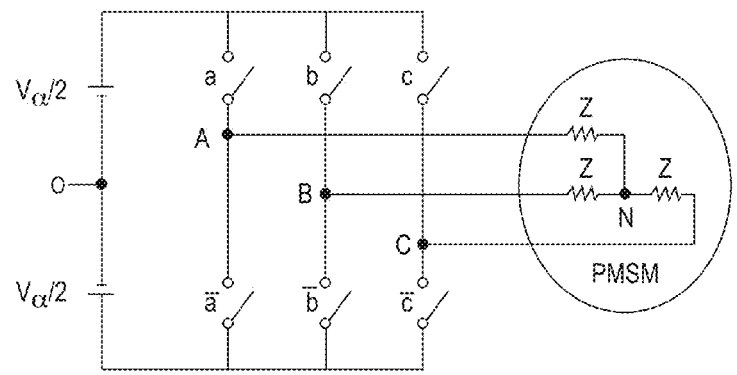
Figure 15B:
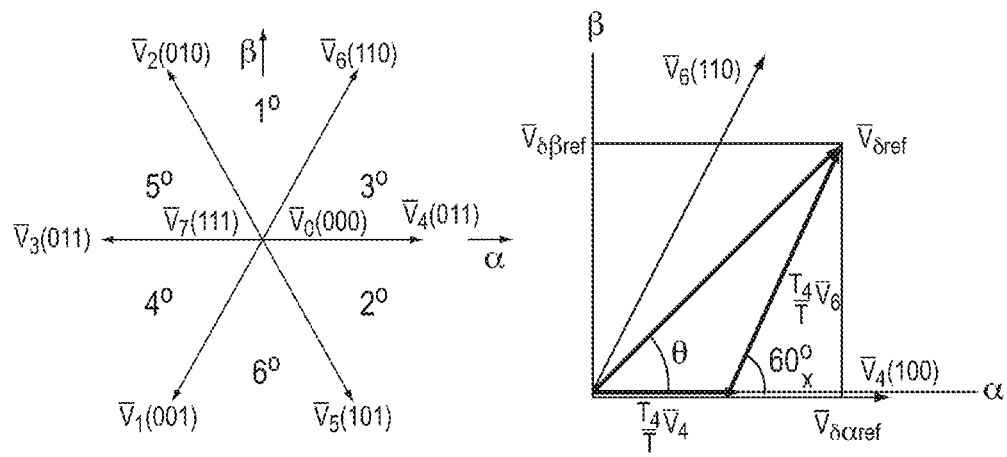
Figure 16A:
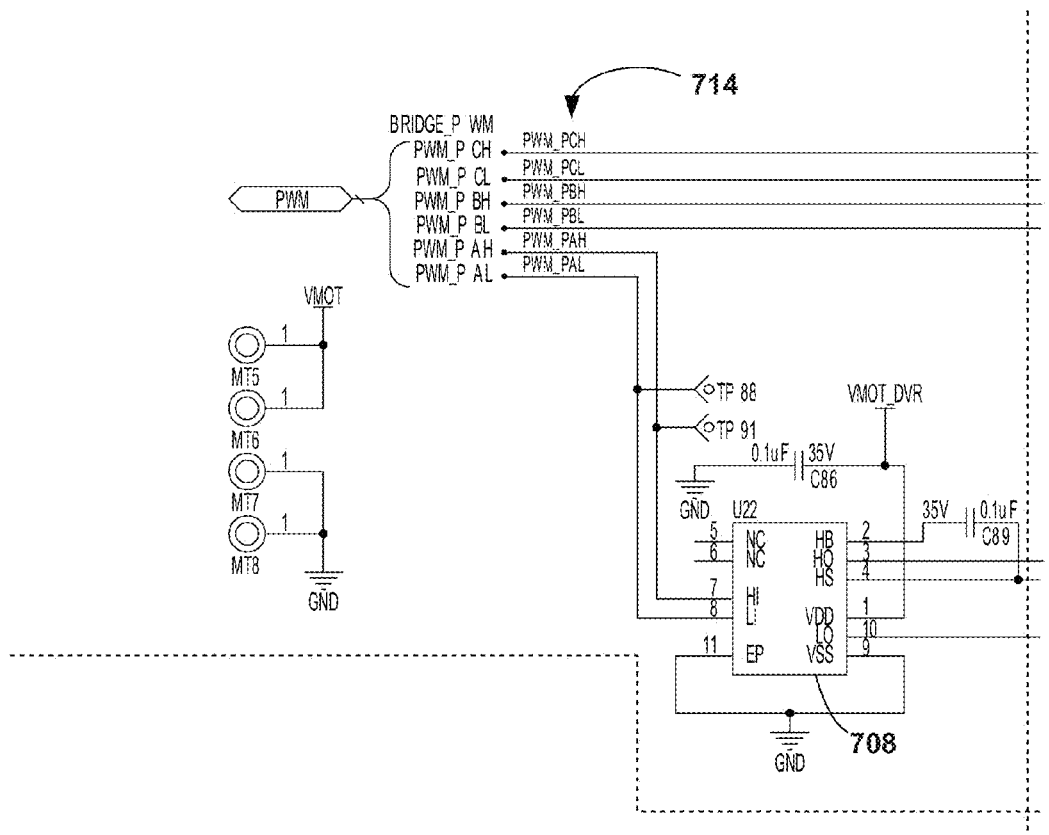
FIGS. 16A-16M ("FIG. 16") are circuit diagrams illustrating circuitry of an example of the power bridge of the control and power source module of FIG. 5.
Figure 16B:
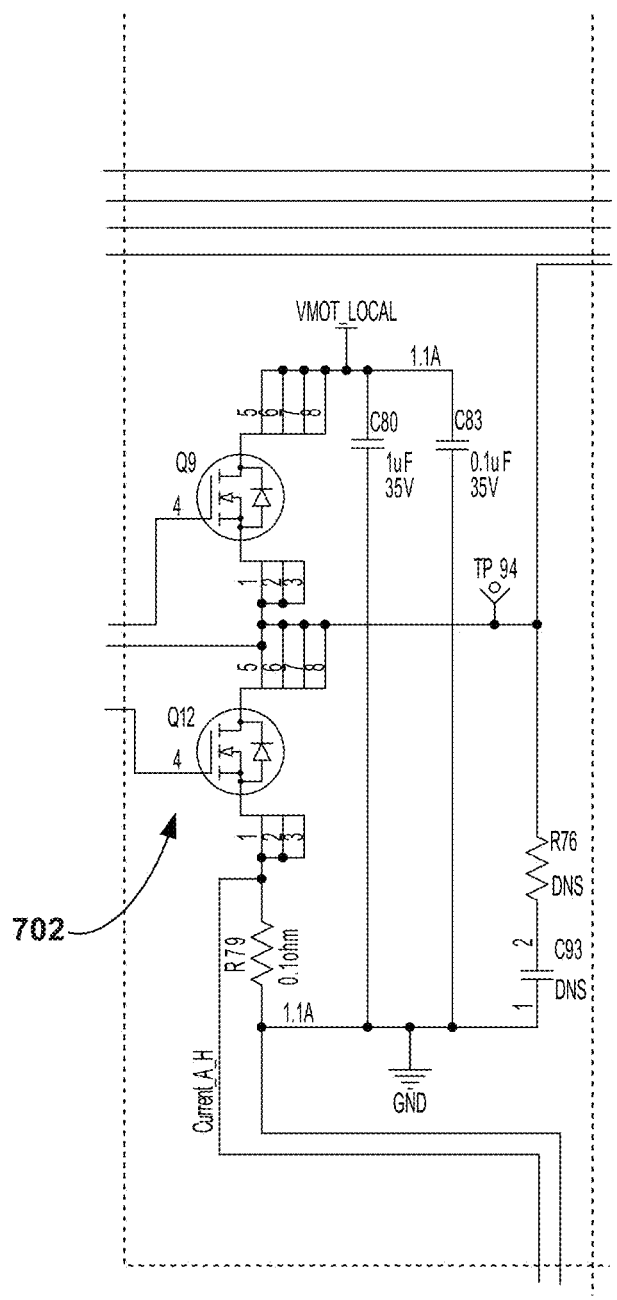
Figure 16C:
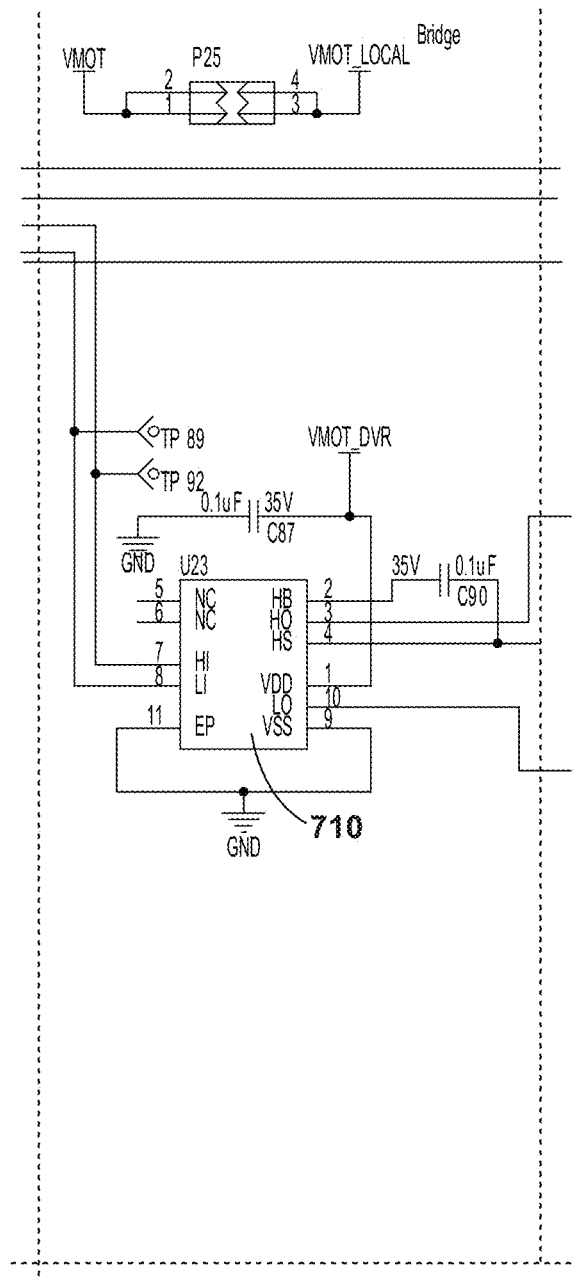
Figure 16D:
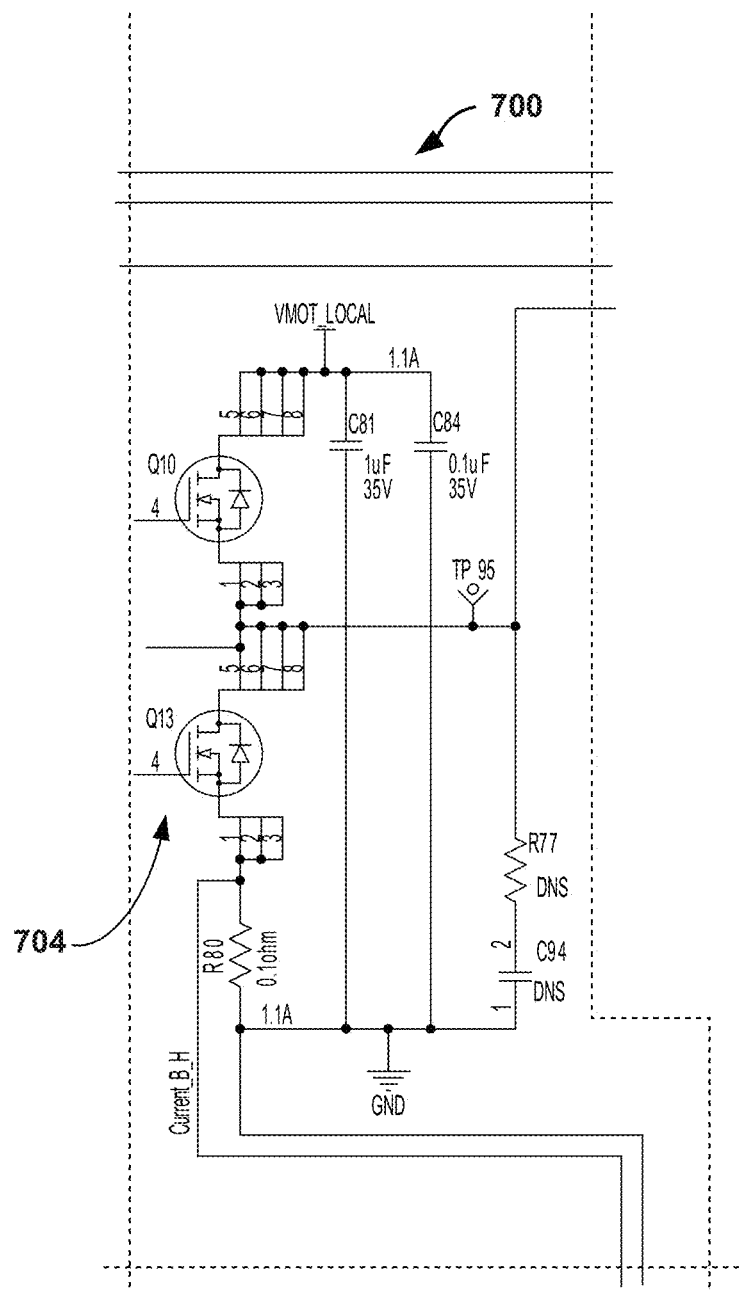
Figure 16E:
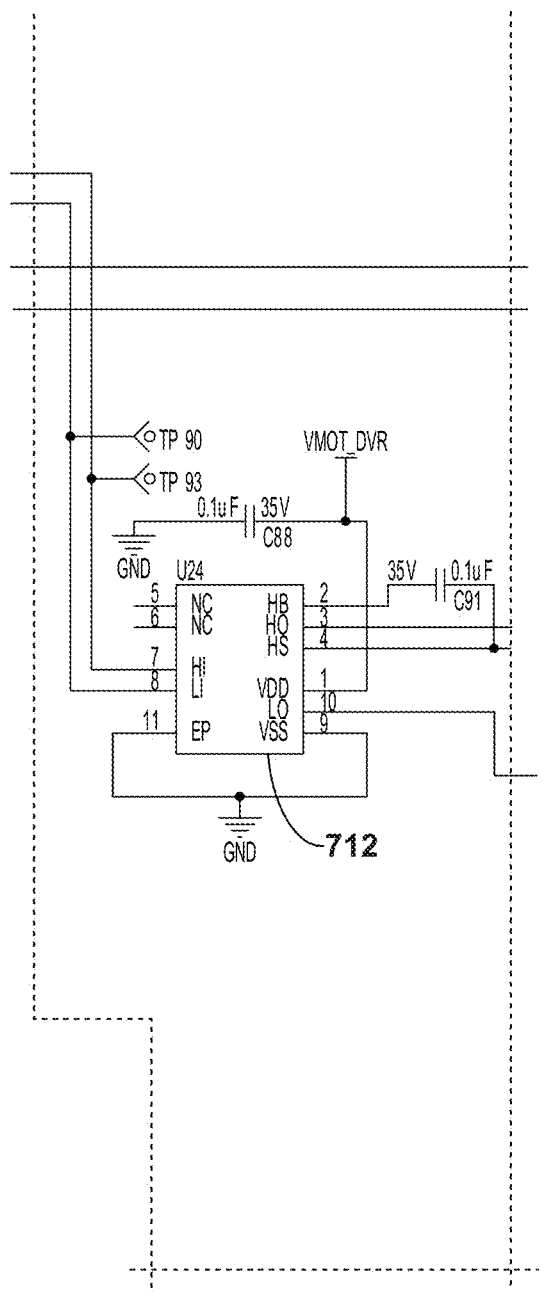
Figure 16F:
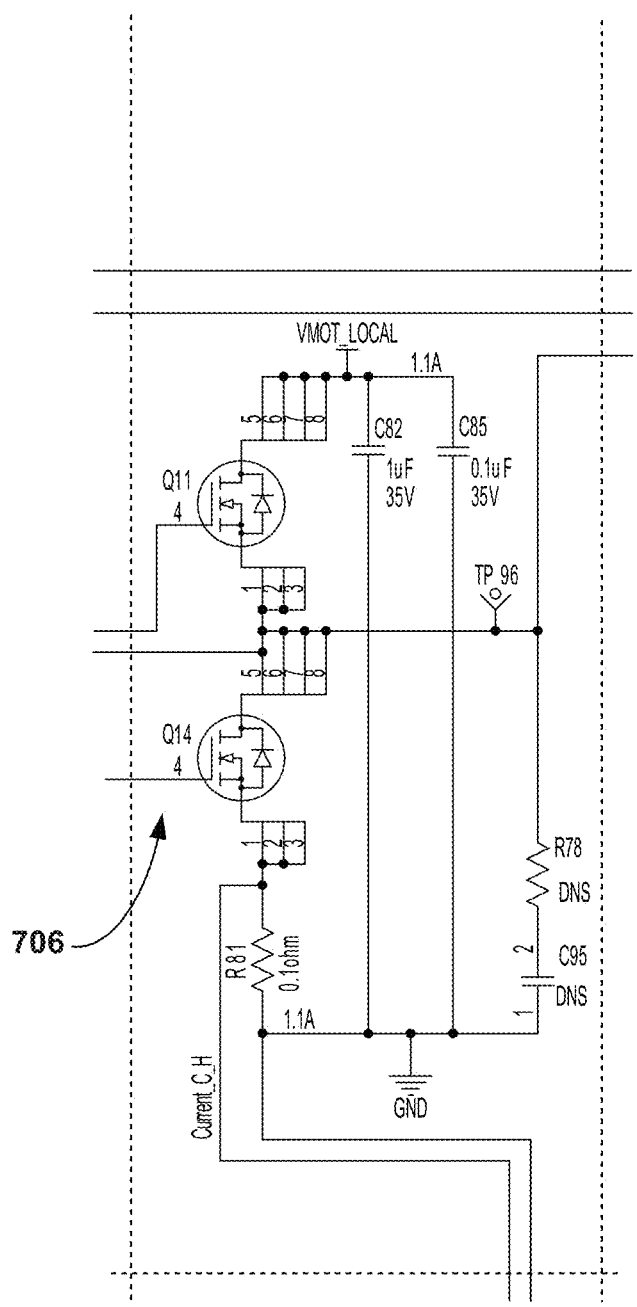
Figure 16G:
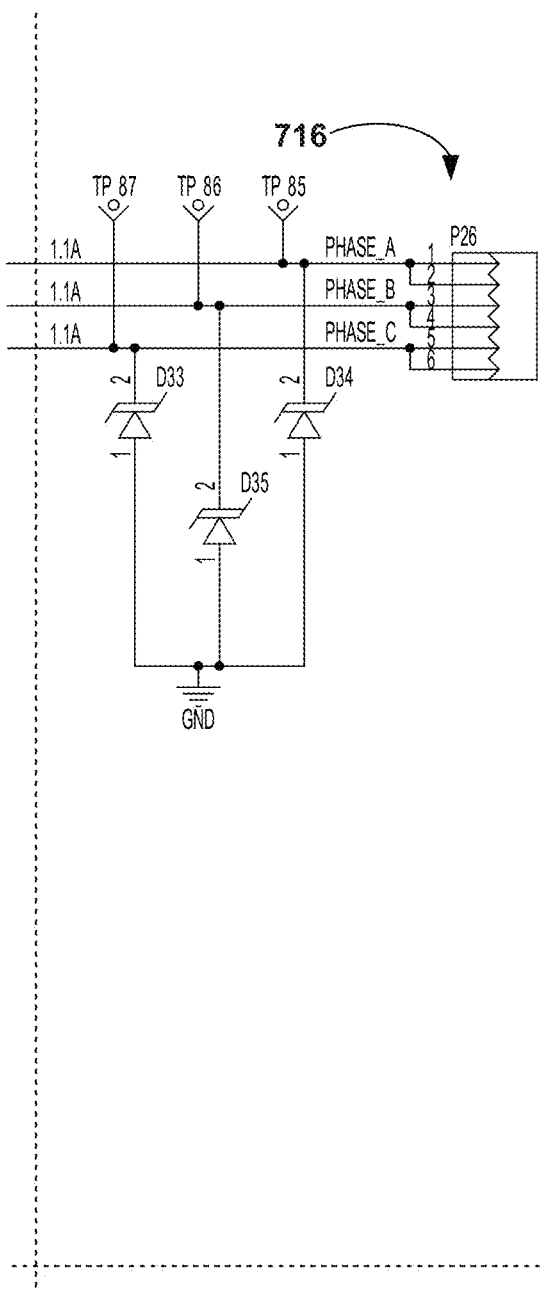
Figure 16H:
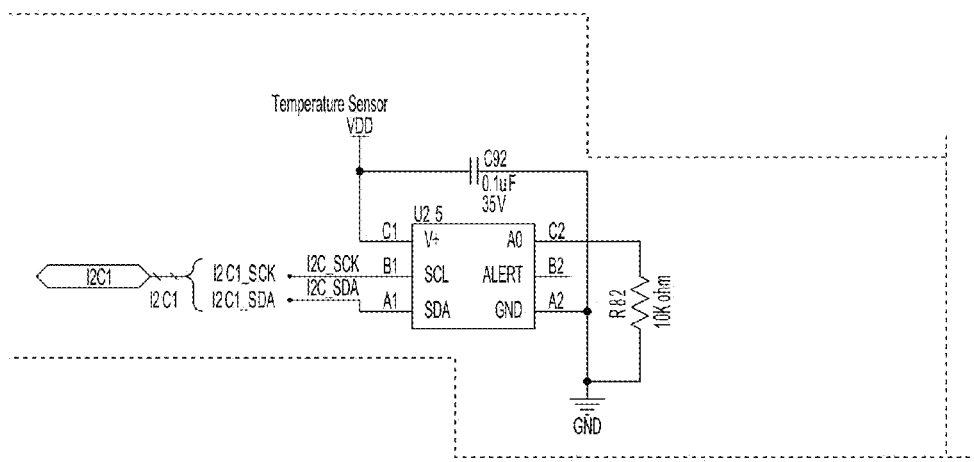
Figure 16I:
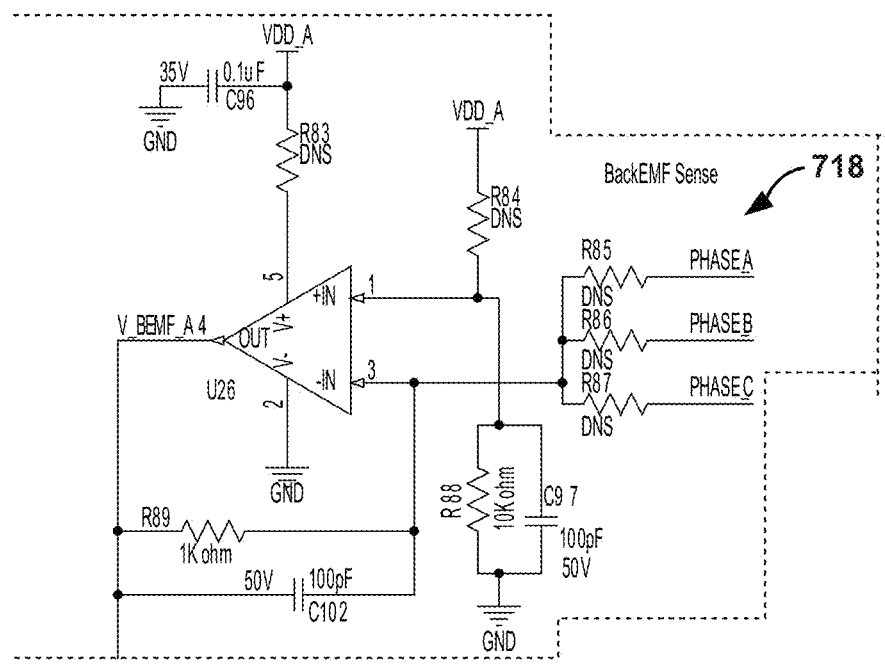
Figure 16J:
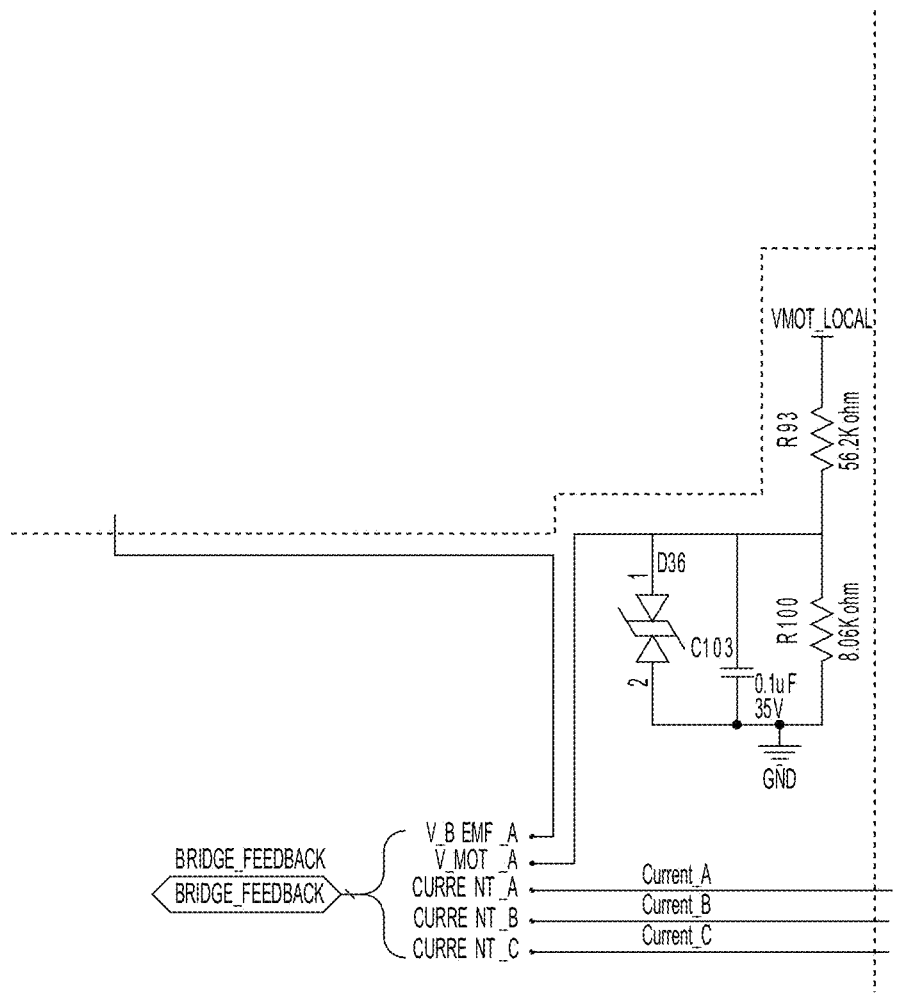
Figure 16K:
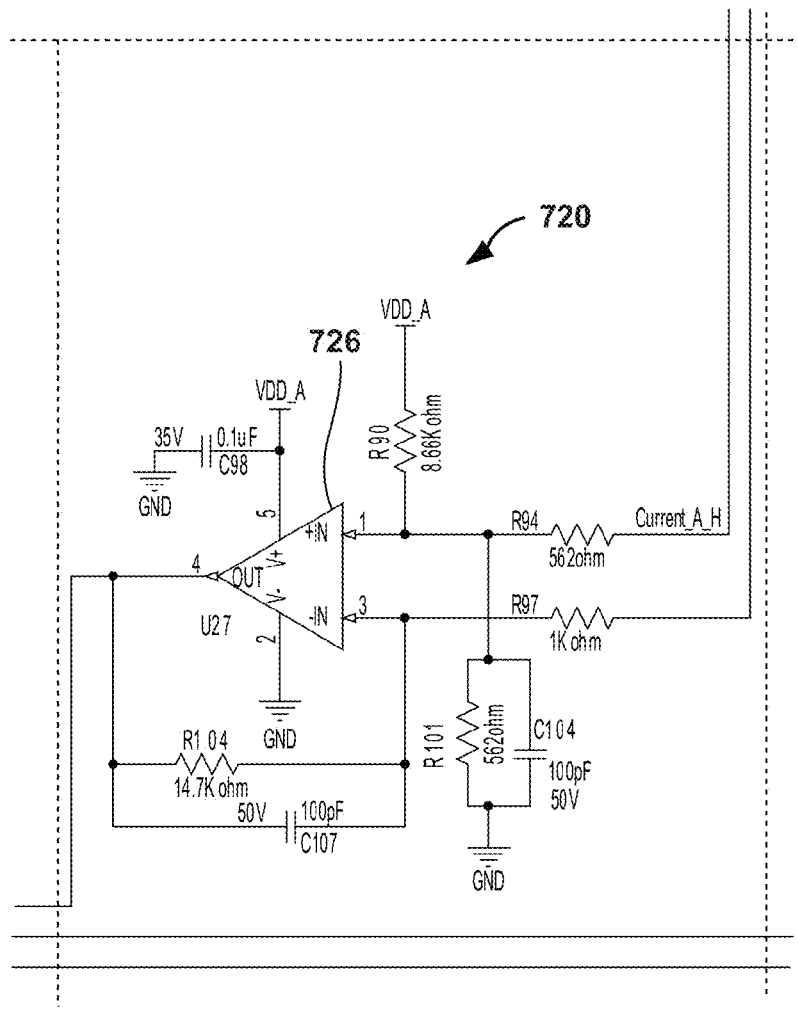
Figure 16L:
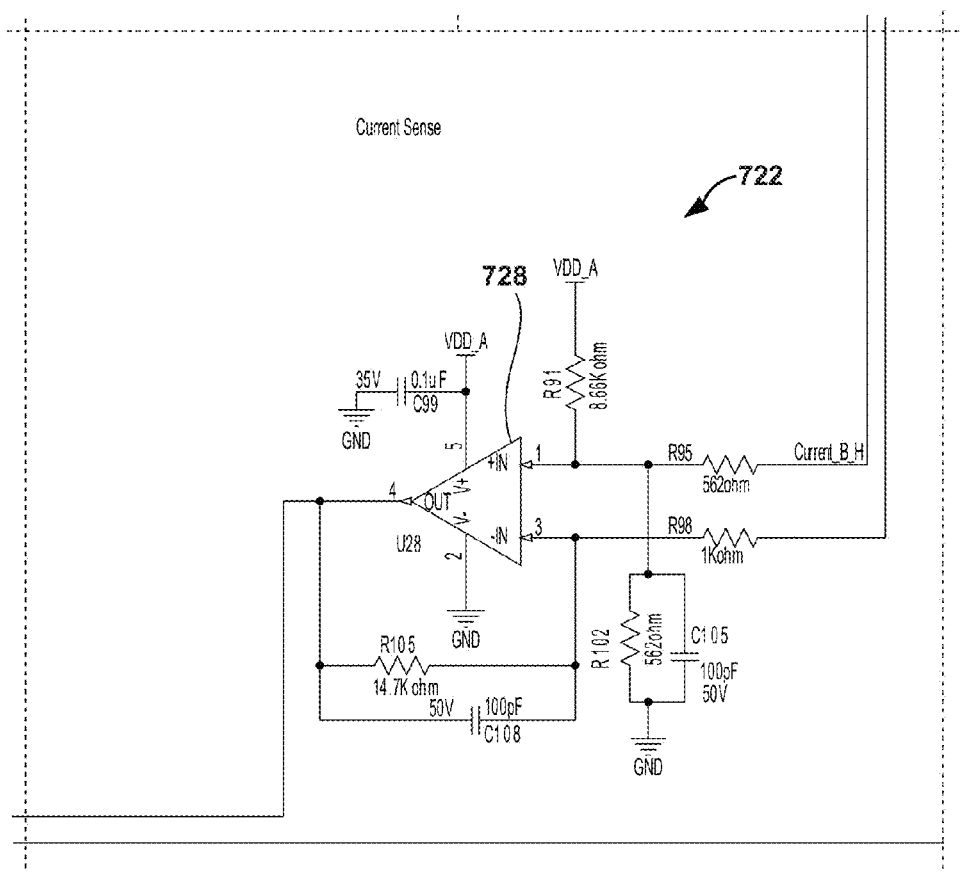
Figure 16M:
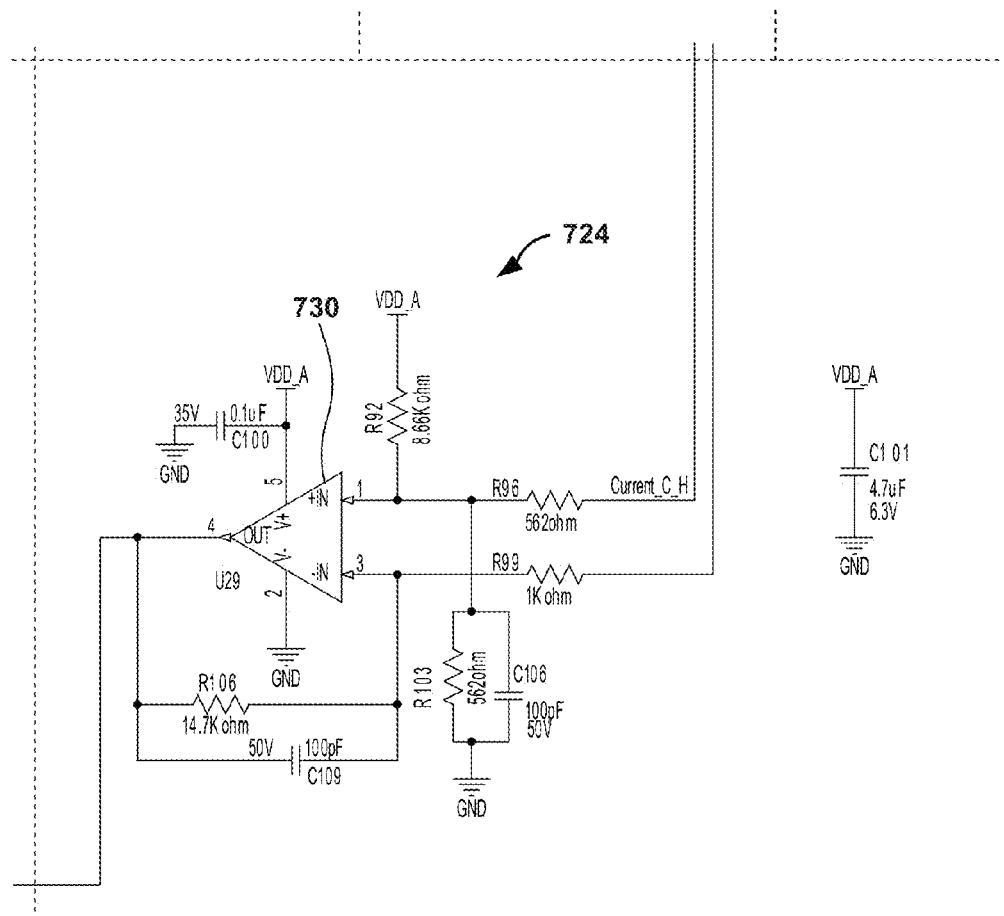

In order to avoid large inefficient analog elements for the amplifier of the motor driving pump 14, three half bridges may be employed in the control and power source module controller to deliver power to the motor. The switch pairs of three half bridges only have 8 states, which are shown in FIG. 15A. The eight phase voltages are represented in a $\alpha$-$\beta$ coordinate system in FIG. 15B. The bridges are pulse-width modulated in accordance with the vectors between these values, as illustrated in FIG. 15B, to create sine wave voltages on the three phases of the motor driving pump 14 necessary to properly drive the motor.

An FOC algorithm employed to control the motor of a pump of a VAD may be implemented in conjunction with various hardware configurations of a VAD control and power source module. For example, motor currents may be measured via a three-shunt design in which each shunt measures current in each of the three motor phases. In another example, however, the currents of each of the phases of the pump motor may be measured via a single shunt. In this configuration, all three motor phases are fed into the single shunt, which is measured at specific times to distinguish and measure one motor phase current from the other two. Example FOC algorithms may be optimized for a particular set of pump motors or may be made generic to control a wide range of motors. The FOC algorithm, or another employed in conjunction with FOC, may be configured to measure pump parameters, other than motor currents and adapt the FOC algorithm based on such measurements. Additionally, in one example, an FOC algorithm may be configured to retrieve identifying information from the control and power source module pump to be stored and used in the execution of the algorithm. For example, the percutaneous cable connecting the implanted VAD pump to the external control and power source module may include a memory chip embedded in the cable. When the control and power source module is connected to the pump, the device could retrieve pump information from the memory chip. Finally, the control and power source module employing FOC may be configured to analyze data employed in the FOC algorithm for other purposes. For example, the load placed on the pump, e.g. as a function of pump motor torque and speed, may be estimated by the control and power source module based on the motor currents measured for and employed in the FOC algorithm. Example circuitry and additional logic for FOC, as well as alternative motor control methods are described below with reference to FIGS. 16-18.

FIG. 16 is a circuit diagram illustrating the circuitry of power bridge 148 (FIG. 5) in more detail. In FIG. 16, bridge circuitry 700 includes three pairs of high and low FETs, shown generally at 702, 704, and 706. A high voltage high-side and low-side gate driver is connected to a gate of each FET of a respective FET pair. In particular, gate driver 708 is connected to each gate of FET pair 702, gate driver 710 is connected to each gate of FET pair 704, and gate driver 712 is connected to each gate of FET pair 706.

The pump processor, e.g. first processor 130 of control and power source module 12 of FIG. 5, provides high and low control signals, shown generally at 714, for one of phases A, B, and C to a respective gate driver 708, 710, and 712 in order to pulse width modulate (PWM) a respective FET pair. In one example implementation, the pump processor provides high and low PWM control signals for phase A to gate driver 708, high and low PWM control signals for phase B to gate driver 710, and high and low PWM control signals for phase C to gate driver 712.

The three pairs of FETs 702, 704, 708 can be controlled such that there are $2^3$=8 combinations of FETs. For example, each upper FET of a FET pair 702, 704, 708 can be opened and each lower FET of a FET pair 702, 704, 708 can be closed for a first combination, each upper FET of a FET pair 702, 704, 708 can be closed and each lower FET of a FET pair 702, 704, 708 can be opened for a second combination, and the like, to provide three phase power to the motor, shown generally at 716. The two combinations (of the eight possible combinations) in which all FETs of FET pairs 702, 704, 708 are either opened or closed result in "dead time" because these two combinations do not cause a change in the rotor.

Using the techniques of this disclosure, the pump processor may provide both trapezoidal control and FOC control. In trapezoidal control, the remaining six combinations of FETs can be controlled by the pump processor such that, using a particular combination, a current vector can be created in the motor at a certain position and magnitude, which then causes the rotor to attempt to align with the vector. Then, the pump processor can select another combination of FETs, which creates another current vector in the motor at a certain position and magnitude, which then causes the rotor to attempt to align with the vector. By knowing the position of the rotor, the pump processor may continue to select amongst the six combinations of FETs that will attract the rotor, thereby causing the motor to rotate from one position to the next. Thus, the pump processor may control the rotation of the motor using six different current vectors, each having the same magnitude (but the orientation may be changed), using trapezoidal control techniques.

FOC control is similar to the trapezoidal control techniques described above. However, in FOC control, the two combinations that resulted in "dead time" are used. In particular, the two combinations in which all of the FETs of FET pairs 702, 704, 708 are either opened or closed may be used to shorten a length of a current vector, i.e., reduce the amount of current, which produces less torque, thereby slowing the motor. For example, the pump processor may select one of the six combinations of FETs that will attract the rotor (i.e., a combination other than the two combinations that cause "dead time"). For a given period of time, the pump processor may PWM for a part of the time using the selected vector and part of the time using one of the two combinations of FETs in which all of the FETs are either opened or closed. This FOC technique effectively shortens the length of the selected vector. In addition, this FOC technique allows the pump processor to use combinations of vectors, which in turn creates intermediate positions between vectors. These intermediate positions may allow the pump processor to control the pump motor such that the motor runs more smoothly than what may be achieved using trapezoidal control, which only allows six positions.

Bridge circuitry 700 further includes back electromotive force (EMF) sense circuitry, shown generally at 718, and current sense circuitry, shown generally at 720, 722, and 724. With trapezoidal control, in order to provide motor feedback to the pump processor, zero voltage crossings are measured using voltage sensing provided by back EMF circuitry 718. At any given time, two coils are energized and back EMF circuitry 718 senses when the third coil changes polarity (negative to positive or positive to negative). This change in polarity in the third coil provides the indication to the pump processor that it is time to commutate.

With FOC, all the coils are energized at any given time, so traditional voltage sensing on the back EMF does not provide sufficient accuracy for commutation. Instead, current sense circuitry 720, 722, 724 provides current measurements for phase A, B, C, respectively, to the pump processor via a respective operational amplifier 726, 728, 730. Upon receiving current measurements for each of phases A, B, C, the pump processor performs various calculations in order to infer the back EMF. Thus, the circuitry of FIG. 16, namely back EMF circuitry 718 and current sense circuitry 720-724, allows for feedback whether the system is using trapezoidal control or FOC.

Figure 17:
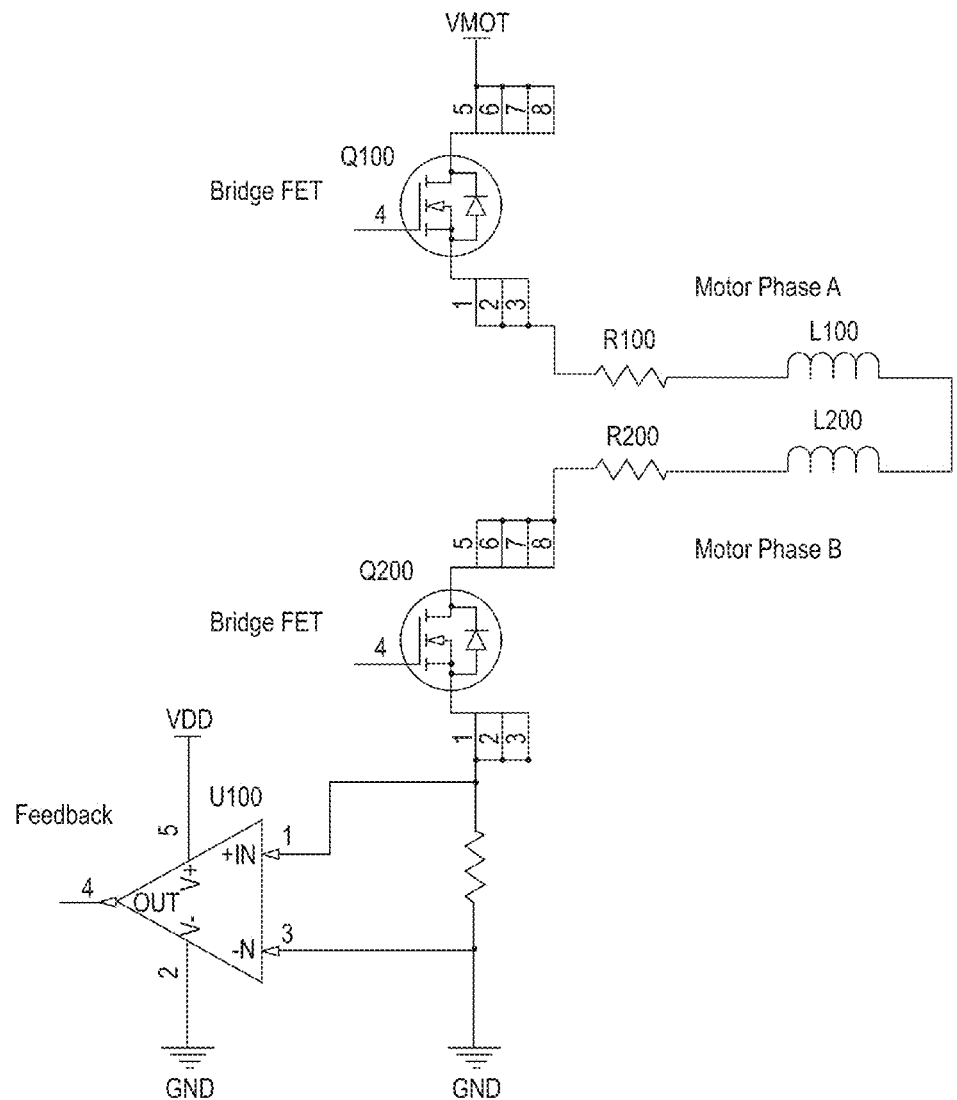
FIG. 17 is a circuit diagram illustrating an example circuit that may implement adaptive FOC techniques, in accordance with certain aspects of this disclosure.

FIG. 17 is a circuit diagram illustrating an example circuit that may implement adaptive FOC techniques, in accordance with certain aspects of this disclosure. In FOC, before connecting to a motor, certain motor parameters need to be known in order to generate a motor model to perform FOC. Using the techniques of this disclosure, an FOC algorithm may learn the motor parameters while being connected to the motor.

Two motor parameters that are generally needed for the motor model include the resistance and the inductance of the windings of the motor. In FIG. 17, the pump processor may turn on one of the two FETs, which allows current to build up through a resistor and an inductor in the modeled winding, and, via feedback amplifier U100, the pump processor calculates a frequency response in order to determine the values of the resistance and inductance of the windings of a particular motor phase. Although shown as current feedback, U100 may instead provide voltage feedback.

For example, the pump processor may close FET Q200 and pulse FET Q100, which sends a voltage step response to the motor. At one time constant, there is a first voltage level, and at three time constants there is a second voltage level. Knowing time and the voltage levels, the pump processor may calculate the time constant of the motor windings, which allows the pump processor to determine 8200 and L200 via feedback provided through feedback amplifier U100. The resistance and inductance of the windings of motor phase A may be determine in a similar manner by closing FET Q100 and pulsing FET Q200. Although not depicted, similar circuitry may be used to determine the resistance and inductance of motor phase C. In this manner, an FOC algorithm may learn the motor parameters while being connected to the motor, thereby providing the system with adaptive FOC techniques. In summary, the circuit of FIG. 17 may determine at least one motor parameter, e.g., the resistance of a motor winding, the inductance of the motor winding, and the like, and adjust the motor using field oriented control based on the at least one determined motor parameter.

Figure 18:
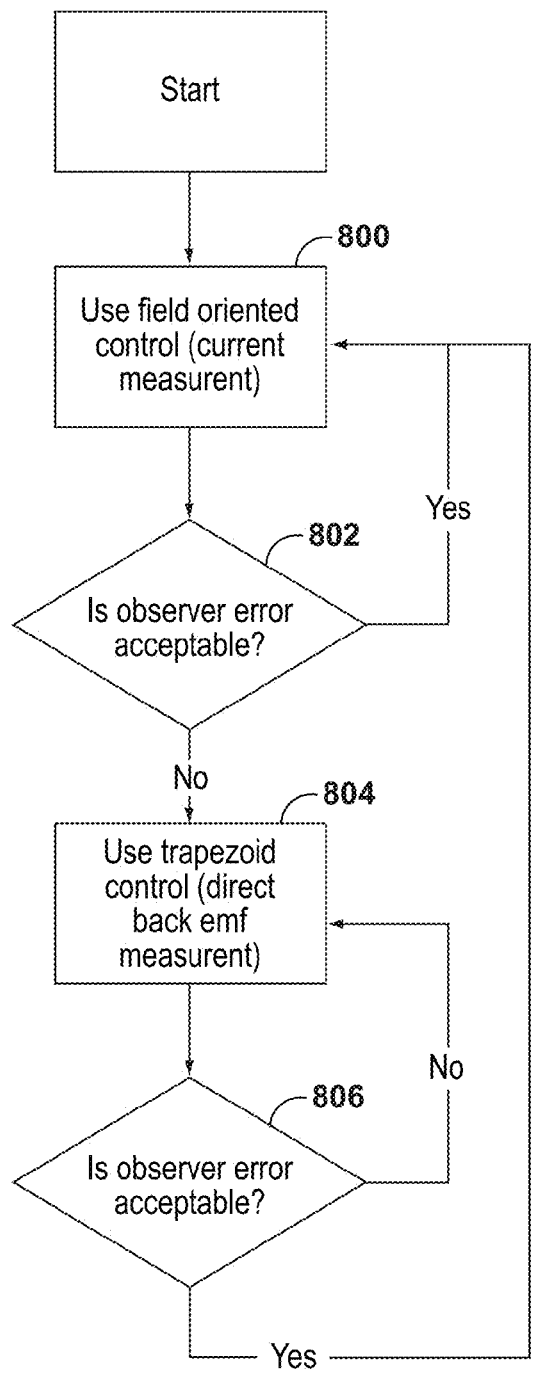
FIG. 18 is a flow diagram illustrating control techniques for selecting between trapezoidal control and FOC to control an electric motor of an implantable blood pump.

FIG. 18 is a flow diagram illustrating control techniques for selecting between trapezoidal control and field oriented control. As shown in FIG. 18, the system may begin using field oriented control (800), which uses current sense circuitry 720-724 of FIG. 16 to determine back EMF for feedback purposes (as described above). In one example implementation, the field oriented control is a sensorless control. Next, the pump processor determines an error parameter (802). The goal of sensorless field oriented control is to know the rotational position of the rotor, but it cannot measure that position directly. As such, an "observer" is created, which is a mathematical model that can infer the rotational position based on measurable parameters, such as the voltages to the motor and the currents from the motor. In order to determine the error, a mathematical model is created based on parameter measurements and compared to a previously determined estimate. The difference between the model and the estimate creates an error term. If the error term is relatively small, than the model is determined to be acceptable and the rotational position of the motor is where it was expected to be. The position of the rotor is important for commutation as well as speed determination purposes.

If the error is acceptable ("YES" branch of 802), then the pump processor continues to use FOC at 800. However, if the error is not acceptable ("NO" branch of 802), then the pump processor may switch to trapezoidal control at 804, which uses voltage measurements provided by back EMF circuitry 718 of FIG. 16 (described above).

After switching to trapezoidal control at 804, an error term is calculated again at 806. If the error term is acceptable ("YES" branch of 806), then the pump processor may switch to FOC. However, if the error term is still not acceptable ("NO" branch of 806), then the pump processor may continue to use trapezoidal control techniques.

FIGS. 19A and 19B are plan and elevation views, respectively, of removable battery 24 and battery release latch 900 for use with a control and power source module according to this disclosure, e.g. control and power source module 12 of FIGS. 2A-4B. Although only one battery release latch 900 is illustrated in the FIG. 19A, a second similarly configured battery release latch may be arranged on the opposite side of the control and power source module such that both latches may be engaged to release removable battery 24. In the example of FIGS. 19A and 19B, battery release latch 900 includes push button 902, catch 904, pivot 906, and spring return 908. Removable battery 24 includes stop 910 configured to engage catch 904 on battery release latch 900 to lock the battery in housing 22 of control and power source module 12.

In FIGS. 19A and 19B, push button 902 and catch 904 of battery release latch 900 are connected and pivot about pivot 906. Spring return 908 is arranged to abut and engage push button 902 to bias the battery lease latch 900 such that catch 904 pivots about pivot 906 to engage stop 910 on removable battery 24. To release removable battery 24, a user may push on push button 902, causing push button 902 and catch 904 to pivot about pivot 906 such that catch 904 moves out of engagement with stop 910 on removable battery 24. Removable battery 24 may be manually removed by the user after unlatching battery release latch 900 or control and power source module 12 may include automatic eject mechanism that ejects the battery at least partially out of housing 22 when the latch is no longer engaging the battery.

Figure 20A:
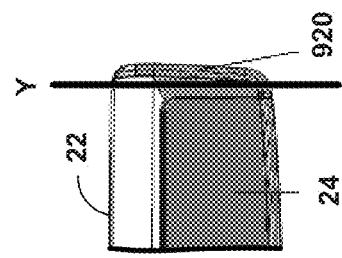
FIGS. 20A-20D illustrate two other battery release latch mechanisms that may be employed in conjunction with control and power source modules according to this disclosure.
Figure 20B:
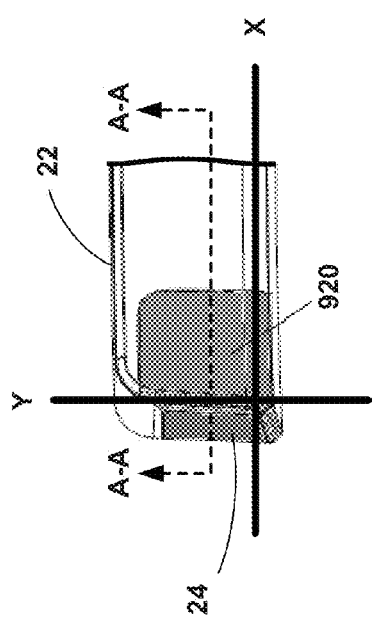
Figure 20C:
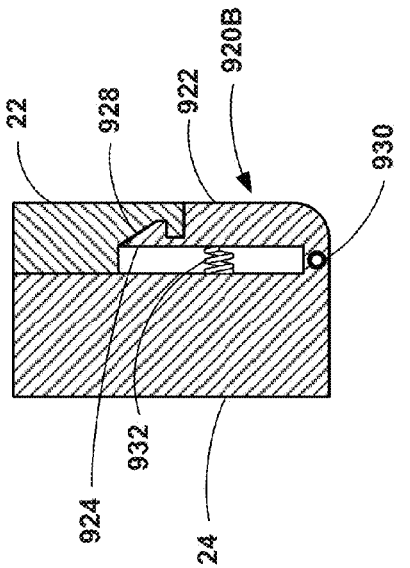
Figure 20D:
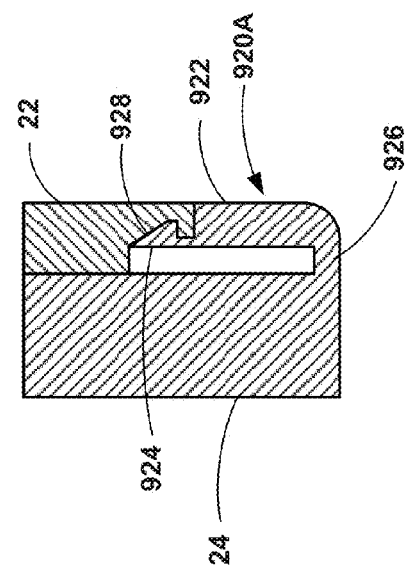

FIGS. 20A and 20B are broken plan and elevation views, respectively, of removable battery 24 and another type of battery release latch 920 for use with a control and power source module according to this disclosure, e.g. control and power source module 12 of FIGS. 2A-4B. FIGS. 20C and 20D are section views cut along section line A-A of FIG. 20A illustrating two different examples of battery release latch 920. Although only one battery release latch 920 is illustrated in the FIGS. 20A-20D, a second similarly configured battery release latch may be arranged on the opposite side of the control and power source module such that both latches may be engaged to release removable battery 24. In FIGS. 20A and 20B, battery release latch 920 is integral with removable battery 24 and configured with push buttons that may pivot about the X-axis (horizontal in the view of FIG. 20A) or the Y-axis (vertical in the view of FIGS. 20A and 20B). The examples illustrated in FIGS. 20C and 20D both include push buttons configured to pivot about axis Y. However, in other examples, a battery release latch may be configured in accordance with the examples of FIGS. 20C and 20D with the push buttons pivoting about the X-axis.

In the example of FIG. 20C, battery release latch 920A integral with removable battery 24 includes push button 922, catch 924, and resilient tab 926. Housing 22 includes stop 928 configured to engage catch 924 on battery release latch 920A to lock the battery in housing 22 of the control and power source module. Push button 922 and catch 924 of battery release latch 920A are configured to rotate at resilient tab 926. Resilient tab 926 may, in one example, be formed from a resilient material that biases battery lease latch 920A such that catch 924 pivots about resilient tab 926 to engage stop 928 on housing 22. To release removable battery 24, a user may push on push button 922, causing resilient tab 926 to flex, which permits push button 922 and catch 924 to pivot about resilient tab 926 such that catch 924 moves out of engagement with stop 928 on housing 22. Removable battery 24 may be manually removed by the user after unlatching battery release latch 920A or the control and power source module may include an automatic eject mechanism that ejects the battery at least partially out of housing 22 when the latch is no longer engaging the battery.

In the example of FIG. 20D, battery release latch 920B integral with removable battery 24 includes push button 922, catch 924, pivot 930, and spring return 932. In this example, push button 922 and catch 924 of battery release latch 920B are configured to rotate about pivot 930. Spring return 932 is arranged to abut and engage push button 922 to bias the battery lease latch 920B such that catch 924 pivots about pivot 930 to engage stop 928 on housing 22. To release removable battery 24, a user may push on push button 922, compressing spring return 932 and causing push button 922 and catch 924 to pivot about pivot 930 such that catch 924 moves out of engagement with stop 928 on housing 22. Removable battery 24 may be manually removed by the user after unlatching battery release latch 920B or the control and power source module may include an automatic eject mechanism that ejects the battery at least partially out of housing 22 when the latch is no longer engaging the battery.

The foregoing examples disclose a number of concepts related to control and power sourced modules employed in VADs. Although the disclosed examples have, in some cases, been described in the context of particular physical and/or logical implementations of a control and power source module or other VAD component, combinations other than those specifically described are possible. For example, the one removable and one internal battery design illustrated in and described with reference to the control and power source module of FIGS. 1-10B may be implemented in a hinged housing design such as that disclosed in U.S. Provisional App. No. 61/311,078, entitled "PORTABLE CONTROLLER AND POWER SOURCE FOR MECHANICAL CIRCULATION SUPPORT SYSTEMS," which was filed on Mar. 5, 2010 and which is incorporated herein by this reference. Similarly, the design of FIGS. 1-10B, although described with reference to the removable and internal battery design, may be implemented as a two removable battery control and power source module.

Techniques described in this disclosure related to functions executed by control electronics of a VAD device may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Some techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, magnetic media, optical media, or other computer readable media.

Various examples have been described. These and other examples are within the scope of the following claims.

The invention claimed is:

1. A device for a mechanical circulation support (MCS) system comprising:
control electronics configured to control an electric motor according to a field-oriented control (FOC) algorithm, the electric motor being configured to drive an implantable pump included in the MCS system.

2. The device of claim 1, wherein the control electronics are further configured to:
determine an observer error for an observer that is used to control the electric motor according to the FOC algorithm while controlling the electric motor according to the FOC algorithm; and
switch from using the FOC algorithm for controlling the electric motor to using a control algorithm other than the FOC algorithm for controlling the electric motor based on the determined observer error.

3. The device of claim 2, wherein the observer error comprises an error parameter.

4. The device of claim 2, wherein the observer error comprises an error of an estimated back electromotive force (EMF) of the electric motor.

5. The device of claim 2, wherein the control electronics are further configured to:
while controlling the electric motor according to the FOC algorithm, estimate the back electromotive force (EMF) of the electric motor;
determine an error of the estimated back EMF;
compare the error of the estimated back EMF to a threshold; and
control the electric motor employing the control algorithm other than the FOC algorithm if the error of the estimated back EMF is greater than the threshold.

6. The device of claim 5, wherein the control electronics are further configured to:
determine a rotational position of a rotor of the electric motor based on the estimated back EMF of the electric motor.

7. The device of claim 6, wherein the control electronics are further configured to:
determine a pulse width modulated (PWM) voltage signal to send to the electric motor to drive an implantable pump based on the rotational position of the rotor of the electric motor.

8. The device of claim 5, wherein the control electronics are further configured to:
sense current from the electric motor; and
estimate the back EMF of the electric motor based on the sensed current from the electric motor.

9. The device of claim 2, wherein the observer compares measureable parameters of a motor driving pump to a model.

10. The device of claim 2, wherein the observer comprises at least one of a sliding mode observer and a luenberger observer.

11. The device of claim 2, wherein the control electronics are further configured to:
determine whether the observer error is acceptable; and
switch from using the FOC algorithm for controlling the electric motor to using the control algorithm other than the FOC algorithm for controlling the electric motor in response to determining that the observer error is not acceptable.

12. The device of claim 11, wherein the control electronics are further configured to:
continue to use the FOC algorithm for controlling the electric motor in response to determining that the observer error is acceptable.

13. The device of claim 1, wherein the pump is configured to receive blood from a source and pump the blood to one or more destinations within a body of a patient.

14. The device of claim 1, wherein the device is external to a patient in which the implantable pump is implanted.

15. A method for driving an implantable pump in a mechanical circulation support (MCS) system comprising:
controlling an electric motor according to a field-oriented control (FOC) algorithm, the electric motor being configured to drive the implantable pump included in the MCS system.

16. The method of claim 15, further comprising:
- determining an observer error for an observer that is used to control the electric motor according to the FOC algorithm while controlling the electric motor according to the FOC algorithm; and
- switching from using the FOC algorithm for controlling the electric motor to using a control algorithm other than the FOC algorithm for controlling the electric motor based on the determined observer error.

17. The method of claim 16, wherein the observer error comprises an error parameter.

18. The method of claim 16, wherein the observer error comprises an error of an estimated back electromotive force (EMF) of the electric motor.

19. The method of claim 16, further comprising:
- while controlling the electric motor according to the FOC algorithm, estimating the back electromotive force (EMF) of the electric motor,
- wherein switching from using the FOC algorithm for controlling the electric motor to using the control algorithm other than the FOC algorithm for controlling the electric motor based on the determined observer error comprises:
- determining an error of the estimated back EMF;
- comparing the error of the estimated back EMF to a threshold; and
- controlling the electric motor employing the control algorithm other than the FOC algorithm if the error of the estimated back EMF is greater than the threshold.

20. The method of claim 19, further comprising:
- determining a rotational position of a rotor of the electric motor based on the estimated back EMF of the electric motor.

21. The method of claim 20, further comprising:
- determining a pulse width modulated (PWM) voltage signal to send to the electric motor to drive an implantable pump based on the rotational position of the rotor of the electric motor.

22. The method of claim 19, wherein estimating the back EMF of the electric motor comprises:
- sensing current from the electric motor; and
- estimating the back EMF of the electric motor based on the sensed current from the electric motor.

23. The method of claim 16, wherein the observer compares measureable parameters of a motor driving pump to a model.

24. The method of claim 16, wherein the observer comprises at least one of a sliding mode observer and a luenberger observer.

25. The method of claim 16, wherein switching from using the FOC algorithm for controlling the electric motor to using the control algorithm other than the FOC algorithm for controlling the electric motor based on the determined observer error comprises:
- determining whether the observer error is acceptable; and
- switching from using the FOC algorithm for controlling the electric motor to using the control algorithm other than the FOC algorithm for controlling the electric motor in response to determining that the observer error is not acceptable.

26. The method of claim 25, wherein switching from using the FOC algorithm for controlling the electric motor to using the control algorithm other than the FOC algorithm for controlling the electric motor based on the determined observer error further comprises:
- continuing to use the FOC algorithm for controlling the electric motor in response to determining that the observer error is acceptable.

27. The method of claim 15, wherein the pump is configured to receive blood from a source and pump the blood to one or more destinations within a body of a patient.

28. The method of claim 15, wherein controlling an electric motor according to the FOC algorithm comprises:
- controlling, with a device, the electric motor according to the FOC algorithm.

29. The method of claim 28, wherein the device is external to a patient in which the implantable pump is implanted.

* * * * *